US007183260B2

(12) United States Patent
Karanewsky et al.

(10) Patent No.: US 7,183,260 B2
(45) Date of Patent: Feb. 27, 2007

(54) C-TERMINAL MODIFIED OXAMYL DIPEPTIDES AS INHIBITORS OF THE ICE/CED-3 FAMILY OF CYSTEINE PROTEASES

(75) Inventors: Donald S Karanewsky, Escondido, CA (US); Robert J Ternansky, San Diego, CA (US); Steven D Linton, San Diego, CA (US); Thang Dinh, Garden Grove, CA (US)

(73) Assignee: Idun Pharmaceuticals, Inc., San Diego, CA (US)

( * ) Notice: Subject to any disclaimer, the term of this patent is extended or adjusted under 35 U.S.C. 154(b) by 1 day.

(21) Appl. No.: 10/926,800

(22) Filed: Aug. 25, 2004

(65) Prior Publication Data

US 2005/0020504 A1 Jan. 27, 2005

Related U.S. Application Data

(63) Continuation of application No. 09/765,105, filed on Jan. 16, 2001, now Pat. No. 7,053,056, which is a continuation-in-part of application No. 09/745,204, filed on Dec. 19, 2000, now Pat. No. 6,544,951, and a continuation-in-part of application No. 09/177,549, filed as application No. PCT/US99/15074 on Jul. 1, 1999, now Pat. No. 6,197,750.

(60) Provisional application No. 60/091,689, filed on Jul. 2, 1998.

(51) Int. Cl.
*C07K 5/06* (2006.01)

(52) U.S. Cl. ........................ 514/19; 548/517; 548/527; 544/360; 546/278.4

(58) Field of Classification Search .................. 514/19; 548/517, 527; 544/360; 546/278.4
See application file for complete search history.

(56) References Cited

U.S. PATENT DOCUMENTS

| 5,869,519 | A | 2/1999 | Karanewsky et al. | ........ 514/415 |
| 5,877,197 | A | 3/1999 | Karanewsky et al. | ....... 514/397 |
| 5,968,927 | A | 10/1999 | Karanewsky et al. | ....... 514/214 |
| 6,197,750 | B1 | 3/2001 | Karanewsky et al. | ......... 514/19 |
| 6,235,899 | B1 | 5/2001 | Bouchet et al. | ............. 540/500 |
| 6,544,951 | B2 | 4/2003 | Karanewski et al. | .......... 514/19 |

FOREIGN PATENT DOCUMENTS

| EP | 618 223 | 10/1994 |
| EP | 623 592 | 11/1994 |
| WO | WO 97/22619 | 6/1997 |
| WO | WO 98/10778 | 3/1998 |
| WO | WO 99/03852 | 1/1999 |
| WO | WO 00/01666 | 1/2000 |
| WO | WO 00/23421 | 4/2000 |
| WO | WO 01/00658 | 1/2001 |
| WO | WO 01/51462 | 7/2001 |
| WO | WO01/81330 | 11/2001 |

OTHER PUBLICATIONS

Chapman K., "Synthesis of a Potent, Reversible Inhibitor of Interleukin-1β Converting Enzyme," *Bioorganic & Medicinal Chemistry Letters* 2(6):613-618, 1992.
Cheung et al., "Synthesis of 3-Amino-3-Vinylpropanoic Acid and its Conversion to 4-Amino-5-Hydroxy-4,5-Dihydrofuran-2-one Hydrochloride (HAD), A Cyclic Stabilised Form of Aspartate 1-Semialdehyde Hydrocholride," *Tetrahedron* 53(46):15807-15812, 1997.
De Lange et al., "Asymmetric 1,4-Additions to 5-Alkoxy-2(5H)-Furanones Enantioselective Synthesis and Absolute Configuration Determination of β-Amino-γ-Butyrolactones and Amino Diols," *Tetrahedron* 45(21):6799-6818, 1989.
Faber et al., "Catalytic Kinetic Resolution of 5-Alkoxy-2(5H)-Furanones," *Tetrahedron* 50(16):4775-4794, 1994.
Feringa et al., "Asymmetric Synthesis of 2-Amino-1, 4-Diols," *Tetrahedron Letters* 29(11):1303-1306, 1988.
Feringa et al., "1, 4-Additions of Amines to 5-Methoxyfuran-2(5H)-One; An Efficient Synthesis of Amino Diols," *Heterocycles* 27(5):1197-1205, 1988.
Furuichi et al., "Common Synthetic Strategy for Optically Active Cyclic Terpenoids having a 1,1,5-Trimethyl-*Trans*-Decalin Nucleus: Syntheses of (+)-Acuminolide, (+)-Spongianolide A, and (+)-Scalarenedial," *Tetrahedron* 57:8425-8442, 2001.
Gagliardini et al., "Prevention of Vertebrate Neuronal Death by the crmA Gene," *Science* 263:826-828, Feb. 11, 1994.
Gonzalez et al., "Pseudoesters and Derivatives. Part38.[1] 1,3-Dipolar Cycloadditions of Aryl Azides and an Aziridine, *Via* Azomethine Ylide, to 2(5H)-Furanones Substituted at the 5-Position by Methoxy and Sulfur Bearing Groups," *Heterocycles* 52(1):237-251, 2000.
Illugunin et al., "Protease activity of m-vitro transcribed and translated caenorhabditis elegans cell death gene (ced-3) product," J. Biol. Chem., Feb. 16, 1996, 271(7) 3517-12 abstract only, 1996.
Juan TS et al., "Molecular characterization of mouse and rat CPP32 beta gene encoding a cysteine protease resembling interleukin-1 beta convesting enzyme and CED-3," Oncogene, 13(4)749-55, Aug. 15, 1996 (Abstract only).
Leblanc et al., "Sar in the Alkoxy Lactone Series: The Discovery of DFP, A Potent and Orally Active Cox-2 Inhibitor," *Bioorganic & Medicinal Chemistry Letters* 9, pp. 2207-2212, 1999.
Lubben et al., "Asymmetric Synthesis of β-Lactams via Amine Additions to 5(R)- Menthyloxy-2[5H]-Furanone," *Tetrahedron: Asymmetry* 2(8):775-778, 1991.
Marx, "Cell Death Studies Yield Cancer Clues," *Science* 259:760-761, Feb. 5, 1993.
Sleath et al., "Substrate Specificity of the Protease that Processes Human Interleukin-1.beta.," *J. Biol. Chem.* 265(24):14526-14528, Aug. 25, 1990.

*Primary Examiner*—David Lukton
(74) *Attorney, Agent, or Firm*—Seed IP Law Group PLLC

(57) ABSTRACT

This invention is directed to novel oxamyl dipeptide ICE/ced-3 family inhibitor compounds. The invention is also directed to pharmaceutical compositions containing these compounds, as well as to the use of such compositions in the treatment of patients suffering inflammatory, autoimmune and neurodegenerative diseases, for the prevention of ischemic injury, and for the preservation of organs that are to undergo a transplantation procedure.

54 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Substrate for the ICE assay (AMC)
<220> FEATURE:
<221> NAME/KEY: ACETYLATION
<222> LOCATION: 1
<220> FEATURE:
<221> NAME/KEY: MOD_RES
<222> LOCATION: 4
<223> OTHER INFORMATION: amino-4-methylcoumarin

<400> SEQUENCE: 1

Tyr Val Ala Asp
 1

<210> SEQ ID NO 2
<211> LENGTH: 4
<212> TYPE: PRT
<213> ORGANISM: Artificial Sequence
<220> FEATURE:
<223> OTHER INFORMATION: Substrate for the CPP32, Mch2, Mch3 and Mch5
      assays
<220> FEATURE:
<221> NAME/KEY: ACETYLATION
<222> LOCATION: 1
<220> FEATURE:
<221> NAME/KEY: MOD_RES
<222> LOCATION: 4
<223> OTHER INFORMATION: amino-4-methylcoumarin

<400> SEQUENCE: 2

Asp Glu Val Asp
 1

C-TERMINAL MODIFIED OXAMYL DIPEPTIDES AS INHIBITORS OF THE ICE/CED-3 FAMILY OF CYSTEINE PROTEASES

CROSS-REFERENCE TO RELATED APPLICATIONS

This application is a continuation of U.S. patent application Ser. No. 09/765,105 filed Jan. 16, 2001, now U.S. Pat. No. 7,053,056; which application is a continuation-in-part of U.S. patent application Ser. No. 09/745,204 filed Dec. 19, 2000, now U.S. Pat. No. 6,544,951, and U.S. patent application Ser. No. 09/177,549 filed Oct. 22, 1998, now U.S. Pat. No. 6,197,750, and claims the benefit of International PCT Application No. PCT/US99/15074 filed Jul. 1, 1999 and U.S. Provisional Application No. 60/091,689 filed Jul. 2, 1998 (each of which applications are hereby incorporated by reference in their entirety).

TECHNICAL FIELD

The present invention relates to novel classes of compounds which are inhibitors of interleukin-1β converting enzyme and related proteases ("ICE/ced-3 family of cysteine proteases"), as well as pharmaceutical compositions comprising these compounds and to methods of using such pharmaceutical compositions.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today,* 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.,* 84:4572–4576 (1987); Lonnemann, G. et al., *Eur. J. Immunol.,* 19:1531–1536 (1989).

IL-1β is synthesized as a biologically inactive precursor, proIL-1β. ProIL-1β is cleaved by a cysteine protease called interleukin-1β converting enzyme ("ICE") between Asp-116 and Ala-117 to produce the biologically active C-terminal fragment found in human serum and synovial fluid. Sleath, P. R. et al., *J. Biol. Chem.,* 265:14526–14528 (1992); A. D. Howard et al., *J. Immunol.,* 147:2964–2969 (1991).

ICE is a cysteine protease localized primarily in monocytes. In addition to promoting the pro-inflammatory and immunoregulatory properties of IL-1β, ICE, and particularly its homologues, also appear to be involved in the regulation of cell death or apoptosis. Yuan, J. et al., *Cell,* 75:641–652 (1993); Miura, M. et al., *Cell,* 75:653–660 (1993); Nett-Giordalisi, M. A. et al., *J. Cell Biochem.,* 17B:117 (1993). In particular, ICE or ICE/ced-3 homologues are thought to be associated with the regulation of apoptosis in neurogenerative diseases, such as Alzheimer's and Parkinson's disease. Marx, J. and M. Baringa, *Science,* 259:760–762 (1993); Gagliardini, V. et al., *Science,* 263:826–828 (1994).

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases, such as Alzheimer's and Parkinson's disease. Such inhibitors are also useful for the repopulation of hematopoietic cells following chemo- and radiation therapy and for prolonging organ viability for use in transplantation.

ICE/ced-3 inhibitors represent a class of compounds useful for the control of the above-listed disease states. Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies,* C. R. Clark and W. H. Moos, Eds. (Ellis Horwood, Chichester, England, 1990), pp. 92–126. These undesirable properties have hampered their development into effective drugs.

Accordingly, the need exists for compounds that can effectively inhibit the action of the ICE/ced-3 family of proteases, for use as agents for preventing unwanted apoptosis, and for treating chronic and acute forms of IL-1 mediated diseases such as inflammatory, autoimmune or neurodegenerative diseases. The present invention satisfies this need and provides further related advantages.

SUMMARY OF THE INVENTION

In general, the compounds of this invention incorporate a (N-substituted)oxamyl group as a dipeptide mimetic. The resulting compounds exhibit improved properties relative to their peptidic counterparts, for example, such as improved cell penetration or improved absorption and metabolic stability resulting in enhanced bioavailability. This application claims priority from U.S. Provisional Application No. 60/091,689, filed Jul. 2, 1998, and U.S. application Ser. No. 09/177,549, filed Oct. 22, 1998 (both of which are hereby incorporated by reference in their entirety).

One aspect of the instant invention is the compounds of the Formula I:

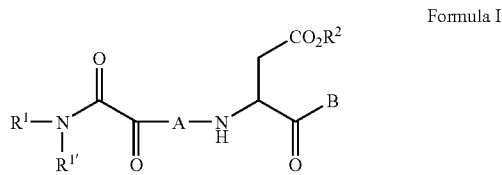

Formula I wherein A, B, R$^1$, R$^{1'}$ and R$^2$ are as defined below, as well as pharmaceutically acceptable salts thereof A further aspect of the instant invention is a pharmaceutical composition comprising a compound of the above Formula I and a pharmaceutically-acceptable carrier therefor.

Another aspect of this invention involves a method for treating an autoimmune disease comprising administering an effective amount of a pharmaceutical composition discussed above to a patient in need of such treatment.

Yet another aspect of the instant invention is a method for treating an inflammatory disease comprising administering an effective amount of a pharmaceutical composition discussed above to a patient in need of such treatment.

A further aspect of the instant invention is a method for treating a neurodegenerative disease comprising administering an effective amount of a pharmaceutical composition discussed above to a patient in need of such treatment.

Another aspect of the instant invention is a method of preventing ischemic injury to a patient suffering from a disease associated with ischemic injury comprising administering an effective amount of the pharmaceutical composition discussed above to a patient in need of such treatment.

A further aspect of the instant invention is a method for expanding of hematopoietic cell populations and/or enhancing their survival by contacting the cells with an effective amount of the pharmaceutical composition discussed above. Cell populations included in the method of the invention include (but are not limited to) granulocytes, monocytes, erthrocytes, lymphocytes and platelets for use in cell transfusions.

An alternate aspect of the instant invention is a method of prolonging the viability of an organ that has been removed from the donor for the purpose of a future transplantation procedure, which comprises applying an effective amount of the pharmaceutical composition discussed above to the organ, thereby prolonging the viability of the organ as compared to an untreated organ. The organ may be an intact organ, or isolated cells derived from an organ (e.g., isolated pancreatic islet cells, isolated dopaminergic neurons, blood or hematopoietic cells).

These and other aspects of this invention will be evident upon reference to the following detailed description.

DETAILED DESCRIPTION OF THE INVENTION

As mentioned above, one aspect of the instant invention is the compounds of the Formula I:

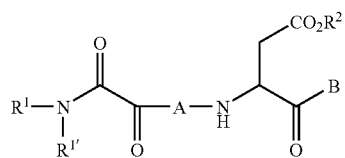

Formula I wherein:

A is a natural or unnatural amino acid of Formula IIa–i:

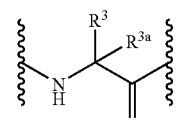

IIa

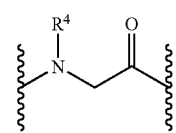

IIb

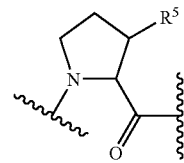

IIc

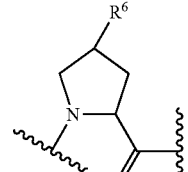

IId

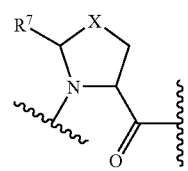

IIe

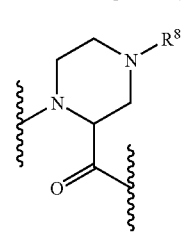

IIf

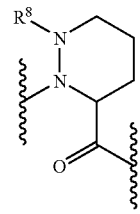

IIg

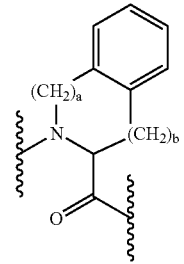

IIh

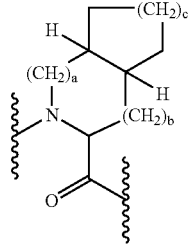

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, (CH$_2$)$_n$cycloalkyl, (CH$_2$)$_n$phenyl, (CH$_2$)$_n$(substituted phenyl), (CH$_2$)$_n$(1 or 2-naphthyl), (CH$_2$)$_n$(substituted 1 or 2-naphthyl), (CH$_2$)$_n$(heteroaryl), (CH$_2$)$_n$(substituted heteroaryl), halomethyl, CO$_2$R$^{12}$, CONR$^{13}$R$^{14}$, CH$_2$ZR$^{15}$, CH$_2$OCO(aryl), CH$_2$OCO(heteroaryl), or CH$_2$OPO(R$^{16}$)R$^{17}$, where Z is an oxygen or a sulfur atom, or B is a group of the Formula IIIa–c:

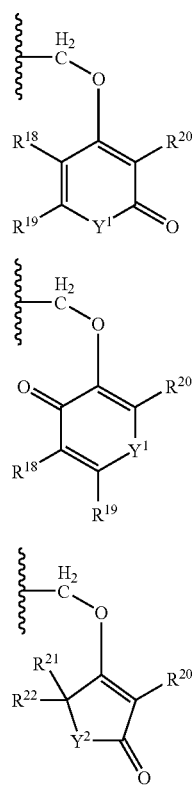

IIIa

IIIb

IIIc

R$^1$ is alkyl, cycloalkyl, substituted cycloalkyl, (cycloalkyl)alkyl, substituted (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heterocycle, substituted heterocycle, (heterocycle)alkyl, substituted (heterocycle)alkyl, R$^{1a}$(R$^{1b}$)N, or R$^{1c}$O;

R$^{1'}$ is hydrogen, alkyl, phenyl, substituted phenyl, naphthyl, substituted naphthyl, heterocycle or substituted heterocycle;

or R$^1$ and R$^{1'}$ taken together with the nitrogen atom to which they are attached form a heterocycle or substituted heterocycle;

R$^2$ is hydrogen, lower alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, or substituted (1 or 2 naphthyl)alkyl;

and wherein:

R$^{1a}$ and R$^{1b}$ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl, with the proviso that R$^{1a}$ and R$^{1b}$ cannot both be hydrogen;

R$^{1c}$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl;

R$^3$ is C$_{1-6}$ lower alkyl, cycloalkyl, phenyl, substituted phenyl, (CH$_2$)$_n$NH$_2$, (CH$_2$)$_n$NHCOR$^9$, (CH$_2$)$_n$N(C=NH)NH$_2$, (CH$_2$)$_m$CO$_2$R$^2$, (CH$_2$)$_m$OR$^{10}$, (CH$_2$)$_m$SR$^{11}$, (CH$_2$)$_n$cycloalkyl, (CH$_2$)$_n$phenyl, (CH$_2$)$_n$(substituted phenyl), (CH$_2$)$_n$(1 or 2-naphthyl) or (CH$_2$)$_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

R$^{3a}$ is hydrogen or methyl, or R$^3$ and R$^{3a}$ taken together are —(CH$_2$)$_d$— where d is an interger from 2 to 6;

R$^4$ is phenyl, substituted phenyl, (CH$_2$)$_m$phenyl, (CH$_2$)$_m$(substituted phenyl), cycloalkyl, or benzofused cycloalkyl;

R$^5$ is hydrogen, lower alkyl, cycloalkyl, phenyl, substituted phenyl, (CH$_2$)$_n$cycloalkyl, (CH$_2$)$_n$phenyl, (CH$_2$)$_n$(substituted phenyl), or (CH$_2$)$_n$(1 or 2-naphthyl);

R$^6$ is hydrogen, fluorine, oxo, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), (CH$_2$)$_n$(1 or 2-naphthyl), OR$^{10}$, SR$^{11}$ or NHCOR$^9$;

R$^7$ is hydrogen, oxo (i.e., =O), lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), or (CH$_2$)$_n$(1 or 2-naphthyl);

R$^8$ is lower alkyl, cycloalkyl, (CH$_2$)$_n$cycloalkyl, (CH$_2$)$_n$phenyl, (CH$_2$)$_n$(substituted phenyl), (CH$_2$)$_n$(1 or 2-naphthyl), or COR$^9$;

R$^9$ is hydrogen, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), (CH$_2$)$_n$(1 or 2-naphthyl), OR$^{12}$, or NR$^{13}$R$^{14}$;

R$^{10}$ is hydrogen, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), or (CH$_2$)$_n$(1 or 2-naphthyl);

R$^{11}$ is lower alkyl, cycloalkyl, phenyl, substituted phenyl, naphthyl, (CH$_2$)$_n$cycloalkyl, (CH$_2$)$_n$phenyl, (CH$_2$)$_n$substituted phenyl), or (CH$_2$)$_n$(1 or 2-naphthyl);

R$^{12}$ is lower alkyl, cycloalkyl, (CH$_2$)$_n$cycloalkyl, (CH$_2$)$_n$phenyl, (CH$_2$)$_n$(substituted phenyl), or (CH$_2$)$_n$(1 or 2-naphthyl);

R$^{13}$ is hydrogen, lower alkyl, cycloalkyl, phenyl, substituted phenyl, naphthyl, substituted naphthyl, (CH$_2$)$_n$cycloalkyl, (CH$_2$)$_n$phenyl, (CH$_2$)$_n$(substituted phenyl), or (CH$_2$)$_n$(1 or 2-naphthyl);

R$^{14}$ is hydrogen or lower alkyl;

or R$^{13}$ and R$^{14}$ taken together form a five to seven membered carbocyclic or heterocyclic ring, such as morpholine, or N-substituted piperazine;

R$^{15}$ is phenyl, substituted phenyl, naphthyl, substituted naphthyl, heteroaryl, (CH$_2$)$_n$phenyl, (CH$_2$)$_n$(substituted phenyl), (CH$_2$)$_n$(1 or 2-naphthyl), or (CH$_2$)$_n$(heteroaryl);

R$^{16}$ and R$^{17}$ are independently lower alkyl, cycloalkyl, phenyl, substituted phenyl, naphthyl, phenylalkyl, substituted phenylalkyl, or (cycloalkyl)alkyl;

$R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are —(CH═CH)$_2$—;

$R^{20}$ is hydrogen, alkyl, phenyl, substituted phenyl, $(CH_2)_n$ phenyl, $(CH_2)_n$(substituted phenyl);

$R^{21}$, $R^{22}$ and $R^{23}$ are independently hydrogen, or alkyl;

X is $CH_2$, $(CH_2)_2$, $(CH_2)_3$, or S;

$Y^1$ is O or $NR^{23}$;

$Y^2$ is $CH_2$, O, or $NR^{23}$;

a is 0 or 1;

b is 1 or 2, provided that when a is 1 then b is 1;

c is 1 or 2, provided that when c is 1 then a is 0 and b is 1;

m is 1 or 2; and n is 1, 2, 3 or 4;

or a pharmaceutically acceptable salt thereof.

As used herein, the term "alkyl" means a straight or branched $C_1$ to $C_{10}$ carbon chain, such as methyl, ethyl, tert-butyl, iso-propyl, n-octyl, and the like. The term "lower alkyl" means a straight chain or branched $C_1$ to $C_6$ carbon chain, such as methyl, ethyl, iso-propyl, and the like.

The term "cycloalkyl" means a mono-, bi-, or tricyclic ring that is either fully saturated, partially of fully unsaturated, or aromatic. Examples of such a ring include cyclopropyl, cyclobutyl, cyclopentyl, cyclohexyl, cycloheptyl, adamantyl, cyclooctyl, cis- or trans decalin, bicyclo[2.2.1] hept-2-ene, cyclohex-1-enyl, cyclopent-1-enyl, 1,4-cyclooctadienyl, and the like.

The term "(cycloalkyl)alkyl" means the above-defined alkyl group substituted with one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more substituents chosen from halogen, hydroxy, protected hydroxy, cyano, nitro, trifluoromethyl, alkyl, alkoxy, acyl, acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-(lower alkyl)carboxamide, protected N-(lower alkyl)carboxamide, N,N-di(lower alkyl)carboxamide, N-((lower alkyl)sulfonyl)amino, N-(phenylsulfonyl) amino, substituted or unsubstituted heterocycle, substituted or unsubstituted cycloalkyl, or by a substituted or unsubstituted phenyl group, such that in the latter case a biphenyl or naphthyl group results, or wherein two adjacent alkyl substituents on the substituted phenyl ring taken together form a cycloalkyl to yield, for example, tetrahydronaphthyl or indanyl.

Examples of the term "substituted phenyl" includes a mono-, di-, tri-, tetra- or penta(halo)phenyl group such as 2-, 3- or 4-chlorophenyl, 2,6-dichlorophenyl, 2,5-dichlorophenyl, 3,4-dichlorophenyl, 2-,3- or 4-bromophenyl, 3,4-dibromophenyl, 3-chloro-4-fluorophenyl, 2-, 3- or 4-fluorophenyl, 2,4,6-trifluorophenyl, 2,3,5,6-tetrafluorophenyl, 2,3,4,5-tetrafluorophenyl, 2,3,4,5,6-pentafluorophenyl, and the like; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-,3- or 4-cyanophenyl; a mono- or di(alkyl) phenyl group such as 2-, 3-, or 4-methylphenyl, 2,4-dimethylphenyl, 2-, 3- or 4-(iso-propyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(iso-propoxy)phenyl, 2-, 3- or 4-(t-butoxy) phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl) phenyl or (protected aminomethyl)phenyl such as 2-, 3- or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "phenylalkyl" means one of the above phenyl groups attached to one of the above-described alkyl groups, and the term "substituted phenylalkyl" means that either the phenyl or the alkyl, or both, are substituted with one or more of the above-defined substituents. Examples of such groups include 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl, and the like.

The term "substituted naphthyl" means a naphthyl group substituted with one or more of the above-identified substituents, and the term "(1 or 2 naphthyl)alkyl" means a naphthyl (1 or 2) attached to one of the above-described alkyl groups.

The terms "halo" and "halogen" refer to the fluoro, chloro, bromo or iodo groups. These terms may also be used to describe one or more halogens, which are the same or different. Preferred halogens in the context of this invention are chloro and fluoro.

The term "aryl" refers to aromatic five and six membered carbocyclic rings. Six membered rings are preferred.

The term "heterocycle" denotes optionally substituted five-membered or six-membered heterocyclic rings that have 1 to 4 heteroatoms, such as oxygen, sulfur and/or nitrogen atoms, in particular nitrogen, either alone or in conjunction with sulfur or oxygen ring atoms, and include aromatic heterocycles (also referred to herein as "heteroaryls"). The following ring systems are representative examples of aromatic heterocyclic radicals denoted by the term heteroaryl (whether substituted or unsubstituted): thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl and indolyl. Non-aromatic heterocycles include, for example, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Substituents for the above optionally substituted cycloalkyl or heterocycle rings are as listed above for substituted phenyl, and more specifically include from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups. More than one substituent may be made at any given atom of the heterocyclic ring, including carbocyclic or heterocyclic substituents that form a spiro union. "Trihalomethyl" can be trifluoromethyl, trichloromethyl, tribromomethyl or triiodomethyl, "lower alkoxy" means a $C_1$ to $C_4$ alkoxy group, similarly, "lower alkylthio" means a $C_1$ to $C_4$ alkylthio group. The term "substituted lower alkyl" means the above-defined lower alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt.

The terms "substituted (cycloalkyl)alkyl" and "substituted cycloalkyl" are as defined above with regard to (cycloalkyl)alkyl and cycloalkyl, but substituted with one or more substituents as identified above with regard to substituted phenyl, cycloalkyl and/or heterocycle. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different. The term "heteroaryl(alkyl)" denotes an alkyl group as defined above, substituted at any position by a heteroaryl group, as above defined.

More specifically, and in addition to the substituents disclosed above, the term "substituted" as used herein means a chemical moiety wherein at least one hydrogen atom is replaced with a substituent. In the case of a keto substituent ("C(=O)") two hydrogen atoms are replaced. Substituents include halogen, hydroxy, alkyl, substituted alkyl (such as haloalkyl, mono- or di-substituted aminoalkyl, alkyloxyalkyl, and the like), aryl, substituted aryl, arylalkyl, substituted arylalkyl, heterocycle, substituted heterocycle, heterocyclealkyl, substituted heterocyclealkyl, —$NR_aR_b$, —$NR_aC(=O)R_b$, —$NR_aC(=O)NR_aR_b$, —$NR_aC(=O)OR_b$— $NR_aSO_2R_b$, —$OR_a$, —$C(=O)R_a$—$C(=O)OR_a$—$C(=O)NR_aR_b$, —$OC(=O)R_a$, —$OC(=O)OR_a$, —$OC(=O)NR_aR_b$, —$NR_aSO_2R_b$, or a radical of the formula —Y-Z-$R_a$ where Y is alkanediyl, substitute alkanediyl, or a direct bond, Z is —O—, —S—, —S(=O)—, —S(=O)$_2$—, —N($R_b$)—, —C(=O)—, —C(=O)O—, —OC(=O)—, —N($R_b$)C(=O)—, —C(=O)N($R_b$)— or a direct bond, wherein $R_a$ and $R_b$ are the same or different and independently hydrogen, amino, alkyl, substituted alkyl (including halogenated alkyl), aryl, substituted aryl, arylalkyl, substituted arylalkyl, heterocycle, substituted heterocycle, heterocylealkyl or substituted heterocyclealkyl, or wherein $R_a$ and $R_b$ taken together with the nitrogen atom to which they are attached form a heterocycle or substituted heterocycle.

Furthermore, the above optionally substituted five-membered or six-membered heterocyclic rings, and the above cycloalkyl rings, can optionally be fused to an aromatic 5-membered or 6-membered aryl, carbocyclic or heterocyclic ring system. For example, the rings can be optionally fused to an aromatic 5-membered or 6-membered ring system such as a pyridine or a triazole system, and preferably to a benzene ring.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); and ammonium ion; and the organic cations (for example, dibenzylammonium, benzylammonium, 2-hydroxyethylammonium, bis(2-hydroxyethyl)ammonium, phenylethylbenzyl-ammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyl-oxycarbonyl, cyclohexanyloxy-carbonyl, 1-methyl-cyclohexanyloxy-carbonyl, 2-methylcyclohexanyl-oxycarbonyl, 2-(4-toluylsulfonyl)ethoxycarbonyl, 2-(methylsulfonyl)ethoxycarbonyl, 2-(triphenylphosphino)-ethoxycarbonyl, 9-fluorenyl-methoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyl-oxycarbonyl ("Cbz"), 4-phenylbenzyloxycarbonyl, 2-methylbenzyloxycarbonyl, α-2,4,5,-tetramethylbenzyloxycarbonyl("Tmz"), 4-methoxybenzyloxycarbonyl, 4-fluorobenzyl-oxycarbonyl, 4-chlorobenzyloxycarbonyl, 3-chlorobenzyloxycarbonyl, 2-chlorobenzyloxy-carbonyl, 2,4-dichlorobenzyloxycarbonyl, 4-bromobenzyloxycarbonyl, 3-bromobenzyloxy-carbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New York, N.Y., 1984 and 1993, and J. M. Stewart and J. D. Young, "Solid Phase Peptide Synthesis," 2nd Ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acid" refers to both the naturally occurring amino acids and other non-proteinogenic α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural alpha-amino acids include hydroxylysine, citrulline, kynurenine, (4-aminophenyl)alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxy-kynurenine, 3-aminotyrosine, trifluoromethylalanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydro-proline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β2- and 3-thienylalanine; β-2- and 3-furanylalanine; β-2-, 3- and 4-pyridylalanine; β-(benzothienyl-2- and 3-yl)alanine; β-(1- and 2-naphthyl)alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine. Any of these α-amino acids may be substituted with a methyl group at the alpha position, a halogen at any position of the aromatic residue on the α-amino side chain, or an appropriate protective group at the O, N, or S atoms of the side chain residues. Appropriate protective groups are discussed above.

Depending on the choice of solvent and other conditions known to the practitioner skilled in the art, compounds of this invention may also take the ketal or acetal form, which forms are included in the instant invention. In particular, when $R^2$ is hydrogen compounds of Formula Ia may exist in the cyclic ketal or acetal form Formula Ia' shown below:

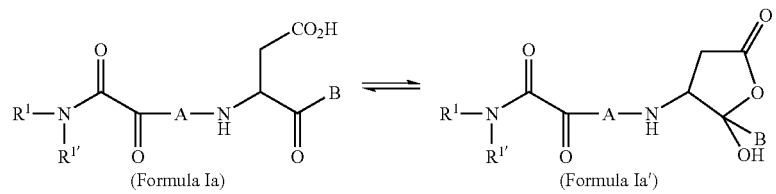

(Formula Ia)     (Formula Ia')

Similarly, when $R^2$ of Formula I is a moiety other than hydrogen, and depending upon the choice of solvents as noted above (e.g., $R^2OH$), the compounds of the cyclic ketal or acetal form include compounds having Formula Ia" as shown below.

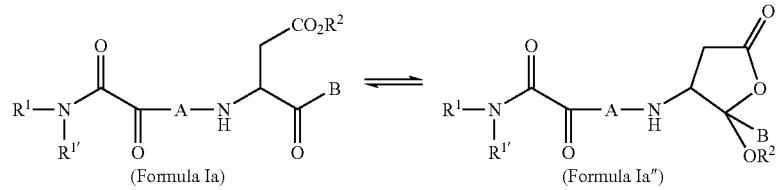

(Formula Ia)     (Formula Ia")

In addition, it should be understood that the equilibrium forms of the compounds of this invention may include tautomeric forms. All such forms of these compounds are expressly included in the present invention.

The compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the group donated as "A" in Formula I or the modified aspartic acid residue attached to the group denoted as "A".

Compounds of this invention with respect to the group "$R^1$" in Formula I, include those wherein:

$R^1$ is phenyl, substituted phenyl, phenylalkyl, substituted phenylalkyl, naphthyl, substituted naphthyl, (1 or 2 naphthyl)alkyl, heteroaryl, or (heteroaryl)alkyl.

More typically, the compounds of this invention with respect to the group "$R^1$" include those wherein:

$R^1$ is phenyl, substituted phenyl, phenylalkyl, substituted phenylalkyl, naphthyl, substituted naphthyl, or (1 or 2 naphthyl)alkyl.

Compounds of this invention with respect to the group "$R^{1'}$" include those wherein:

$R^{1'}$ is hydrogen, lower alkyl and aryl.

Compounds of this invention with respect to the group "A" in Formula I, include those of Formula IIa wherein:

$R^3$ is lower alkyl, cycloalkyl, phenyl, substituted phenyl, $(CH_2)_nNH_2$, $(CH_2)_mOR^{10}$, $(CH_2)_mSR^{11}$, $(CH_2)_n$cycloalkyl, $(CH_2)_n$phenyl, $(CH_2)_n$(substituted phenyl), or $(CH_2)_n$(1 or 2-naphthyl);

$R^{3a}$ is hydrogen;

$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl); and n=1–4 and m=1 or 2.

Compounds of this invention with respect to the group "A" in Formula I, also include those of Formula IIb wherein:

$R^4$ is phenyl, substituted phenyl, $(CH_2)_m$phenyl, $(CH_2)_m$(substituted phenyl), cycloalkyl, or 2-indanyl; and m=1 or 2.

Another group of compounds with respect to the group "A" in Formula I, include those of Formula IId wherein:

$R^6$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$;

$R^{10}$ and $R^{11}$ are independently cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl); and n=1–4.

A fourth group of compounds with respect to the group "A" in Formula I, include those of Formula IIe wherein:

$R^7$ is hydrogen, oxo, cycloalkyl, phenyl, substituted phenyl, or naphthyl; and X=$CH_2$, $(CH_2)_2$, $(CH_2)_3$, or S.

Another group of compounds with respect to the group "A" in Formula I, include those of Formula IIh wherein:

a=0 and b=1 or 2.

Compounds of this invention with respect to the group "B" in Formula I, include those wherein:

- B is hydrogen, 2-benzoxazolyl, substituted 2-oxazolyl, $CH_2ZR^{15}$, $CH_2OCO(aryl)$, or $CH_2OPO(R^{16})R^{17}$, where Z is an oxygen or a sulfur atom;
- $R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);
- $R^{16}$ and $R^{17}$ are independently alkyl, cycloalkyl, phenyl, substituted phenyl, naphthyl, phenylalkyl, substituted phenylalkyl, or (cycloalkyl)alkyl.

Another group of compounds with respect to the group "B" in Formula I, include those of Formula IIIa–c wherein:

- $Y^1$ is O or $NR^{23}$;
- $Y^2$ is $CH_2$, O, or $NR^{23}$;
- $R^{18}$ and $R^{19}$ are independently hydrogen, alkyl, or phenyl, or $R^{18}$ and $R^{19}$ taken together are $-(CH=CH)_2-$;
- $R^{20}$ is hydrogen, alkyl, phenyl, substituted phenyl, $(CH_2)_n$ phenyl, or $(CH_2)_n$(substituted phenyl);
- $R^{21}$, $R^{22}$ and $R^{23}$ are independently hydrogen or alkyl.

The compounds of Formula I may be synthesized using conventional techniques as discussed below. Advantageously, these compounds are conveniently synthesized from readily available starting materials.

One synthetic route for synthesizing the instant compounds is set forth in the following Scheme 1:

SCHEME 1

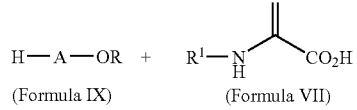

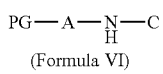
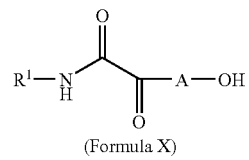

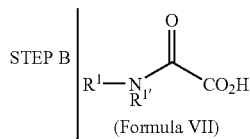

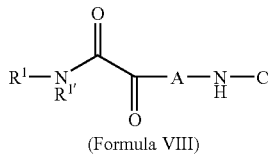

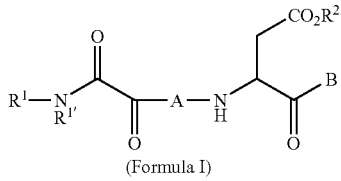

(Formula I)

In the above Scheme 1, Formula (V), that is $H_2N-C$, is a modified aspartic acid residue of Formulas Va through Vd:

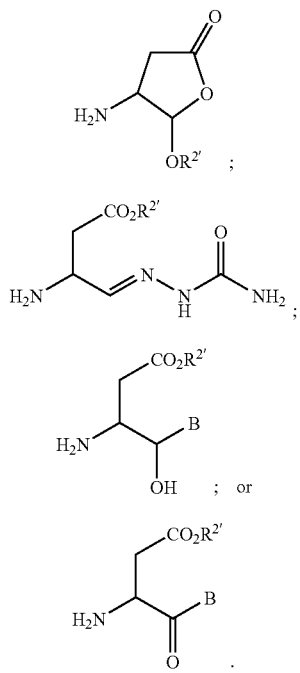

In the above Scheme 1, "PG" stands for an amino protecting group and "A" stands for a natural or unnatural amino acid of formula IIa through IIi, as discussed above. In Formula Va through Vd, $R^{2'}$ is a carboxyl protecting group as described above or an $R^2$ moiety as set forth in the definition of $R^2$ in Formula I, with the exception that $R^{2'}$ cannot be a hydrogen atom.

The modified aspartic acids of Formula Va–d can be prepared by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference.

The coupling reactions carried out under Step A are performed in the presence of a standard peptide coupling agent such as the combination of the combination of dicyclohexylcarbodiimide(DCC) and 1-hydroxy-benzotriazole (HOBt), as well as the BOP (benzotriazolyloxy-tris-(dimethylamino)phosphonium hexafluorophosphate) reagent, pyBOP (benzotriazolyloxy-tris(N-pyrolidinyl)phosphoniumhexafluorophosphate), HBTU (O-benzotriazolyly-tetramethylisouronium-hexafluorophosphate), and EEDQ (1-ethyloxycarbonyl-2-ethyloxy-1,2-dihydroquinoline) reagents, the combination of 1-ethyl(3,3'-dimethyl-1'-aminopropyl)carbodiimide (EDAC) and HOBt, and the like, as discussed in J. Jones, "Amino Acid and Peptide Synthesis," Steven G. Davis ed., Oxford University Press, Oxford, pp. 25–41 (1992); M. Bodanzky, "Principles of Peptide Synthesis," Hafner et al. ed., Springer-Verlag, Berlin Heidelberg, pp. 9–52 and pp. 202–251 (1984); M. Bodanzky, "Peptide Chemistry, A Practical Textbook," Springer-Verlag, Berlin Heidelberg, pp. 55–73 and pp. 129–180; and Stewart and Young, "Solid Phase Peptide Synthesis," Pierce Chemical Company, (1984), all of which are herein incorporated by reference. The amino protecting group is then removed and the resulting amine is coupled to the (N-substituted)oxamic acid of Formula VII (Step B). Again, this coupling reaction uses the standard peptide coupling reactions mentioned above.

Alternatively, the (N-substituted)oxamic acid of Formula VII can be coupled to an amino ester of Formula IX (Step D). Again, this coupling reaction uses the standard peptide coupling reactions mentioned above. In Formula IX, the group R is a carboxyl protecting group such as methyl, allyl, benzyl or tert-butyl. After removal of the carboxyl protecting group under standard conditions well known in the art, the resulting carboxylic acid is coupled to amine V using the standard peptide coupling methods described above (Step E).

In the case where the coupling reaction depicted by either Step A or Step E was carried out with the amino alcohol of Formula Vc, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylamine); and Dess-Martin oxidation (Dess-Martin periodinane, t-butanol, and methylene chloride.) The protecting groups contained in substructures of the Formula Va–d and A (if present) are removed by methods well known in the art. These reactions and removal of some or all of the protecting groups are involved in Step C in the above Scheme 1.

An alternative synthetic route for synthesizing the instant compounds is set forth in the following Scheme 2:

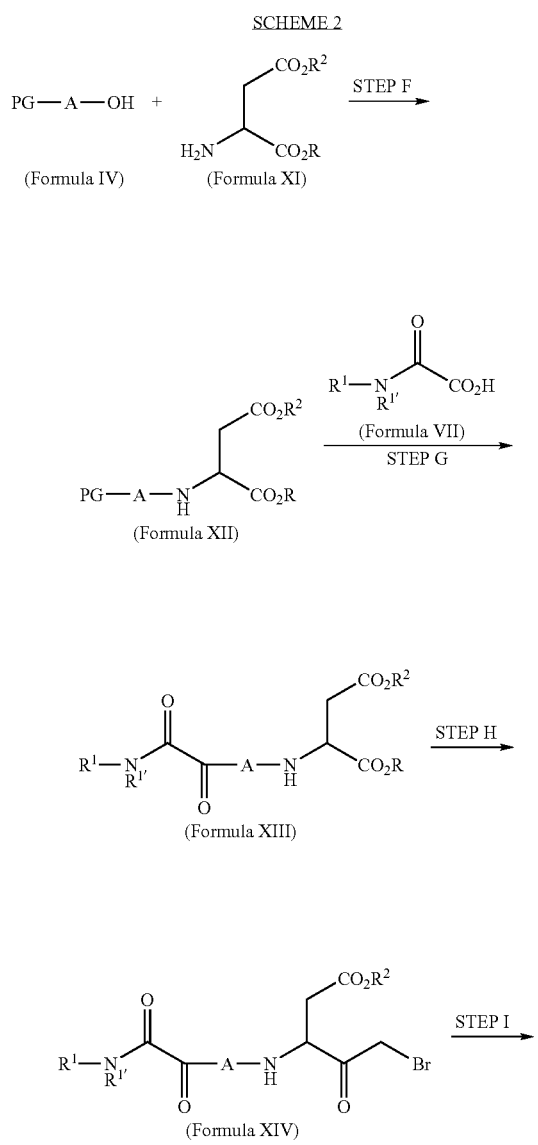

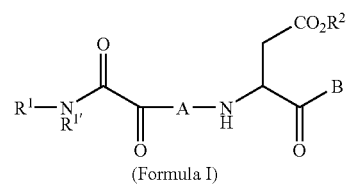

In the above Scheme 2, "PG" stands for an amino protecting group and "A" stands for a natural or unnatural amino acid of formula IIa through IIi, as discussed above. The group R is a carboxyl protecting group such as trimethylsilyl, methyl, allyl, benzyl or tert-butyl.

The coupling reactions carried out under Step F and Step G are performed in the presence of a standard peptide coupling agent as discussed above. In Step G, the amino protecting group must be removed prior to the coupling step. In Step H the alpha-carboxy protecting group R of the compound of Formula XIII is selectively removed and the resulting mono-carboxylic acid treated sequentially with diazomethane and hydrobromic acid to give the alpha-bromoketone of Formula XIV.

In Step I, the bromoketone of Formula XIV is treated with either $R^{15}Z$-H, (aryl)-$CO_2H$, (heteroaryl)-$CO_2H$, or $R^{16}(R^{17})PO_2H$ in the presence of an inorganic base such as potassium carbonate or potassium fluoride in an inert solvent such as dimethyl formamide to give the corresponding compound of Formula I in which B is $CH_2ZR^{15}$, $CH_2OCO$(aryl), $CH_2OCO$(heteroaryl), or $CH_2OPO(R^{16})R^{17}$, respectively. Compounds of Formula I in which B is a fragment of Formula III may also be prepared in a similar fashion. The protecting groups contained in substructures of the Formula XI and A are removed by methods well known in the art. These reactions and removal of some or all of the protecting groups are involved in Step I in the above Scheme 2.

An alternative method for the preparation of compounds of the instant invention of Formula I in which $R^2$ and B are both hydrogen (i.e., Formula Ib) is set forth below in Scheme 3:

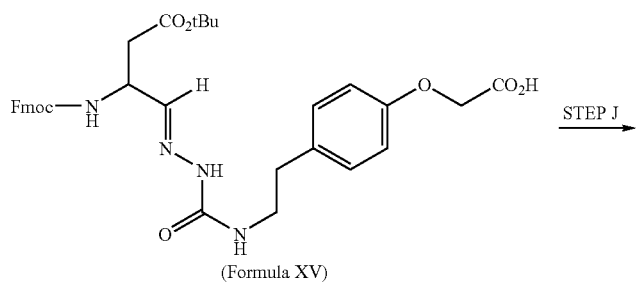

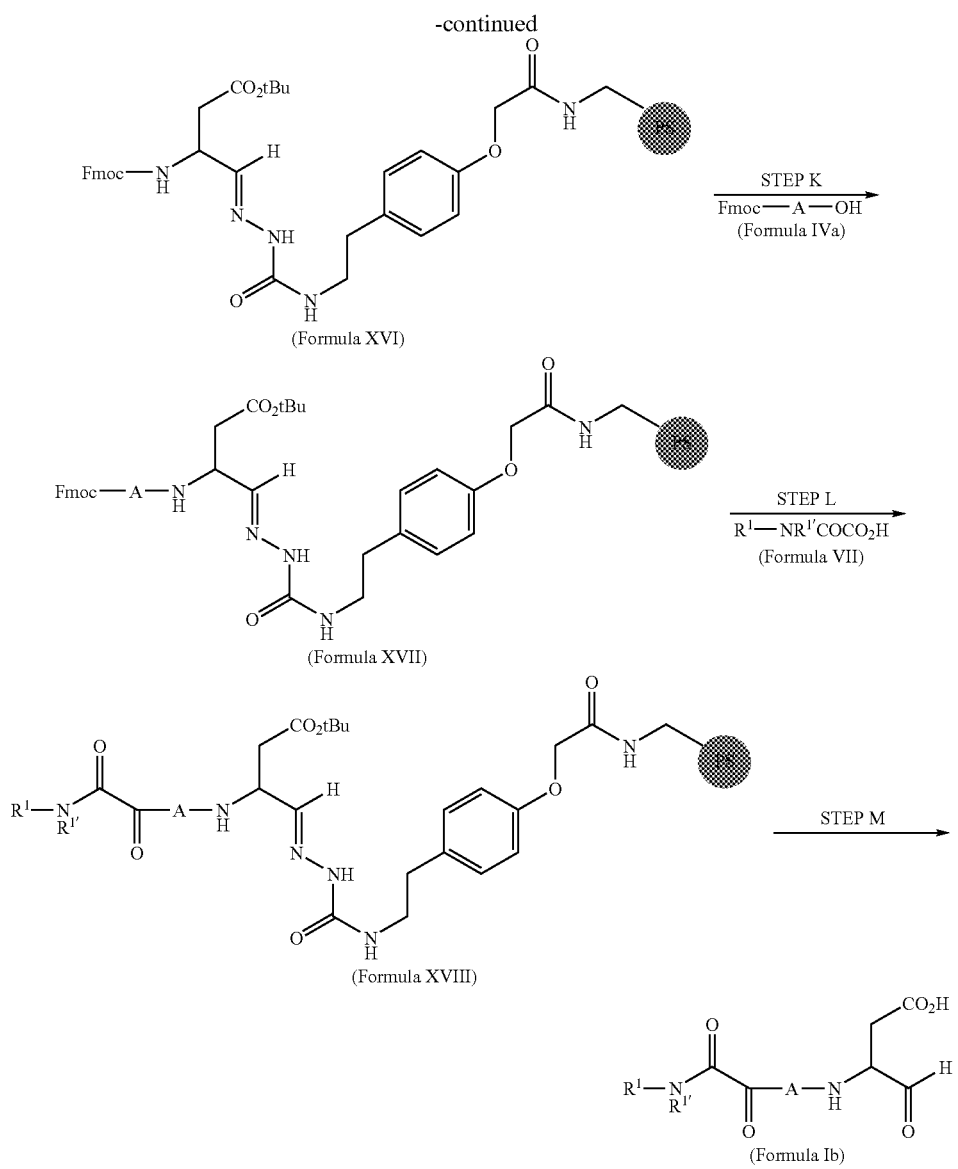

In Scheme 3, Fmoc is the amino protecting group 9-fluorenylmethoxycarbonyl and the shaded circle labeled "PS" represents polystryene resin.

The coupling of the acid of Formula XV to a primary amine on solid support, preferably aminomethyl polystyrene, is carried out using standard peptide coupling agents, preferably using benzotriazolyloxy-tris(N-pyrolidinyl)phosphoniumhexafluorophosphate (pyBOP) in a inert solvent such as dimethylformamide or N-methylpyrrolidone (Step J). After removal of the Fmoc protecting group of XVI by treatment with pyrrolidine-dimethylformamide, the resulting amine is coupled to Fmoc-amino acid of Formula IVa using standard peptide coupling conditions as discussed above (Step K).

In Step L the Fmoc protecting group of the compound of Formula XVII is removed again by treatment with pyrrolidine-dimethylformamide and the resulting amine coupled to the (N-substituted)oxamic acid of Formula VII again using standard peptide coupling conditions as discussed above. The tert-butyl ester of the compound of Formula XVIII is removed by treatment with trifluoroacetic acid-methylene chloride in the presence of a trapping agent such as anisole and the resulting acid cleaved from the solid support by treatment with 37% aqueous formaldehyde/acetic acid/tetrahydrofuran/trifluoroacetic acid, preferably in a ratio of 1/1/5/0.025, to give the aspartyl aldehyde of Formula Ib (Step M).

Pharmaceutical compositions of this invention comprise any of the compounds of the present invention, and pharmaceutically acceptable salts thereof, with any pharmaceutically acceptable carrier, adjuvant or vehicle (hereinafter collectively referred to as "pharmaceutically-acceptable carriers"). Pharmaceutically acceptable carriers, adjuvants and vehicles that may be used in the pharmaceutical compositions of this invention include, but are not limited to, ion exchange, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

The pharmaceutical compositions of this invention may be administered orally, parenterally, by inhalation spray, topically, rectally, nasally, buccally, vaginally or by an implanted reservoir. Oral and parenteral administration are preferred. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyl-dodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds of this invention may be used in combination with either conventional anti-inflammatory agents or with matrix metalloprotease inhibitors, lipoxygenase inhibitors and antagonists of cytokines other than IL-1$\beta$.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexons and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical compositions according to this invention may be comprised of a combination of a compound of Formula I and another therapeutic or prophylactic agent mentioned above.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). As a consequence of their ability to inhibit apoptosis, the present pharmaceutical compositions are also useful for the repopulation of hematopoietic cells of a patient following chemotherapy. Methods of administering an effective amount of the above-described pharmaceutical compositions to mammals, also referred to herein as patients, in need of such treatment (that is, those suffering from inflammatory diseases, autoimmune diseases, neurodegenerative diseases and for the repopulation of hematopoietic cells in cancer patients who have undergone chemotherapy) are another aspect of the instant invention. Finally, as a further consequence of their ability to inhibit apoptosis, the instant pharmaceutical compositions may be used in a method to prolong the viability of organs to be used in transplantations.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative diseases include, for example, amyotrophic lateral sclerosis, Alzheimer's disease, Parkinson's disease, and primary lateral sclerosis. The pharmaceutical compositions of this invention may also be used to promote wound healing. Target diseases associated with harmful, apoptosis, in other words, those associated with ischemic injury, includes myocardial infarction, stroke, and ischemic kidney disease. The pharmaceutical compositions of this invention may also be used to treat infectious diseases, especially those involved with viral infections.

The term "effective amount" refers to dosage levels of the order of from about 0.05 milligrams to about 140 milligrams per kilogram of body weight per day for use in the treatment of the above-indicated conditions (typically about 2.5 milligrams to about 7 grams per patient per day). For example, inflammation may be effectively treated by the administration of from about 0.01 to 50 milligrams of the compound per kilogram of body weight per day (about 0.5 milligrams to about 3.5 grams per patient per day).

The amount of the compounds of Formula I that may be combined with the carrier materials to produce a single dosage form will vary depending upon the host treated and the particular mode of administration. For example, a formulation intended for the oral administration of humans may contain from 0.5 milligrams to 5 grams of a compound of Formula I combined with an appropriate and convenient amount of a pharmaceutically-acceptable carrier which may vary from about 5 to about 95 percent of the total composition. Dosage unit forms will generally contain between from about 1 milligram to about 500 milligrams of an active compound of Formula I.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing prevention or therapy.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cystine protease inhibitors will be evident to those of ordinary skill in the art.

In order that this invention be more fully understood, the following examples are set forth. These examples are for the purpose of illustration only and are not to be construed as limiting the scope of the invention in any way. In the following Examples, proton NMR spectra were obtained at 300 MHz; chemical shifts are quoted downfield from internal tetramethylsilane.

PREPARATION 1

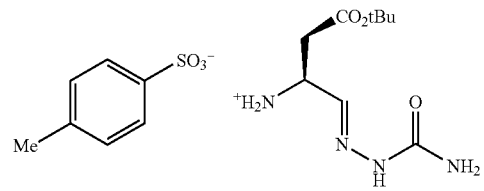

PREPARATION OF (3S)-AMINO-4-OXOBUTANOIC ACID (TERT)-BUTYL ESTER SEMICARBAZONE, p-TOLUENESULFONATE SALT

Part A: N-(Benzyloxycarbonyl)-L-(N'-Methyl-N'-Methoxy)aspartamide β-(tert-Butyl) Ester To a solution of N-(benzyloxycarbonyl)-L-aspartic acid-β-(tert-butyl) ester (14.65 g, 45.3 mmol, Bachem) in CH$_2$Cl$_2$ (150 mL) at 0° C. (ice bath) under a nitrogen atmosphere was added 1-hydroxybenzotriazole hydrate (7.29 g, 47.6 mmol, Aldrich) followed by 1-ethyl-3-(3',3'-dimethyl-1'-aminopropyl)carbodiimide hydrochloride (9.55 g, 49.8 mmol, Sigma). After stirring at 0° C. for 15 min., N,O-dimethylhydroxylamine hydrochloride (5.10 g, 52.3 mmol, Aldrich) and N-methylmorpholine (5.8 mL, 53 mmol, Aldrich) were added. The mixture was allowed to warm to room temperature over 3 hours then stirred at room temperature for 16 hours. The solution was concentrated under vacuum and the residue partitioned between ethyl acetate-5% KHSO$_4$ (200 mL each). The organic phase was washed in turn with 5% KHSO$_4$, saturated sodium bicarbonate and saturated sodium chloride solutions; dried over anhydrous sodium sulfate and evaporated to an oil. The oil was crystallized from hexane to give the title product (16.10 g, 97% yield) as a fluffy white crystalline solid. TLC (ethyl acetate), single spot (UV and PMA): Rf=0.37.

A similar procedure to the one above, starting with 29.3 g of N-(benzyloxycarbonyl)-L-aspartic acid-β-(tert-butyl) ester (2-fold scale up) gave 31.18 g (94% yield) of the title product.

Part B:
(3S)-(Benzyloxycarbonyl)Amino-4-Oxobutanoic Acid (tert)-Butyl Ester Semicarbazone.

To a solution of N-(benzyloxycarbonyl)-L-(N'-methyl-N'-methoxy)aspartamide-β-(tert-butyl) ester (15.50 g, 42.3 mmol) in anhydrous ether (400 mL) at 0° C. (ice bath) under a nitrogen atmosphere was added dropwise to a 1.0 M solution of LiAlH$_4$ in ether (22.0 mL, 22.0 mmol, Aldrich) at such a rate as to keep the reaction solution temperature between 0–5° C. (addition time 15–20 min). After the addition of the lithium aluminum hydride reagent was complete, the mixture was stirred at 0–5° C. for 1 hr, then quenched by the dropwise addition of 0.3 N KHSO$_4$ solution (100 mL). The resultant mixture was transferred to a separatory funnel adding sufficient 5% KHSO$_4$ solution (75 mL) to dissolve the solids. The organic phase was separated and the combined aqueous washes back-extracted with ether (100 mL). The combined ether extracts were washed with saturated NaCl solution, dried over anhydrous sodium sulfate and concentrated in vacuo with minimal heating. TLC (ethyl acetate): streaky spot (UV and PMA): Rf=0.48. TLC (methanol/methylene chloride, 1:9) major spot (UV and PMA): Rf=0.75.

The crude aldehyde was immediately taken up in aqueous ethanol (45 mL water/105 mL alcohol), placed in an ice bath and treated with sodium acetate (3.82 g, 46.6 mmol) and semicarbazide hydrochloride (5.20 g, 46.6 mmol, Aldrich). The mixture was stirred at 0° C. (ice bath) under a nitrogen atmosphere for 3 hrs, allowed to warm to room temperature, and stirred overnight (16 hrs). Most of the ethanol was removed under vacuum and the residue partitioned between ethyl acetate and water (100 mL each). The organic phase was washed sequentially with 5% KHSO$_4$, saturated sodium bicarbonate and saturated sodium chloride solutions; dried over anhydrous sodium sulfate and evaporated to dryness. The crude product of this reaction was combined with that of two similar procedures starting with 15.40 g and 4.625 g of N-(benzyloxycarbonyl)-L-(N'-methyl-N'-methoxy)aspartamide-β-(tert-butyl ester) (total: 35.525 g, 97 mmol) and these combined products were purified by flash chromotagraphy on silica gel eluting with acetone/methylene chloride (3:7) then methanol-acetone-methylene chloride (0.5: 3:7) to give pure title product (27.73 g, 78.5%) as a colorless foam. TLC (MeOH—CH$_2$Cl$_2$, 1:9): single spot (UV and PMA), Rf=0.51.

Part C: (3S)-Amino-4-Oxobutanoic Acid (tert)-Butyl Ester Semicarbazone, p-Toluenesulfonate Salt To a solution of (3S)-(benzyloxycarbonyl)amino-4-oxobutanoic acid (tert)-butyl ester semicarbazone (13.84 g, 38.0 mmol) in absolute ethanol (250 mL) was added 10% Pd/C (1.50 g, Aldrich) and the resulting mixture stirred under an atmosphere of hydrogen (balloon) until TLC (methanol/methylene chloride, 1:9) indicated complete consumption of the starting material (60 min). Note: It is important to follow this reaction closely since the product can be over-reduced. The mixture was filtered though Celite and evaporated to an oil. The oil was chased with methylene chloride (2×75 mL) then with methylene chloride/toluene (1:1, 75 mL) to give the crude amine as a white crystalline solid. TLC (EtOAc-pyridine-AcOH—H$_2$O; 60:20:5:10) single spot (UV and PMA) Rf=0.24. Note: In this TLC system, any over-reduced product will show up immediately below the desired product, Rf=0.18 (PMA only).

The crude amine was taken up in CH$_3$CN (60 mL) and treated with a solution of p-toluenesulfonic acid monohydrate (7.22 g, 38.0 mmol) in acetonitrile (60 mL). The crystalline precipitate was collected, washed with acetonitrile and ether, and air-dried to give the title compound (13.95 g, 92% yield) as a white, crystalline solid.

The optical purity of this material was checked by conversion to the corresponding Mosher amide [1.05 equiv (R)-(-)-α-methoxy-α-(trifluoromethyl)phenylacetyl chloride, 2.1 equivalents of i-Pr$_2$NEt in CH$_2$Cl$_2$, room temperature, 30 min]. The desired product has a doublet at 7.13 ppm (1H, d, J=2.4 Hz, C$\underline{H}$=N) while the corresponding signal for its diastereomer is at 7.07 ppm. The optical purity of the title compound obtained from the above procedure is typically >95:5.

PREPARATION 2

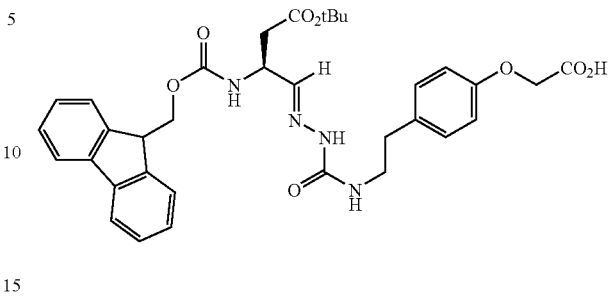

PREPARATION OF (3S)-(9-FLUORENYLMETHOXYCABONYL) AMINO-4-OXOBUTANOIC ACID (TERT)-BUTYL ESTER SEMICARBAZONYL-4-[2'-(4-ETHYL-PHENOXYACEC ACID)]

Part A: 4-[2'-(N-t-Butoxycarbonyl)Aminoethyl]Phenoxyacetic Acid, Methyl Ester To a suspension 4-hydroxy-phenethylamine (7.00 g, 51.1 mmol, Aldrich) in dry dimethylformamide (50 mL) at room temperature under nitrogen was added di-tert-butyl dicarbonate (11.0 g, 50.5 mmol). After stirring at room temperature for 1 hr, the resulting clear solution was treated with methyl bromoacetate (7.5 mL, 79 mmol) and cesium carbonate (17.5 g, 53.7 mmol). After stirring at room temperature for 16 hrs, TLC (Et$_2$O-toluene; 2:8) shows some unalkylated material remained (Rf=0.43) and a second portion of methyl bromoacetate (2.0 mL, 21 mmol) and cesium carbonate (4.5 g, 14 mmol) were added. After stirring for an additional 24 hrs, the mixture was partitioned between EtOAc-water (250 mL each), organic phase washed successively with water (3×), 5% potassium bisulfate and saturated NaCl solutions, dried over anhydrous Na$_2$SO$_4$ and evaporated to dryness. Trituration of the residue with hexane gave 15.87 g of a tan solid. Filtration of the crude product through a pad of silica gel eluting with EtOAc-hexane (2:8) and crystallization from hexane gave the title compound (14.75, 93%) as a white granular, crystalline solid. TLC (Et$_2$O-toluene; 2:8) Rf=0.53.

Part B: 4-(2'-Aminoethyl)Phenoxyacetic Acid, Methyl Ester, Hydrochloride

To a solution 4-[2'-(N-t-butoxycarbonyl)aminoethyl]phenoxyacetic acid, methyl ester (18.31 g, 59.3 mmol) in dioxane (55 mL) at room temperature was added 4.0 N HCl in dioxane (55 mL). After stirring at room temperature for 16 hrs, the mixture was diluted with Et$_2$O, the precipitate collected, washed thoroughly with Et$_2$O and dried in vacuo to give the title compound (14.55 g, 94%) was a fluffy white, crystalline solid.

Part C: 1-tert-Butoxycarbonyl-Semicarbazidyl-4-[2'-(4-Ethyl-Phenoxyacetic Acid)]Methyl Ester.

A solution of t-butyl carbazate (6.60 g, 50 mmol) in dimethylformamide (50 mL) was added dropwise to a solution carbonyldiimidazole (8.10 g, 50 mmol) in dimethylformamide (80 mL) over 40 min at room temperature under nitrogen. After stirring at room temperature for an additional 30 min, 4-(2'-aminoethyl)phenoxyacetic acid, methyl ester, hydrochloride (12.3 g, 50 mmol) was added as a solid in one portion followed by a triethylamine (8.0 mL, 58 mmol) added dropwise over 30 min. After stirring at room temperature for 18 hrs, the mixture was partitioned between EtOAc-water (300 mL each). The organic phase was washed successively with water (3×), 5% potassium bisulfate, saturated sodium bicarbonate, and saturated NaCl solutions, dried over anhydrous $Na_2SO_4$ and evaporated to dryness. Crystallization of the residue from EtOAc-hexane gave the title compound (15.50, 84%) as an off-white crystalline solid. TLC (MeOH—$CH_2Cl_2$; 1:9) Rf=0.45.

Part D: 1-tert-Butoxycarbonyl-Semicarbazidyl-4-[2'-(4-Ethyl-Phenoxyacetic Acid)]

A solution of 1-tert-butoxycarbonyl-semicarbazidyl4-[2'-(4-ethyl-phenoxyacetic acid)]methyl ester (14.68 g, 40 mmol) in dioxane (50 mL) at room temperature under nitrogen was added 1.0 N LiOH solution (50 mL). After stirring at room temperature for 1 hr. the mixture was acidified with conc. HCl and extracted with EtOAc (100 mL). The organic phase was washed with saturated NaCl solution, dried over anhydrous $Na_2SO_4$ and evaporated to a white solid. Recrystallization of the crude product from THF-EtOAc-hexane gave the title compound (13.44, 95%) as a white crystalline solid. TLC (AcOH-MeOH—$CH_2Cl_2$; 1:1:8) Rf=0.31.

Part E:
Semicarbazidyl-4-[2'-(4-Ethyl-Phenoxyacetic Acid)]Hydrochloride

To a solution of 1-tert-butoxycarbonyl-semicarbazidyl-4-[2'-(4-ethyl-phenoxyacetic acid)] (13.43 g, 38.0 mmol) in dioxane (80 mL)-anisole (15 mL) at room temperature was added 4.0 N HCl in dioxane (35 mL). After stirring at room temperature for 18 hrs, additional 4.0 N HCl in dioxane (15 mL) was added. After an additional 6 hrs, the precipitate was collected, washed thoroughly with dioxane then $Et_2O$ and dried in vacuo to give the title compound (11.67 g, 100%) was a white, crystalline solid.

Part F: N-(9-Fluorenylmethoxycarbonyl)-L-(N'-Methyl-N'-Methoxy)aspartamide β-(tert-Butyl) Ester To a solution of N-(9-fluorenylmethoxycarbonyl)-L-aspartic acid-β-(tert-butyl) ester (16.48 g, 40 mmol) in $CH_2Cl_2$ (80 mL)-tetrahydrofuran (20 mL) at 0° C. (ice bath) under a nitrogen atmosphere was added 1-hydroxybenzotriazole hydrate (7.12 g, 46.5 mmol) followed by 1-ethyl-3-(3',3'-dimethyl-1'-aminopropyl)carbodiimide hydrochloride (9.20 g, 48 mmol). After stirring at 0° C. for 15 min., N,O-dimethylhydroxylamine hydrochloride (4.68 g, 48 mmol) and N-methylmorpholine (5.2 mL, 47 mmol) were added. The mixture was allowed to warm to room temperature over 2 hours then stirred at room temperature for 16 hours. The solution was concentrated under vacuum and the residue partitioned between ethyl acetate-5% $KHSO_4$ (200 mL each). The organic phase was washed successively with 5% $KHSO_4$, saturated sodium bicarbonate and saturated sodium chloride solutions; dried over anhydrous sodium sulfate and evaporated to an oil. Purification of the crude product by flash chromatography on silica gel eluting with EtOAc-hexane (30:70 then 35:65) gave the title product (17.75 g, 98% yield) as a colorless foam. TLC (EtOAc-hexane; 1:1) Rf=0.35.

Part G: (3S)-(9-Fluorenylmethoxycabonyl)Amino-4-Oxobutanoic Acid (tert)-Butyl Ester Semicarbazo-nyl-4-[2'-(4-Ethyl-Phenoxyacetic Acid)]

To a solution of N-(9-fluorenylmethoxycarbonyl)-L-(N'-methyl-N'-methoxy)aspartamide-β-(tert-butyl)ester (13.20 g, 29 mmol) in anhydrous ether (250 mL) at 0° C. (ice bath) under a nitrogen atmosphere was added dropwise to a 1.0 M solution of $LiAlH_4$ in ether (14.5 mL, 14.5 mmol) at such a rate as to keep the reaction solution temperature between 0–5° C. (addition time 15–20 min). After the addition of the lithium aluminum hydride reagent was complete, the mixture was stirred at 0–5° C. for 1 hr. then quenched by the dropwise addition of 0.3 N $KHSO_4$ solution (100 mL). After adding sufficient 0.3 N $KHSO_4$ solution to dissolve most of the inorganic salts, the mixture was transferred to a separatory funnel. The organic phase was separated and the aqueous phase back-extracted with ether (100 mL). The combined ether extracts were washed with saturated NaCl solution, dried over anhydrous sodium sulfate and concentrated in vacuo with minimal heating. TLC (EtOAc-hexane): Rf=0.40.

The crude aldehyde was immediately taken up in ethanol (105 mL)-water(45 mL)-tetrahydrofuran(75 mL), placed in an ice bath and treated with sodium acetate (3.20 g, 39 mmol) and semicarbazidyl-4-[2'-(4-ethyl-phenoxyacetic acid)]hydrochloride (8.65 g, 30 mmol). The mixture was stirred at 0° C. (ice bath) under a nitrogen atmosphere for 3 hrs, allowed to warm to room temperature, and stirred overnight (16 hrs). The mixture was concentrated on a rotovap, diluted with water and resulting precipitate collected by suction. The material was dried in vacuo to give 18.36 g of crude product as a white solid. The crude product of this reaction was combined with that of a smaller scale reaction (6.34 g) starting with 4.55 g (10 mmol) of N-(9-fluorenylmethoxycarbonyl)-L-(N'-methyl-N'-methoxy)aspartamide-β-(tert-butyl ester) and partitioned between ethyl acetate-tetrahydrofuran(1:1) and 5% $KHSO_4$. The organic phase was washed with 5% $KHSO_4$ and saturated sodium chloride solutions, dried over anhydrous sodium sulfate and evaporated to dryness. The residue was purified by filtration through a pad of silica gel eluting with terahydrofuran/methylene chloride (1:1). The combined product-containing fractions were evaporated to dryness and recrystallized from tetrahydrofuran-$Et_2O$ to give pure title product (17.01 g, 69%) as a white solid. TLC (AcOH-MeOH—$CH_2Cl_2$, 1:1:40): Rf=0.19.

PREPARATION 3

ASSAY FOR INHIBITION OF ICE/CED-3 PROTEASE FAMILY ACTIVITY

A. Determination of $IC_{50}$ Values

Fluorescence enzyme assays detecting the activity of the compounds of Formula I utilizing the recombinant ICE and CPP32 enzymes are performed essentially according to Thornberry et al. (*Nature*, 356:768:774 (1992)) and Nicholson et al. (*Nature*, 376:37–43 (1995)) respectively, (herein incorporated by reference) in 96 well microtiter plates. The substrate is Acetyl-Tyr-Val-Ala-Asp-amino-4-methylcoumarin (AMC) for the ICE assay and Acetyl-Asp-Glu-Val-Asp-amino-4-methylcoumarin for the CPP32, Mch2, Mch3 and Mch5 assays. Enzyme reactions are run in ICE buffer (25 mM HEPES, 1 mM EDTA, 0.1% CHAPS, 10% sucrose, pH 7.5) containing 2 mM DTT at room temperature in duplicate. The assays are performed by mixing the following components:

- 50 μL ICE, Mch2, Mch5, CPP32 (18.8, 38, 8.1 and 0.153 nM concentrations, respectively) or Mch3 (1 unit) enzyme in ICE buffer containing either 8.0 (ICE, Mch2, Mch3, CPP32) or 20 (Mch5) mM DTT;
- 50 μL compound of Formula I or ICE buffer (control); and
- 100 μL of 20 μM substrate.

The enzyme and the compound of Formula I to be assayed are allowed to preincubate in the microtitre plate wells for 30 minutes at room temperature prior to the addition of substrate to initiate the reaction. Fluorescent AMC product formation is monitored for one hour at room temperature by measuring the fluorescence emission at 460 nm using an excitation wavelength of 360 nm. The fluorescence change in duplicate (control) wells are averaged and the mean values are plotted as a function of inhibitor concentration to determine the inhibitor concentration producing 50% inhibition ($IC_{50}$).

The results of this assay are set forth below in Table 1. The reference compound for this assay was Cbz-ValAlaAsp-H and the values are denoted in Table 1 as "Reference".

TABLE 1

| Example No. | mICE $IC_{50}$ (μM) | CPP32 $IC_{50}$ (μM) | MCH-2 $IC_{50}$ (μM) | MCH-3 $IC_{50}$ (μM) | MCH-5 $IC_{50}$ (μM) |
|---|---|---|---|---|---|
| 1 | 0.027 | 0.010 | 1.50 | 0.267 | 0.179 |
| 112 | 0.059 | 1.38 | 3.53 | 1.13 | 0.322 |
| reference | 0.064 | 47.0 | >10 | >10 | 2.96 |

B. Determination of the Dissociation Constant Ki and Irreversible Rate Constant $k_3$ for Irreversible Inhibitors For the irreversible inhibition of a ICE/ced-3 Family Protease enzyme with a competitive irreversible inhibitor; using the model represented by the following formulas:

The product formation at time t may be expressed as:

$$[P]_t = [E]^T \left(\frac{[S]K_i}{[I]K_s}\right)\left(\frac{k_s}{k_3}\right)\left[1 - e^{-k_3 t / (1 + \frac{K_i}{[I]}(1 + \frac{[S]}{K_s}))}\right] \quad \text{Equation 1}$$

where E, I, EI and E-I denote the active enzyme, inhibitor, non-covalent enzyme-inhibitor complex and covalent enzyme-inhibitor adduct, respectively. The $K_i$ value is the overall dissociation constant of the reversible binding steps, and $k_3$ is the irreversible rate constant. The [S] and $K_s$ values are the substate concentration and dissociation constant of the substrate bound to the enzyme, respectively. $[E]^T$ is the total enzyme concentration.

The above equations are used to determine the $K_i$ and $k_3$ values of a given inhibitor bound to a ICE/ced-3 family protease. Thus, a continuous assay is run for sixty minutes at various concentrations of the inhibitor and the substrate. The assay is formulated essentially the same as described above for generating the data in Table 1, except that the reaction is initiated by adding the enzyme to the substrate-inhibitor mixture. The $K_i$ and $k_3$ values are obtained by simulating the product AMC formation as a function of time according to Equation 1.

The results of this second assay are set forth below in Table 2. The reference compound for this assay was Cbz-ValAlaAsp-CH$_2$F and the values are denoted in Table 2 as "Reference". The $K_i$ values in Table 2 are in micromolar (μM). The $k_3/K_i$ values are in moles$^{-1}$ seconds$^{-1}$ ($M^{-1}s^{-}$).

TABLE 2

| | mICE | | CPP32 | | MCH-2 | | MCH-5 | |
|---|---|---|---|---|---|---|---|---|
| Ex. | Ki | $k_3$/Ki | Ki | $k_3$/Ki | Ki | $k_3$/Ki | Ki | $k_3$/Ki |
| 3 | 0.0018 | 2,170,000 | 0.032 | 413,000 | 0.017 | 199,000 | 0.0013 | 1,160,000 |
| 4 | 0.0061 | 1,050,000 | 0.014 | 740,000 | 0.009 | 234,000 | 0.0040 | 119,000 |
| 5 | 0.0074 | 1,300,000 | 0.041 | 492,000 | 0.025 | 50,000 | 0.0050 | 311,000 |
| 6 | 0.0088 | 879,000 | 0.039 | 340,000 | 0.042 | 37,400 | 0.0053 | 189,000 |
| 7 | 0.0057 | 893,000 | 0.046 | 289,000 | 0.016 | 143,000 | 0.0037 | 448,000 |
| 8 | 0.0039 | 1,220,000 | 0.026 | 203,000 | 0.254 | 3,250 | 0.029 | 0 |
| 9 | 0.128 | 82,100 | 0.059 | 43,600 | 0.336 | 0 | 0.453 | 0 |
| 10 | 0.0065 | 1,400,000 | 0.019 | 529,000 | 0.011 | 165,000 | 0.0054 | 847,000 |
| 11 | 0.0050 | 2,950,000 | 0.025 | 876,000 | 0.011 | 222,000 | 0.0013 | 2,450,000 |
| 12 | 0.0072 | 1,070,000 | 0.064 | 294,000 | 0.095 | 13,300 | 0.012 | 60,300 |
| 13 | 0.024 | 532,000 | 0.067 | 264,000 | 0.096 | 12,800 | 0.023 | 88,800 |
| 15 | 0.0061 | 1,840,000 | 0.042 | 286,000 | 0.037 | 69,100 | 0.0057 | 625,000 |
| 16 | 0.0095 | 1,051,000 | 0.035 | 283,000 | 0.043 | 40,900 | 0.0081 | 112,000 |
| 18 | 0.033 | 254,000 | 0.046 | 180,000 | 0.020 | 83,700 | 0.010 | 177,000 |
| 19 | 0.016 | 825,000 | 0.061 | 167,000 | 0.033 | 63,000 | 0.012 | 286,000 |
| 28 | 0.046 | 167,000 | 0.109 | 55,600 | 0.042 | 35,000 | 0.0058 | 37,800 |
| 29 | 0.038 | 259,000 | 0.015 | 388,000 | 0.009 | 219,000 | 0.017 | 125,000 |
| 30 | 0.022 | 345,000 | 0.042 | 243,000 | 0.025 | 317,000 | 0.024 | 207,000 |
| 31 | 0.031 | 442,000 | 0.060 | 67,700 | 0.071 | 54,900 | 0.045 | 119,000 |
| 32 | 0.098 | 159,000 | 0.034 | 327,000 | 0.016 | 275,000 | 0.010 | 282,000 |
| 33 | 0.0056 | 2,590,000 | 0.061 | 158,000 | 0.016 | 335,000 | 0.0097 | 1,260,000 |
| 34 | 0.0099 | 1,160,000 | 0.043 | 187,000 | 0.011 | 214,000 | 0.0042 | 936,000 |
| 35 | 0.035 | 191,000 | 0.022 | 245,000 | 0.011 | 186,000 | 0.023 | 82,700 |
| 36 | 0.231 | 18,800 | 1.11 | 4,280 | 0.381 | 2,300 | 0.144 | 9,830 |
| 37 | 0.465 | 43,300 | 0.078 | 142,000 | 0.013 | 191,000 | 0.083 | 39,100 |
| 38 | 0.152 | 90,100 | 0.013 | 942,000 | 0.006 | 360,000 | 0.0060 | 337,000 |
| 39 | 0.116 | 172,000 | 0.202 | 68,900 | 0.023 | 129,000 | 0.040 | 155,000 |

TABLE 2-continued

| | mICE | | CPP32 | | MCH-2 | | MCH-5 | |
|---|---|---|---|---|---|---|---|---|
| Ex. | Ki | $k_3$/Ki | Ki | $k_3$/Ki | Ki | $k_3$/Ki | Ki | $k_3$/Ki |
| 40 | 0.045 | 195,000 | 0.063 | 221,000 | 0.015 | 192,000 | 0.010 | 248,000 |
| 41 | 0.140 | 103,000 | 0.035 | 162,000 | 0.011 | 247,000 | 0.027 | 179,000 |
| 42 | 0.0070 | 1,940,000 | 0.021 | 842,000 | 0.0070 | 745,000 | 0.0046 | 1,630,000 |
| 43 | 0.013 | 956,000 | 0.052 | 268,000 | 0.0090 | 424,000 | 0.0036 | 2,300,000 |
| 44 | 1.45 | 11,700 | 1.28 | 22,700 | 0.142 | 18,600 | 0.462 | 18,700 |
| 45 | 0.019 | 369,000 | 0.112 | 100,000 | 0.019 | 98,500 | 0.0080 | 441,000 |
| 46 | 0.0053 | 1,503,000 | 0.052 | 78,600 | 0.0073 | 202,000 | 0.0044 | 933,000 |
| 47 | 0.014 | 625,000 | 0.024 | 395,000 | 0.011 | 484,000 | 0.0087 | 589,000 |
| 48 | 0.011 | 905,000 | 0.069 | 139,000 | 0.022 | 132,000 | 0.0041 | 1,150,000 |
| 49 | 0.0014 | 17,600,000 | 0.043 | 260,000 | 0.010 | 264,000 | 0.0040 | 1,920,000 |
| 50 | 0.640 | 22,000 | 0.129 | 118,000 | 0.072 | 64,100 | 0.074 | 46,200 |
| 51 | 1.01 | 13,900 | 0.370 | 54,300 | 0.070 | 42,800 | 0.083 | 23,100 |
| 52 | 0.340 | 59,100 | 0.029 | 600,000 | 0.020 | 244,000 | 0.062 | 203,000 |
| 53 | 0.462 | 27,600 | 0.134 | 149,000 | 0.042 | 124,000 | 0.077 | 50,400 |
| 54 | 0.348 | 46,000 | 0.409 | 20,500 | 0.120 | 21,100 | 0.080 | 18,700 |
| 55 | 0.0061 | 2,020,000 | 0.013 | 1,174,000 | 0.0063 | 655,000 | 0.0026 | 2,140,000 |
| 56 | 0.0053 | 2,032,000 | 0.096 | 137,000 | 0.025 | 97,500 | 0.0025 | 1,790,000 |
| 57 | 0.0053 | 1,980,000 | 0.044 | 564,000 | 0.013 | 373,000 | 0.0021 | 2,330,000 |
| 58 | 0.054 | 278,000 | 0.043 | 323,000 | 0.018 | 281,000 | 0.0071 | 396,000 |
| 59 | 0.045 | 211,000 | 0.071 | 104,000 | 0.015 | 308,000 | 0.0055 | 1,340,000 |
| 60 | 0.026 | 289,000 | 0.058 | 189,000 | 0.049 | 146,000 | 0.014 | 306,000 |
| 61 | 0.023 | 315,000 | 0.069 | 157,000 | 0.019 | 120,000 | 0.038 | 71,800 |
| 62 | 1.02 | 16,900 | 0.101 | 149,000 | 0.023 | 126,000 | 0.090 | 21,200 |
| 63 | 0.064 | 87,800 | 0.213 | 48,000 | 0.068 | 52,600 | 0.085 | 21,400 |
| 64 | 0.047 | 242,000 | 0.038 | 243,000 | 0.0074 | 445,000 | 0.0055 | 643,000 |
| 65 | 0.108 | 126,000 | 0.050 | 165,000 | 0.022 | 143,000 | 0.025 | 92,600 |
| 66 | 0.025 | 339,000 | 0.028 | 478,000 | 0.019 | 212,000 | 0.013 | 170,000 |
| 72 | 0.012 | 1,230,000 | 0.094 | 169,000 | 0.026 | 131,000 | 0.0081 | 667,000 |
| 74 | 0.303 | 36,300 | 0.161 | 78,300 | 0.078 | 66,200 | 0.070 | 46,300 |
| 75 | 0.013 | 1,270,000 | 0.105 | 67,600 | 0.034 | 28,200 | 0.0040 | 551,000 |
| 76 | 0.019 | 537,000 | 0.085 | 62,900 | 0.235 | 6,960 | 0.022 | 30,200 |
| 77 | 0.023 | 323,000 | 1.34 | 3,430 | 0.544 | 5,850 | 0.013 | 154,000 |
| 78 | 0.0030 | 1,970,000 | 0.103 | 44,500 | 0.040 | 33,600 | 0.0040 | 617,000 |
| 79 | 0.0060 | 1,800,000 | 0.405 | 21,000 | 0.125 | 16,600 | 0.0050 | 472,000 |
| 80 | 0.182 | 77,100 | 0.515 | 13,400 | 0.175 | 12,600 | 0.162 | 16,600 |
| 81 | 0.054 | 201,000 | 0.882 | 5,380 | 1.15 | 1,430 | 0.036 | 48,600 |
| 82 | 0.0070 | 1,490,000 | 0.389 | 36,000 | 0.100 | 25,500 | 0.0050 | 598,000 |
| 83 | 0.135 | 127,000 | 0.251 | 25,400 | 0.085 | 31,700 | 0.030 | 65,300 |
| 84 | 0.043 | 344,000 | 0.367 | 54,800 | 0.082 | 25,300 | 0.024 | 105,000 |
| 88 | 0.359 | 27,400 | 3.13 | 3,130 | 1.43 | 1,840 | 0.128 | 20,800 |
| 89 | 0.052 | 184,000 | 1.51 | 6,330 | 0.152 | 10,700 | 0.040 | 59,900 |
| 90 | 0.147 | 58,500 | 2.27 | 5,560 | 0.221 | 11,200 | 0.040 | 49,600 |
| 91 | 0.016 | 906,000 | 0.758 | 36,300 | 0.059 | 121,000 | 0.015 | 338,000 |
| 92 | 0.011 | 1,044,000 | 0.175 | 57,400 | 0.012 | 261,000 | 0.0060 | 41,000 |
| 93 | 0.0060 | 2,052,000 | 0.353 | 27,700 | 0.041 | 112,000 | 0.0030 | 1,165,000 |
| 94 | 0.024 | 657,000 | 1.11 | 11,200 | 0.059 | 50,000 | 0.012 | 155,000 |
| 95 | 0.0060 | 2,068,000 | 1.09 | 10,800 | 0.088 | 61,500 | 0.0030 | 2,680,000 |
| 100 | 0.206 | 36,000 | 2.25 | 9,850 | 0.188 | 11,600 | 0.157 | 19,500 |
| 101 | 22.6 | 912 | 26.1 | 511 | 0.641 | 5,580 | 1.55 | 1,140 |
| 102 | 0.014 | 1,220,000 | 0.127 | 153,000 | 0.022 | 170,000 | 0.010 | 389,000 |
| 103 | 0.0053 | 2,570,000 | 0.060 | 149,000 | 0.017 | 175,000 | 0.0047 | 1,834,000 |
| 104 | 0.0045 | 2,320,000 | 0.084 | 98,600 | 0.013 | 160,000 | 0.0052 | 456,000 |
| 105 | 0.0084 | 1,540,000 | 0.122 | 96,300 | 0.026 | 161,000 | 0.052 | 234,000 |
| 106 | 0.0090 | 1,080,000 | 0.063 | 276,000 | 0.019 | 230,000 | 0.0034 | 1,305,000 |
| 107 | 0.0070 | 1,260,000 | 0.510 | 42,300 | 0.020 | 137,000 | 0.0040 | 1,026,000 |
| 108 | 0.0048 | 2,680,000 | 0.102 | 62,900 | 0.0080 | 1,083,000 | 0.0019 | 1,830,000 |
| 109 | 0.025 | 767,000 | 0.193 | 70,600 | 0.232 | 8,230 | 0.034 | 51,300 |
| 110A | 0.018 | 835,000 | 0.472 | 21,500 | 0.070 | 20,800 | 0.0074 | 169,000 |
| 110B | 0.017 | 1,010,000 | 0.104 | 81,900 | 0.080 | 41,700 | 0.0078 | 180,000 |
| refer. | 0.015 | 214,000 | 0.820 | 12,200 | 0.594 | 2,950 | 0.018 | 83,300 |

The following are examples of compounds of the invention.

EXAMPLE 1

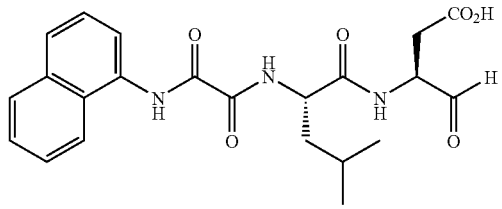

(3S)-3-[N-(N'-(1-Naphthyl)Oxamyl)Leucinyl]
Amino-4-Oxobutanoic Acid

Part A: N-(1-Naphthyl)Oxamic Acid

To a solution of 1-aminonaphthylene (1.43 g, 10 mmol) and triethylamine (1.5 mL, 10.8 mmol) in $CH_2Cl_2$ (10 mL) at 0° C. (ice bath) under nitrogen was added dropwise a solution of methyl oxalyl chloride (1.0 mL, 10.9 mmol) in $CH_2Cl_2$ (5 mL). When the addition was complete, the mixture was allowed to come to room temperature and stirred for 1 hr. The mixture was concentrated and the residue partitioned between EtOAc-5% $KHSO_4$. The organic phase was washed with 5% $KHSO_4$ and saturated NaCl solutions, dried over anhydrous $Na_2SO_4$ and evaporated to a pink solid. Recrystallization of the crude product from toluene-hexane gave the N-(1-naphthyl)oxamic acid methyl ester (2.066 g, 90%) as a pink crystalline solid. TLC(EtOAc-hexane) Rf=0.6.

The methyl ester (1.97 g, 8.6 mmol) was taken up in dioxane (10 mL) and treated with 1.0 N LiOH solution (10 mL, 10 mmol) and stirred at room temperature for 1 hr. The mixture was acidified with conc. HCl and extracted with EtOAc. The extract was washed with saturated NaCl solution, dried over anhydrous $Na_2SO_4$ and evaporated to a pink solid. Recrystallization of the crude product from EtOAc-hexane gave the title compound (1.712 g, 85%) as a pink crystalline solid. TLC(AcOH-MeOH—$CH_2Cl_2$; 1:1:20) Rf=0.06.

Part B: (3S)-3-[(N-Benzyloxycarbonyl)Leucinyl]
Amino-4-Oxobutanoic Acid (tert)-Butyl Ester Semicarbazone To a solution of (N-benzyloxycarbonyl)leucine N-hydroxysuccinimde ester (1.81 g, 5.0 mmol) in $CH_2Cl_2$ (30 mL) at room temperature under nitrogen was added (3S)-amino-4-oxobutanoic acid (tert)-butyl ester semicarbazone, p-toluenesulfonate salt (2.58 g, 6.4 mmol) followed by diisopropyl ethylamine (1.2 mL, 6.9 mmol). After stirring at room temperature for 16 hrs, the mixture was concentrated and the residue partitioned between EtOAc-5% $KHSO_4$. The organic phase was washed with 5% $KHSO_4$, saturated $NaHCO_3$ and saturated NaCl solutions, dried over anhydrous $Na_2SO_4$ and evaporated to give the title compound (2.798 g) as a pale yellow foam. TLC(MeOH—$CH_2Cl_2$; 1:9) Rf=0.52.

Part C: (3S)-3-(Leucinyl)Amino-4-Oxobutanoic Acid (tert)-Butyl Ester Semicarbazone To a solution of crude (3S)-[(N-benzyloxycarbonyl)leucinyl]amino-4-oxobutanoic acid (tert)-butyl ester semicarbazone (2.798 g, ca. 5.0 mmol) in absolute EtOH (40 mL) was added 10% Pd—C (0.40 g) and resulting mixture stirred under a hydrogen atmosphere (balloon) for 1.5 hrs. The mixture was filtered through Celite washing the filter cake with $CH_2Cl_2$ and the combined filtrates evaporated to dryness. The residue was chased with $CH_2Cl_2$ (2×20 mL) to give the title product (2.113 g) as a colorless foam. TLC (MeOH—$CH_2Cl_2$; 1:9) Rf=0.23.

Part D: (3S)-3-[N-(N'-(1-Naphthyl)Oxamyl)Leucinyl]Amino-4-Oxobutanoic Acid (tert)-Butyl Ester Semicarbazone To a solution of N-(1-naphthyl)oxamic acid (0.095 g, 0.44 mmol) and (3S)-3-(leucinyl)amino-4-oxobutanoic acid (tert)-butyl ester semicarbazone (0.180 g, ca 0.41 mmol) in N-methylpyrrolidone(1.0 mL)-$CH_2Cl_2$(1.0 mL) at 0° C. (ice bath) under nitrogen was added hydroxybenzotriazole hydrate (0.100 g) followed by 1-ethyl-3-(3',3'-dimethyl-1'-aminopropyl)carbodiimide hydrochloride (0.100 g, 0.52 mmol). After stirring at 0° C. for 2 hrs and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to a solid. The solid residue was triturated with $Et_2O$ to give the title compound (0.231 g, 97%) as an off-white solid. TLC (MeOH—$CH_2Cl_2$; 5:95) Rf=0.32.

Part E: (3S)-3-[N-(N'-(1-Naphthyl)Oxamyl)Leucinyl]Amino-4-Oxobutanoic Acid Semicarbazone To a suspension of (3S)-3-[N-(N'-(1-naphthyl)oxamyl) leucinyl]amino-4-oxobutanoic acid (tert)-butyl ester semicarbazone (0.212 g, 0.39 mmol) in $CH_2Cl_2$(2.0 mL)-anisole (0.5 mL) at room temperature under nitrogen was added trifluoroacetic acid (2.0 mL). The resulting clear solution was stirred at room temperature for 3 hrs, evaporated to dryness and chased with toluene-$CH_2Cl_2$ (1:1). The residue was triturated with $Et_2O$ to give the title compound (0.181 g, 95%) as an off-white solid. TLC(AcOH-MeOH—$CH_2Cl_2$; 1:1:20) Rf=0.16.

Part F: (3 S)-3-[N-(N'-(1-Naphthyl)Oxamyl)Leucinyl]Amino-4-Oxobutanoic Acid

A suspension of (3S)-3-[N-(N'-(1-naphthyl)oxamyl)leucinyl]amino-4-oxobutanoic acid semicarbazone (0.173 g, 0.36 mmol) in 37% aqueous formaldehyde(1.0 mL)-acetic acid (1.0 mL)-methanol(3.0 mL) was stirred at room temperature under nitrogen for 18 hrs. The resulting clear solution was diluted with water and the resulting white precipitate collected by suction and washed with water. The combined aqueous filtrate was extracted with EtOAc. The extract was washed with water and saturated NaCl solution, dried over anhydrous $Na_2SO_4$ and evaporated to a glass. This was combined with the solid which was filtered from the aqueous mixture, taken up in $CH_2Cl_2$, filtered through Celite and evaporated to dryness. The crude product was purified by dissolving the residue in $CH_2Cl_2$ and precipitating with $Et_2O$-hexane. The precipitate was collected by suction to give the title compound (0.129 g, 84%) as a white solid.

TLC(AcOH-MeOH—CH$_2$Cl$_2$; 1:1:20) Rf=0.22. MS(ES) for C$_{22}$H$_{25}$N$_3$O$_6$ (MW 427.46): positive 450(M+Na); negative 426(M–H)

EXAMPLE 2

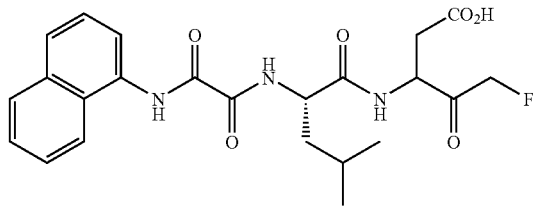

(3RS)-3-[N-(N'-(1-Naphthyl)Oxamyl)Leucinyl] Amino-5-Fluoro-4-Oxopentanoic Acid

Part A: (3RS,4RS)-3-[(N-Benzyloxycarbonyl)Leucinyl]Amino-5-Fluoro-4-Hydroxypentanoic Acid, tert-Butyl Ester To a solution of (3RS,4RS)-3-amino-5-fluoro-4-hydroxypentanoic acid, tert-butyl ester (0.230 g, 1.1 mmol, prepared as described in *Tetrahedron Letters* 1994, 35, 9693–9696) in CH$_2$Cl$_2$ (2.0 mL) at room temperature under nitrogen was added (N-benzyloxycarbonyl)leucine, N-hydroxysuccinimde ester (0.402 g, 1.1 mmol). After stirring at room temperature for 16 hrs, the mixture was evaporated to dryness and the residue purified by flash chromatography on silica gel eluting with EtOAc-hexane (1:2) to give the title compound (0.332 g, 66%) as a colorless, viscous oil. TLC (EtOAc-hexane; 2:1) Rf=0.51.

Part B: (3RS,4RS)-3-(Leucinyl)Amino-5-Fluoro-4-Hydroxypentanoic Acid, tert-Butyl Ester, p-Toluenesulfonate Salt To a solution of (3RS,4RS)-3-[(N-benzyloxycarbonyl)leucinyl]amino-5-fluoro-4-hydroxypentanoic acid, tert-butyl ester (0.332 g, 0.734 mmol) in MeOH (100 mL) was added p-toluenesulsufonic acid hydrate (0.140 g, 0.737 mmol) and 10% Pd—C (0.033 g) and resulting mixture stirred under a hydrogen atmosphere (balloon) for 2 hrs. The mixture was filtered through Celite washing the filter cake with CH$_2$Cl$_2$ and the combined filtrates evaporated to dryness. The residue was chased with CH$_2$Cl$_2$ to give the title product (0.371 g) as a colorless foam.

Part C: (3RS,4RS)-3-[N-(N'-(1-Naphthyl)Oxamyl) Leucinyl]Amino-5-Fluoro-4-Hydroxypentanoic Acid, tert-Butyl Ester To a solution of N-(1-naphthyl)oxamic acid (0.161 g, 0.749 mmol, see Example 1, Part A) in N-methylpyrrolidone (1.5 mL)-CH$_2$Cl$_2$(1.5 mL) at room temperature under nitrogen was added O-(7-azabenzotriazol-1-yl)-N,N,N',N'-tetramethyluronium hexafluorophate (0.313 g, 0.823 mmol). After stirring for 0.5 hrs, the mixture was treated with a solution of (3RS,4RS)-3-(leucinyl)amino-5-fluoro-4-hydroxypentanoic acid, tert-butyl ester, p-toluenesulfonate salt (0.371 g, 0.749 mmol) and diisopropylethylamine (0.39 mL, 2.25 mmol) in N-methylpyrrolidone(2.0 mL)-CH$_2$Cl$_2$(2.0 mL). After stirring at room temperature for 16 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. The residue was purified by flash chromatography on silica gel eluting with EtOAc-hexane (1:1) to give the title compound (0.213 g, 55%) as a colorless foam. TLC(Et$_2$O—CH$_2$Cl$_2$-hexane; 2:1:2, 2 developments) Rf=0.12.

Part D: (3RS)-3-[N-(N'-(1-Naphthyl)Oxamyl)Leucinyl]Amino-5-Fluoro-4-Oxopentanoic Acid, tert-Butyl Ester To a solution of (3RS,4RS)-3-[N-(N'-(1-naphthyl)oxamyl)leucinyl]amino-5-fluoro-4-hydroxypentanoic acid, tert-butyl ester (0.163 g, 0.315 mmol) in CH$_2$Cl$_2$ (3.0 mL) at room temperature was added Dess-Martin periodinane (0.160 g, 0.378 mmol). After stirring at room temperature for 0.5 hrs, the mixture was diluted with EtOAc and washed with dilute Na$_2$S$_2$O$_3$, saturated NaHCO$_3$ and saturated NaCl solutions, dried over anhydrous Na$_2$SO$_4$ and evaporated to dryness. The residue was purified by flash chromatography on silica gel eluting with EtOAc-hexane (1:3) to give the title compound (0.155 g, 95%) as a white solid. TLC(Et$_2$O—CH$_2$Cl$_2$-hexane; 2:1:2, 2 developments) Rf=0.35. MS(ES) for C$_{27}$H$_{34}$FN$_3$O$_6$ (MW 515.57): positive 538(M+Na); negative 514(M–H).

Part E: (3RS)-3-[N-(N'-(1-Naphthyl)Oxamyl)Leucinyl]Amino-5-Fluoro-4-Oxopentanoic Acid To a solution of (3RS)-3-[N-(N'-(1-naphthyl)oxamyl) leucinyl]amino-5-fluoro-4-oxopentanoic Acid, tert-butyl ester (0.147 g, 0.285 mmol) in CH$_2$Cl$_2$(1.0 mL)-anisole(0.5 mL) at room temperature under nitrogen was added trifluoroacetic acid (1.0 mL). The resulting clear solution was stirred at room temperature for 1 hr, evaporated to dryness and chased with toluene-CH$_2$Cl$_2$ (1:1). The residue was triturated with Et$_2$O-hexane to give the title compound (0.100 g, 76%) as a white solid. MS(ES) for C$_{23}$H$_{26}$FN$_3$O$_6$ (MW 459.47): positive 482(M+Na); negative 458(M–H).

EXAMPLE 3

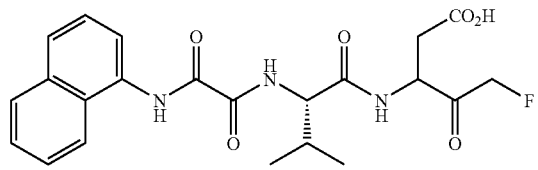

(3RS)-3-[N-(N'-(1-Naphthyl)Oxamyl)Valinyl] Amino-5-Fluoro-4-Oxopeintanoic Acid

Part A: (3RS,4RS)-3-[(N-Benzyloxycarbonyl)Valinyl]Amino-5-Fluoro-4-Hydroxypentanoic Acid, tert-Butyl Ester To a solution of (N-benzyloxycarbonyl)valine (0.332 g, 1.32 mmol) in CH$_2$Cl$_2$ (7.0 mL) at 0° C. (ice bath) under nitrogen was added hydroxybenzotriazole hydrate (0.219 g) followed by 1-ethyl-3-(3',3'-dimethyl-1'-aminopropyl)carbodiimide hydrochloride (0.317 g, 1.65 mmol). After stirring at 0° C. for 10 min, the mixture was treated with (3RS,4RS)-3-amino-5-fluoro-4-hydroxypentanoic acid, tert-butyl ester (0.228 g, 1.1 mmol) and the reaction allowed to warm to room temperature. After stirring at room temperature for 24 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography eluting with EtOAc-hexane (1:1) to give the title compound (0.423 g, 87%) as colorless glass. TLC(MeOH—$CH_2Cl_2$; 5:95) Rf=0.17.

Part B: (3RS)-3-[N-(N'-(1-Naphthyl)Oxamyl)Valinyl]Amino-5-Fluoro-4-Oxopentanoic Acid Starting with (3RS,4RS)-3-[(N-benzyloxycarbonyl)valinyl]amino-5-fluoro-4-hydroxypentanoic acid, tert-butyl ester and following the methods described in Example 2, Parts B through E gave the title compound as a white solid. MS(ES) for $C_{22}H_{24}FN_3O_6$ (MW 445.45): positive 468(M+Na), 484(M+K); negative 444(M−H).

EXAMPLE 4

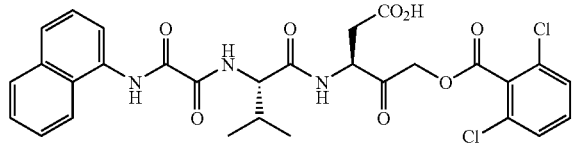

(3S)-3-[N-('-(1-Naphthyl)Oxamyl)Valinyl]Amino-5-(2',6'-Dichlorobenzyloxy)-4-Oxopentanoic Acid Part A: [(N-Benzyloxycarbonyl)Valinyl]Aspartic Acid, β-tert-Butyl, α-Methyl Ester To a solution of (N-benzyloxycarbonyl)valine (2.10 g, 8.36 mmol) in $CH_2Cl_2$(20 mL) at 0° C. (ice bath) under nitrogen was added hydroxybenzotriazole hydrate (1.74 g) followed by 1-ethyl-3-(3',3'-dimethyl-1'-aminopropyl)carbodiimide hydrochloride (2.40 g, 12.5 mmol). After stirring at 0° C. for 10 min. the mixture was treated with aspartic acid, β-tert-butyl, α-methyl ester hydrochloride (2.00 g, 8.34 mmol) and N-methylmorpholine (1.1 mL, 10 mmol), and the reaction allowed to warm to room temperature. After stirring at room temperature for 2.5 hrs, the mixture was concentrated and the residue partitioned between EtOAc-water. The organic phase was washed with water, 5% $KHSO_4$, saturated $NaHCO_3$ and saturated NaCl solutions, dried over anhydrous $Na_2SO_4$ and evaporated to give the title compound (3.55 g, 97%) as a white solid after tituration with $Et_2O$-hexane. TLC(EtOAc-hexane; 1:1) Rf=0.48.

Part B: (Valinyl)Aspartic Acid, βtert-Butyl, α-Methyl Ester p-Toluenesulfonate Salt To a solution of [(N-benzyloxycarbonyl)valinyl]aspartic acid, β-tert-butyl, α-methyl ester (3.55 g, 8.12 mmol) in MeOH (300 mL) was added p-toluenesulfonic acid hydrate (1.55 g, 8.12 mmol) and 10% Pd—C (0.30 g) and resulting mixture stirred under a hydrogen atmosphere (balloon) for 2 hrs. The mixture was filtered through Celite washing the filter cake with $CH_2Cl_2$ and the combined filtrates evaporated to dryness. The residue was chased with $CH_2Cl_2$ to give the title product (3.85 g, quantitative) as a colorless foam.

Part C: [N-(N'-(1-Naphthyl)Oxamyl)Valinyl]Aspartic Acid, β-tert-Butyl, α-Methyl Ester To a solution of N-(1-naphthyl)oxamic acid (0.683 g, 3.18 mmol, see Example 1, Part A) in N-methylpyrrolidone(7.0 mL)-$CH_2Cl_2$(7.0 mL) at room temperature under nitrogen was added O-(7-azabenzotriazol-1-yl)-N,N,N',N'-tetramethyluronium hexafluorophate (1.329 g, 3.49 mmol). After stirring for 15 min, the mixture was treated with N-(valinyl)aspartic acid, β-tert-butyl, α-methyl ester p-toluenesulfonate salt (1.506 g, 3.18 mmol) and diisopropylethylamine (1.66 mL, 9.53 mmol). After stirring at room temperature for 2 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with EtOAc-hexane (1:1) to give the title compound (1.153 g, 73%) as a white solid. TLC(EtOAc-hexane; 2:1) Rf=0.48.

Part D: [N-(N'-(1-Naphthyl)Oxamyl)Valinyl]Aspartic Acid, β-tert-Butyl Ester

To a solution of [N-(N'-(1-naphthyl)oxamyl)valinyl]aspartic acid, β-tert-butyl, α-methyl ester (0.490 g, 0.98 mmol) in dioxane (2.4 mL) was added 1.0 N LiOH solution (1.0 mL, 1.0 mmol). After stirring at room temperature for 1 hr, the mixture was acidified with 1.0 N HCl and extracted with EtOAc. The extract was washed with saturated NaCl solution, dried over anhydrous $Na_2SO_4$ and evaporated to give the title compound (0.481 g, quantitative) as a white solid. TLC(MeOH—$CH_2Cl_2$; 1:9) Rf=0.15.

Part E: (3S)-3-[N-(N'-(1-Naphthyl)Oxamyl)Valinyl]Amino-5-Diazo-4-Oxopentanoic Acid tert-Butyl Ester To a solution of [N-(N'-(1-naphthyl)oxamyl)valinyl]aspartic acid, O-tert-butyl ester (0.095 g, 0.20 mmol) and N-methylmorpholine (22 μL, 0.20 mmol) in tetrahydrofuran (2.0 mL) at −10° C. (NaCl/ice bath) under nitrogen was added isobutyl chloroformate (28 μL, 0.22 mmol). After stirring at −10° C. for 0.5 hrs, the resulting mixed anhydride was treated with excess diazomethane/$Et_2O$ solution (prepared from 0.072 g, 0.49 mmol of 1-methyl-3-nitro-1-nitrosoguanidine, 1.0 mL 40% KOH/1.0 ml $Et_2O$). After stirring at −10° C. for an additional 1 hr, the mixture was concentrated and the residue purified by flash chromatography on silica gel eluting with $CH_2Cl_2$-$Et_2O$-hexane (1:2:2) to give the title compound (0.062 g, 62%) as a white solid. TLC(EtOAc-hexane; 2:1) Rf=0.63.

Part F: (3S)-3-[N-(N'-(1-Naphthyl)Oxamyl)Valinyl] Amino-5-Bromo-4-Oxopentanoic Acid tert-Butyl Ester To a solution of (3S)-3-[N-(N'-(1-naphthyl)oxamyl)valinyl]amino-5-diazo-4-oxopentanoic acid tert-butyl ester (0.135 g, 0.265 mmol) in tetrahydrofuran (3.0 mL) at 0° C. was added 48% aqueous HBr (30 μL, 0.27 mmol). Gas evolution was observed. After 15 min, the mixture was partitioned between EtOAc-saturated NaHCO$_3$, the organic phase washed with saturated NaCl solution, dried over anhydrous Na$_2$SO$_4$ and evaporated to give the title compound (0.147 g, quantitative) as a white solid. TLC(EtOAc-hexane; 2:1) Rf=0.72.

Part G: (3S)-3-[N-(N'-(1-Naphthyl)Oxamyl)Valinyl] Amino-5-(2'?6'-Dichlorobenzoyloxy)-4-Oxopentanoic Acid, tert-Butyl Ester To a solution of (3S)-3-[N-(N'-(1-naphthyl)oxamyl) valinyl]amino-5-bromo-4-oxopentanoic acid tert-butyl ester (0.100 g, 0.18 mmol) and 2,6-dichlorobenzoic acid (0.037 g, 0.20 mmol) in dimethylformamide (1.0 mL) at room temperature under nitrogen was added potassium fluoride (0.031 g, 0.53 mmol). After stirring at room temperature for 16 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. The residue was purified by flash chromatography on silica gel eluting with EtOAc-hexane (1:1) to give the title compound (0.084 g, 70%) as viscous oil. TLC(EtOAc-hexane; 2:1) Rf=0.71.

Part H: (3S)-3-[N-(N'-(1-Naphthyl)Oxamyl)Valinyl] Amino-5-(2',6'-Dichlorobenzoyloxy)-4-Oxopentanoic Acid To a solution of (3S)-3-[N-(N'-(1-naphthyl)oxamyl) valinyl]amino-5-(2',6'-dichlorobenzoyloxy)-4-oxopentanoic acid, tert-butyl ester (0.084 g, 0.125 mmol) in CH$_2$Cl$_2$(1.0 mL)-anisole(0.5 mL) at room temperature under nitrogen was added trifluoroacetic acid (1.0 mL). The resulting clear solution was stirred at room temperature for 1 hr, evaporated to dryness and chased with toluene-CH$_2$Cl$_2$ (1:1). The residue was triturated with Et$_2$O to give the title compound (0.060 g, 78%) as an off-white solid. MS(ES) for C$_{29}$H$_{27}$Cl$_2$N$_3$O$_8$ (MW 616.45): positive 638/640(M+Na); negative 614/616(M−H).

EXAMPLES 5–21

Starting with (3S)-3-[N-(N'-(1-naphthyl)oxamyl)valinyl] amino-5-bromo-4-oxopentanoic acid tert-butyl ester (see Example 4, Part F) and following the methods described in Example 4, Parts G through H, the compounds shown below in Table 3 were also prepared:

TABLE 3

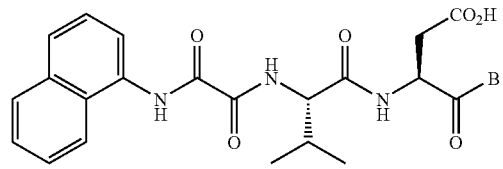

| Ex. | B | Formula | MW | MS(ES) pos. | MS(ES) neg. |
|---|---|---|---|---|---|
| 5 | CH$_2$O(2,6-diF-Ph) | C$_{28}$H$_{27}$F$_2$N$_3$O$_7$ | 555.53 | 578(M+Na) | 554(M−H) |
| 6 | CH$_2$O(2,4,6-triF-Ph) | C$_{28}$H$_{26}$F$_3$N$_3$O$_7$ | 573.52 | 596(M+Na) | 572(M−H) |
| 7 | CH$_2$O(2,3,5,6-tetraF-Ph) | C$_{28}$H$_{25}$F$_4$N$_3$O$_7$ | 591.51 | 614(M+Na) | 590(M−H) |
| 8 | CH$_2$O(6-Me-2-pyron-4-yl) | C$_{28}$H$_{29}$N$_3$O$_9$ | 551.55 | 574(M+Na) | 550(M−H) |
| 9 | CH$_2$O(2-Ph-5,6-benzopyran-4-on-3-yl) | C$_{37}$H$_{33}$N$_3$O$_9$ | 663.68 | 686(M+Na) | 662(M−H) |
| 10 | CH$_2$OPO(Me)Ph | C$_{29}$H$_{32}$N$_3$O$_8$P | 581.56 | 582(M+H) 604(M+Na) | 580(M−H) 694(M+TFA) |
| 11 | CH$_2$OPOPh$_2$ | C$_{34}$H$_{34}$N$_3$O$_8$P | 643.63 | 666(M+Na) | 642(M−H) |
| 12 | CH$_2$O(2-CF$_3$-pyrimidin-4-yl) | C$_{27}$H$_{26}$F$_3$N$_5$O$_7$ | 589.53 | 612(M+Na) | 588(M−H) |
| 13 | CH$_2$O(5-CO$_2$Me-isoxazol-3-yl) | C$_{27}$H$_{28}$N$_4$O$_{10}$ | 568.54 | 591(M+Na) | 567(M−H) |
| 14 | CH$_2$OPO(Me)(1-naphthyl) | C$_{33}$H$_{34}$N$_3$O$_8$P | 631.62 | 654(M+Na) | 630(M−H) 744(M+TFA) |
| 15 | CH$_2$O(4-hydroxy-Ph) | C$_{28}$H$_{29}$N$_3$O$_8$ | 535.55 | 537/538(M+Na) | 535/536/537 (M−H) |
| 16 | CH$_2$O(4-OCOOCHCHCH$_3$-Ph) | C$_{32}$H$_{33}$N$_3$O$_{10}$ | 619.63 | 637(M+NH$_4$) | 618(M−H) |
| 17 | CH$_2$O(4-OCHCHCH$_3$-Ph) | C$_{31}$H$_{33}$N$_3$O$_8$ | 575.62 | 576(M+H) | 574(M−H) |
| 18 | CH$_2$O(1-Naphthyl) | C$_{32}$H$_{31}$N$_3$O$_7$ | 569.6128 | | |
| 19 | CH$_2$O(4-propyloxyphenyl) | C$_{30}$H$_{35}$N$_3$O$_6$ | 533.25 | 534(M+H) 551(M+NH$_4$) | |
| 20 | CF$_3$ | C$_{22}$H$_{22}$F$_3$N$_3$O$_6$ | 481.15 | 482(M+H) | |
| 21 | NH(CH$_2$)$_2$Ph | C$_{29}$H$_{32}$N$_4$O$_6$ | 532.23 | 533(M+H) | 531(M−H) |

EXAMPLE 22

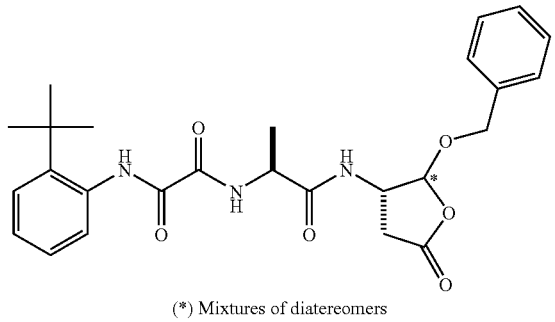

(*) Mixtures of diatereomers

N-[1-(2-Benzyloxy-5oxo-tetrahydro-furan-3-ylcarbamoyl)-ethyl]-N'-(2-tert-butyl-phenyl)-oxalamide Part A: 3-(9H-Fluoren-9-ylmethoxycarbonylamino)-N-methoxy-N-methyl-suecinamic acid tert-butyl ester

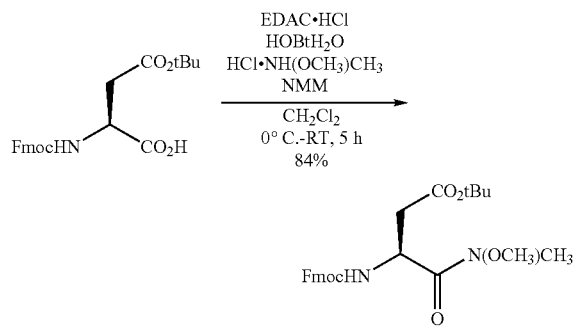

To a solution of 2-(9H-Fluoren—9-ylmethoxycarbonylamino)-succinic acid 4-tert-butyl ester (5.00 g, 12.15 mmol) in $CH_2Cl_2$ (50 mL) at 0° C. under $N_2$ was added 1.2 equiv of 1-(3-Dimethylaminopropyl)-3-ethylcarbodiimide HCl (EDAC) (2.79 g, 14.58 mmol) and 1.1 equiv of HOBt.$H_2O$ (2.05 g, 13.37 mmol). The mixture was stirred at 0° C. under $N_2$ for 15 min before addition of HCl HN(OMe)Me (1.42 g, 14.58 mmol), followed by 4-Methylmorpholine (NMM) (2.00 mL, 18.23 mmol). After stirring at 0° C. to room temperature for 5 hrs, the mixture was partitioned between EtOAc/water. The organic phase was washed with water, 5% $KHSO_4$, saturated $NaHCO_3$, and saturated NaCl solutions, dried over anhydrous $Na_2SO_4$ and evaporated to give crude title compound. The residue was purified by flask column chromatography on silica gel eluting with EtOAc/Hexane (20%) to give the title compound (4.62 g, 85%) as a white foam. TLC (40%) Et(Ac/Hexane) $R_f$=0.44; $^1$HNMR ($CDCl_3$) δ 7.75 (d, J=7.5 Hz, 2H), 7.50 (t, J=6.9 Hz, 2H), 7.40 (t, J=7.5 Hz, 2H), 7.33–7.28 (dt, J=7.5, 1.2 Hz, 2H), 5.71 (d, J=9.0 Hz, 1H), 5.04 (bq, J=7.8 Hz, 1H), 4.36 (d, J=7.2 Hz, 2H), 4.23 (t J=7.2 Hz, 1H), 3.79 (s, 3H), 3.24 (s, 3H), 2.78–2.71 (dd, J=15.0, 5.4 Hz, 1H), 2.62–254 (15.0, 6.9 Hz, 1H), 1.45 (s, 9H). MS(ES) for $C_{23}H_{25}NO_6$ (MW=454.52): positive 455 (MH+).

Part B: 3-(9H-Fluoren-9-ylmethoxycarbonylamino)-4-oxo-butyric acid tert-butyl ester

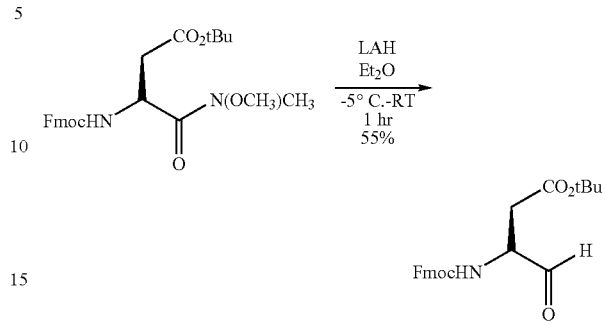

To a suspension of 3-(9H-Fluoren-9-ylmethoxycarbonylamino)-N-methoxy-N-methyl-succinamic acid tert-butyl ester (4.57 g, 10.04 mmol) in Ethyl ether (30 mL) at −5° C. was added dropwise 0.5 equiv of 1.0M Lithium aluminum hydride (LAH) in ethyl ether (5.02 mL, 5.02 mmol). After stirring at −5° C. to room temperature for 1 hr, the reaction mixture was treated with 5% $KHSO_4$ (200 mL), stirred for 5 min and then partitioned between EtOAc/water. The organic phase was washed with saturated NaCl solution (200 mL), dried over $Na_2SO_4$ and evaporated to dryness. The residue was purified by flask column chromatography on silica gel eluting with EtOAc/Hexane (20%) to give the title compound (2.18 g, 55%) as a clear oil. TLC (30% EtOAc/Hexane) $R_f$=0.35; $^1$HNMR ($CDCl_3$) δ 9.65 (s, 1H), 7.77 (d, J=7.2 Hz, 2H), 7.50 (d, J=7.5 Hz, 2H), 7.41 (t, J=7.5 Hz, 2H), 7.33 (dt, J=7.5, 1.2 Hz, 2H), 5.88 (d, J=7.2 Hz, 1H), 4.50–4.36 (m, 2H), 4.24 (t, J=6.6 Hz, 1H), 3.54–3.45 (m, 1H), 3.00–2.93 (dd, J=17.4, 4.8 Hz, 1H), 2.82–274 (dd, J=17.7, 5.1s Hz, 1H), 1.45 (s, 9H). MS(ES) for $C_{23}H_{25}NO_5$ (MW=395.45): positive 396 (MH+).

Part C: 4,4-Bis-benzyloxy-3-(9H-fluoren-9-yl-methoxycarbonylamino)-butyric acid tert-butyl ester

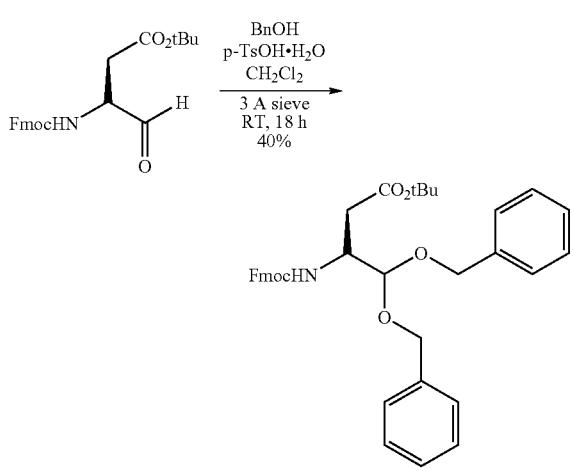

To a suspension of 3-(9H-Fluoren-9-ylmethoxycarbonylamino)-4-oxo-butyric acid tert-butyl ester (1.24 g, 3.14 mmol) in Dichloromethane (10 mL) at room temperature was added 0.20 equiv TsOH.$H_2O$ (0.12 g, 0.63 mmol) and followed by dropwise 5.0 equiv of Benzyl alcohol (1.62 mL, 15.68 mmol). After stirring room temperature for 18 hrs, the reaction mixture was filtered through celite and the filtrate was concentrated in vacuo to obtain a crude title compound. The residue was purified by flask column chromatography on silica gel eluting with EtOAc/Hexane (10–40%) to give the title compound (0.75 g, 40%) as clear oil. TLC (40% EtOAc/Hexane) $R_f$=0.68; $^1$HNMR (CDCl$_3$) δ 7.76 (d, J=7.2 Hz, 2H), 7.59 (d, J=7.5 Hz, 2H), 7.39 (t, J=7.5 Hz, 21H), 7.35–7.27 (m, 12H), 5.37 (d, J=9.6 Hz, 1H), 4.73–4.52 (m, 5H), 4.35 (d, J=6.6 Hz, 2H), 4.24–4.16 (q, J=6.6 Hz, 2H), 2.55–2.50 (m, 2H), 1.39 (s, 9H). MS(ES) for $C_{37}H_{39}NO_9$ (MW=593.71): positive 611 (M+NH$_4$+).

Part D: 4,4-Bis-benzyloxy-3-{2-[(2-tert-butyl-phenylaminooxalyl)-amino]-propionylamino}-butyric acid tert-butyl ester

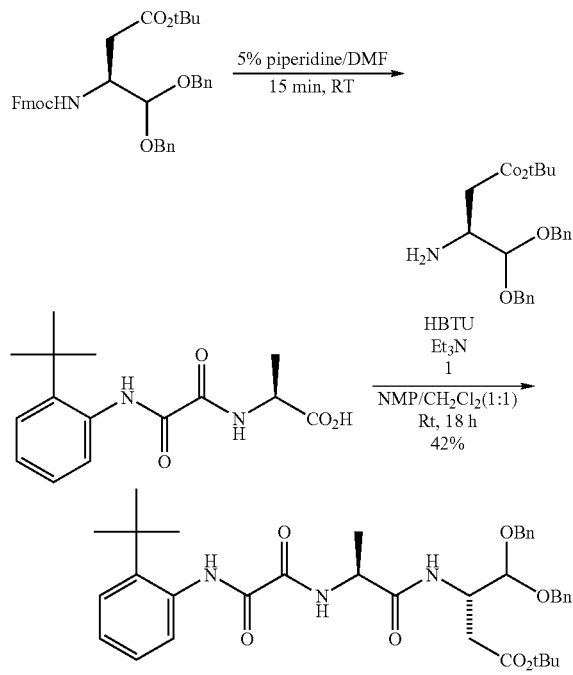

4,4-Bix-benzyloxy-3-(9H-fluoren-9-ylmethoxycarbonylamino)-butyric acid tert-butyl ester (0.63 g, 1.06 mmol) was stirred in 5% Piperidine/DMF (3 mL) at room temperature. After stirring at room temperature for 15 min, the reaction mixture was treated with Water (20 mL), stirred for 5 min and then partitioned between EtOAc/water. The organic phase was washed with Water (3×20 mL), saturated NaCl solution (3×20 mL), dried over Na$_2$SO$_4$ and evaporated to dryness to afford crude 3-Amino-4,4-bis-benzyloxy-butyric acid tertbutyl ester (1). The crude residue 1 was ready to be used for coupling reaction as a crude product.

To a solution of (2S)-2-[(2-tert-butyl-phenylaminooxalyl)-amino]-propanoic acid (0.37 g, 1.27 mmol) in CH$_2$Cl$_2$/NMP (1:1, 3 mL) at room temperature under N$_2$ was added 1.5 equiv HBTU (0.61 g, 1.59 mmol). The mixture solution was stirred at room temperature under N$_2$ for 45 min before addition of 1, followed by Et$_3$N (0.44 mL, 3.18 mmol). After stirring at room temperature for 18 hrs, the mixture was partitioned between EtOAc-water. The organic phase was washed with water, 5% KHSO$_4$, saturated NaHCO$_3$, and saturated NaCl solutions, dried over anhydrous Na$_2$SO$_4$ and evaporated to give crude title compound. The residue was purified by flask column chromatography on silica gel eluding with EtOAc/Hexane (20%) to give the title compound (0.29 g, 42%) as a yellow foam. TLC (30% EtOAc/Hexane) $R_f$=0.59; $^1$HNMR (CDCl$_3$) δ 9.53 (s, 1H), 8.06 (dd, J=8.1, 3.6 Hz, 1H), 8.01 (dt, J=8.1, 1.2 Hz, 1H), 7.42 (d, J=7.5 Hz, 1H), 7.37–7.25 (m, 11H), 7.17 (tt, J=7.5, 1.2 Hz, 1H), 6.62–6.53 (dd, J=16.2, 9.0 Hz, 1H), 4.72–4.35 (m, 7H), 2.66 (d, J=6.0 Hz, 2H), 1.45 (s, 9H), 1.38 (d, J=4.2 Hz, 3H); MS(ES) for $C_{37}H_{47}N_3O_7$ (MW −645.79): negative 654 ([M−H]$^−$).

Part E: N-[1-(2-Benzyloxy-5-oxo-tetrahydro-furan-3-ylcarbamoyl)-ethyl]-N'-(2-tert-butyl-phenyl)-oxalamide

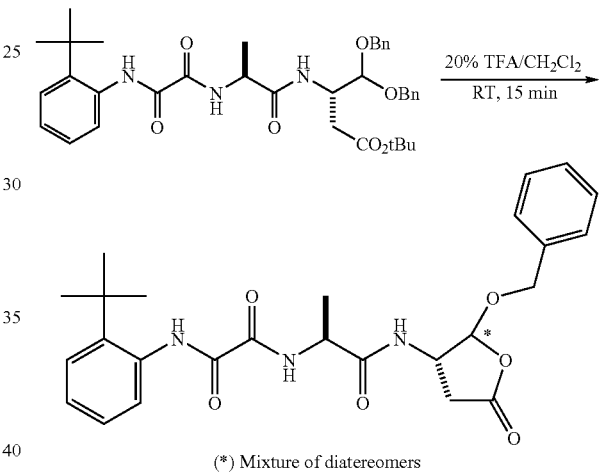

(*) Mixture of diatereomers 4,4-Bis-benzyloxy-3-{2-[(2-tert-butyl-phenylaminooxalyl)-amino]-propionylamino}-butyric acid tert-butyl ester (0.16 g, 0.25 mmol) was stirred in 205% TFA/CH$_2$Cl$_2$ (2 mL) at room temperature. After stirring at room temperature for 15 min., the reaction mixture was concentrated to dryness to afford crude tittle compounds. The residue was purified by flask column chromatography on silica gel eluding with EtOAc/Hexane (20–40%) to give the title compounds (0.09 g, 74%) as white foam.

Major diastereomer: TLC (40% EtOAc/Hexane) $R_f$=0.29; $^1$HNMR (CDCl$_3$) δ 9.53 (d, J=7.2 Hz, 1H), 8.09 (t, J=7.8 Hz, 1H), 7.93 (m) 1H), 7.42 (d, J=9.0 Hz, 1H), 7.35–7.15 (m, 7H), 6.70 (d, J=8.1 Hz, 1H), 5.45 (d, J=5.1 Hz, 1H), 4.90–4.41 (m, 4H), 3.06–2.83 (m, 1H), 2.53–2.35 (m, 1H), 1.47 (d, J=7.2 Hz, 3H), 1.44 (s, 9H); MS(ES) for $C_{26}H_{31}N_3O_6$ (MW=481.54): positive 482 (MH+).

Minor diastereomer: TLC (40% EtOAc/Hexane) $R_f$=0.22; $^1$HNMR (CDCl$_3$) δ 9.52 (s, 1H), 8.02–7.93 (m, 2H), 7.44 (dd, J=8.1, 1.5 Hz, 1H), 7.36–8.28 (m, 6H), 7.19 (dt, J=9.30, 1.5 Hz, 1H) 6.67 (d, J=7.8 Hz, 1H), 5.54 (d, J=5.4 Hz, 1H), 4.92–4.44 (m, 4H), 2.95–2.85 (m, 1H), 2.55–2.44 (m, 1H), 1.49 (d, J=7.2 Hz, 3H), 1.44 (s, 9H); MS(ES) for $C_{26}H_{31}N_3O_6$ (MW=481.54): positive 482 (MH+).

EXAMPLE 23

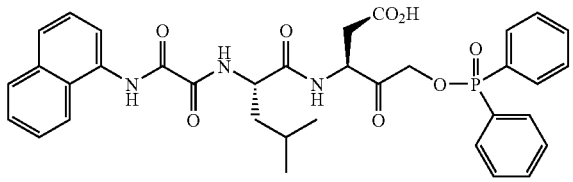

(3S)-3-[N-(N'-(1-Naphthyl)Oxamyl)Leucinyl]
Amino-5-(Diphenylphosphinyloxy)-4-Oxopentanoic
Acid Part A: [(N-Benzyloxycarbonyl)Leucinyl]Aspartic Acid, β-tert-Butyl, α-Methyl Ester To a solution of (N-benzyloxycarbonyl)leucine, N-hydroxysuccinimide ester (4.54 g, 12.5 mmol) and aspartic acid, β-tert-butyl, α-methyl ester hydrochloride (3.00 g, 12.5 mmol) in $CH_2Cl_2$ (20 mL) at room temperature under nitrogen was added N-methylmorpholine (1.65 mL, 15 mmol). After stirring at room temperature for 18 hrs, the mixture was partitioned between EtOAc-water. The organic phase was washed with 5% $KHSO_4$, saturated $NaHCO_3$ and saturated NaCl solutions, dried over anhydrous $Na_2SO_4$ and evaporated to give the title compound (5.56 g, 99%) as viscous oil. TLC(EtOAc-hexane; 1:1) Rf=0.48.

Part B: (3S)-3-[N-(N'-(1-Naphthyl)Oxamyl)Leucinyl]Amino-5-Bromo-4-Oxopentanoic Acid tert-Butyl Ester Starting with [(N-benzyloxycarbonyl)leucinyl]aspartic acid, β-tert-butyl, α-methyl ester and following the methods described in Example 4, Parts B through F; gave the title compound as a white solid. TLC($CH_2Cl_2$-$Et_2O$-hexane; 1:2:2) Rf=0.32.

Part C: (3S)-3-[N-(N'-(1-Naphthyl)Oxamyl)Leucinyl]Amino-5-(Diphenylphopshinyloxy)-4-Oxopentanoic Acid, tert-Butyl Ester To a solution of (3S)-3-[N-(N'-(1-naphthyl)oxamyl)leucinyl]amino-5-bromo-4-oxopentanoic acid tert-butyl ester (0.108 g, 0.187 mmol) and diphenylphosphinic acid (0.046 g, 0.21 mmol) in dimethylformamide (1.0 mL) at room temperature under nitrogen was added potassium fluoride (0.033 g, 0.58 mmol). After stirring at room temperature for 48 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with $CH_2Cl_2$-$Et_2O$-hexane (1:2:2) to give the title compound (0.114 g, 85%) as a white solid. TLC(EtOAc-hexane; 2:1) Rf=0.26.

Part D: (3S)-3-[N-(N'-(1-Naphthyl)Oxamyl)Leucinyl]Amino-5-(Diphenylphosphinyloxy)-4-Oxopentanoic Acid To a solution of (3S)-3-[N-(N'-(1-naphthyl)oxamyl)leucinyl]amino-5-(diphenylphosphinyloxy)-4-oxopentanoic acid, tert-butyl ester (0.114 g, 0.16 mmol) in $CH_2Cl_2$(1.0 mL)-anisole(0.5 mL) at room temperature under nitrogen was added trifluoroacetic acid (1.0 mL). The resulting clear solution was stirred at room temperature for 1 hr, evaporated to dryness and chased with toluene-$CH_2Cl_2$ (1:1). The residue was triturated with $Et_2O$-hexane to give the title compound (0.062 g, 59%) as an off-white solid. MS(ES) for $C_{34}H_{34}N_3O_8P$ (MW 657.66): positive 680(M+Na); negative 656(M–H).

EXAMPLES 24–27

Starting with (3S)-3-[N-(N'-(1-naphthyl)oxamyl)leucinyl]amino-5-bromo-4-oxopentanoic acid tert-butyl ester (see Example 23, Part B) and following the methods described in Example 23, Parts C through D, the compounds shown below in Table 4 were also prepared:

TABLE 4

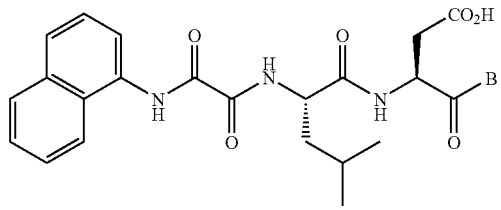

| Ex. | B | Formula | MW | MS(ES) pos. | MS(ES) neg. |
|---|---|---|---|---|---|
| 24 | $CH_2OCO(2,6\text{-}diCl\text{-}Ph)$ | $C_{30}H_{29}Cl_2N_3O_8$ | 630.48 | 652/654 (M+Na) | 628/630 (M–H) |
| 25 | $CH_2O(2,4,6\text{-}triF\text{-}Ph)$ | $C_{29}H_{28}F_3N_3O_7$ | 587.55 | 610(M+Na) | 586(M–H) |
| 26 | $CH_2O(2,3,5,6\text{-}tetraF\text{-}Ph)$ | $C_{29}H_{27}F_4N_3O_7$ | 605.54 | 628(M+Na) | 604(M–H) |
| 27 | $CH_2OPO(Me)Ph$ | $C_{30}H_{34}N_3O_8P$ | 595.59 | 596(M+H) 618(M+Na) | 594(M–H) 708(M+TFA) |

EXAMPLES 28–77

Following the general methods described in Example 4, Parts A through H substituting (N-benzyloxycarbonyl)alanine for (N-benzyloxycarbonyl)valine in Part A, the appropriate oxamic acid for N-(1-naphthyl)oxamic acid in Part C, and the appropriate acid or phenol for 2,6-dichlorobenzoic acid in Part G, the compounds shown below in Table 5 were also prepared:

TABLE 5

| Ex. | R¹ | B | Formula | MW | MS(ES) Pos. | MS(ES) neg. |
|---|---|---|---|---|---|---|
| 28 | (2-Ph)Ph | CH$_2$O(2-F-Ph) | C$_{28}$H$_{26}$FN$_3$O$_7$ | 535.53 | 558(M+Na) | 534(M−H) |
| 29 | (2-Ph)Ph | CH$_2$OCO(2,6-di-Cl-Ph) | C$_{29}$H$_{25}$Cl$_2$N$_3$O$_8$ | 614.44 | 652/654 (M+K) | 612/614(M−H) |
| 30 | (2-Ph)Ph | CH$_2$OPOPh$_2$ | C$_{34}$H$_{32}$N$_3$O$_8$P | 641.61 | 664(M+Na) 680(M+K) | 640(M−H) |
| 31 | (2-t-Bu)Ph | CH$_2$O(2-F-Ph) | C$_{26}$H$_{30}$FN$_3$O$_7$ | 515.54 | 516(M+H) 538(M+Na) 554(M+K) | 514(M−H) |
| 32 | (2-t-Bu)Ph | CH$_2$OPOPh$_2$ | C$_{32}$H$_{36}$N$_3$O$_8$P | 621.63 | 644(M+Na) 666(M+K) | 620(M−H) |
| 33 | 1-naphthyl-CH$_2$ | CH$_2$O(2,3,5,6-tetra-F-Ph) | C$_{27}$H$_{23}$F$_4$N$_3$O$_7$ | 577.48 | 600(M+Na) 616(M+K) | 576(M−H) |
| 34 | 1-naphthyl-CH$_2$ | CH$_2$OCO(2,6-di-Cl-Ph) | C$_{28}$H$_{25}$Cl$_2$N$_3$O$_8$ | 602.42 | 624/626(M+Na) 640/642(M+K) | 600/602(M−H) 714/716 (M+TFA) |
| 35 | 1-naphthyl-CH$_2$ | CH$_2$OPOPh$_2$ | C$_{33}$H$_{32}$N$_3$O$_8$P | 629.60 | 652(M+Na) 668(M+K) | 628(M−H) |
| 36 | (2-tBu)Ph | CH$_2$O(2,3,5,6-tetra-F-4-Br)Ph) | C$_{26}$H$_{26}$BrF$_4$N$_3$O$_7$ | 648.40 | | 646(M−H) |
| 37 | (2-tBu)Ph | CH$_2$OCO(2,6-di-Cl-Ph) | C$_{27}$H$_{29}$Cl$_2$N$_3$O$_8$ | 594.45 | 616/618(M+Na) | 492/594(M−H) |
| 38 | (2-1)Ph | CH$_2$OCO(2,6-di-Cl-Ph) | C$_{23}$H$_{20}$Cl$_2$IN$_3$O$_8$ | 664.24 | | |
| 39 | (2-1)Ph | CH$_2$OCO(2,6-di-Cl-Ph) | C$_{23}$H$_{20}$Cl$_2$FN$_3$O$_8$ | 556.33 | | |
| 40 | (2,5-di-tBu)Ph | CH$_2$O(2,3,5,6-tetra-F-Ph) | C$_{30}$H$_{35}$F$_4$N$_3$O$_7$ | 625.62 | 626(M+H) 648(M+Na) | 624(M−H) |
| 41 | (2-Cl)Ph | CH$_2$OPOPh$_2$ | C$_{28}$H$_{27}$ClN$_3$O$_8$P | 599.96 | | 598(M−H) |
| 42 | (2-Cl)Ph | CH$_2$OCO(2,6-di-Cl-Ph) | C$_{23}$H$_{20}$Cl$_3$N$_3$O$_8$ | 572.79 | 572/574/576 (M+H) | 570/572/574 (M−H) |
| 43 | (4-F)Ph | CH$_3$OPOPh$_2$ | C$_{28}$H$_{27}$FN$_3$O$_8$P | 583.51 | 606(M+H) | 582(M−H) |
| 44 | (4-F)Ph | CH$_2$OCO(2,6-di-Cl-Ph) | C$_{23}$H$_{20}$Cl$_2$FN$_3$O$_8$ | 556.33 | 578/480(M+Na) | 554/556(M−H) |
| 45 | (2-morpholin-4-yl-5-trifluoromethyl)Ph | CH$_2$OPOPh$_2$ | C$_{35}$H$_{35}$F$_6$N$_4$O$_{11}$P | 832.65 | 741(M+Na) | 717(M−H) |
| 46 | (2-pyrrolidin-1-yl-5-trifluoromethyl)Ph | CH$_2$OPOPh$_2$ | C$_{35}$H$_{35}$F$_6$N$_4$O$_{10}$P | 816.65 | 725(M+Na) | 701(M−H) |
| 47 | (2-tBu)Ph | CH$_2$OPOPh$_2$ | C$_{32}$H$_{36}$N$_3$O$_8$P | 621.63 | 644(M+Na) | 620(M−H) |
| 48 | 5,6,7,8-tetrahydro-1-naphthyl | CH$_2$OPOPh$_2$ | C$_{32}$H$_{34}$N$_3$O$_8$P | 619.61 | 620(M+H) 642(M+Na) | 618(M−H) |
| 49 | 5,6,7,8-tetrahydro-1-naphthyl | CH$_2$OCO(2,6-di-Cl-Ph) | C$_{27}$H$_{27}$Cl$_2$N$_3$O$_8$ | 592.43 | 614/616(M+Na) | 590/592(M−H) |
| 50 | 5,6,7,8-tetrahydro-1-naphthyl | CH$_2$O(2,3,5,6-tetra-F-ph) | C$_{26}$H$_{25}$F$_4$N$_3$O$_7$ | 567.49 | 590(M+Na) | 566(M−H) |
| 51 | PhCH$_2$ | CH$_2$O(2,3,5,6-tetra-F-Ph) | C$_{23}$H$_{23}$Cl$_2$N$_3$O$_8$ | 552.37 | | 550/552(M−H) |
| 52 | PhCH$_2$ | CH$_2$OCO(2,6-di-Cl-Ph) | C$_{24}$H$_{23}$Cl$_2$N$_3$O$_8$ | 552.37 | | 550/552(M−H) |

TABLE 5-continued

Structure: R¹—NH—C(O)—C(O)—NH—CH(CH₃)—C(O)—NH—CH(CH₂-CO₂H)—C(O)—B

| Ex. | R¹ | B | Formula | MW | MS(ES) Pos. | MS(ES) neg. |
|---|---|---|---|---|---|---|
| 53 | 1-adamantanyl | CH₂OPOPh₂ | $C_{32}H_{38}N_3O_8P$ | 623.64 | 646(M+Na) | 622(M−H) |
| 54 | 1-adamantanyl | CH₂OCO(2,6-di-Cl-Ph) | $C_{27}H_{31}Cl_2N_3O_8$ | 596.46 | | 594/596(M−H) |
| 55 | cyclo-hexyl | CH₂OCO(2,6-di-Cl-Ph) | $C_{23}H_{27}Cl_2N_3O_8$ | 544.39 | 566(M+Na) | |
| 56 | cyclo-hexyl | CH₂OPOPh₂ | $C_{28}H_{34}N_3O_8P$ | 571.57 | 594(M+Na) 610(M+K) | 570(M−H) |
| 57 | (2-Cl)Ph | CH₂OPOPh₂ | $C_{28}H_{27}ClN_3O_8P$ | 5999.96 | 622/624(M+Na) | 598/600(M−H) |
| 58 | (2-Cl)Ph | CH₂OCO(2,6-di-Cl-Ph) | $C_{23}H_{20}Cl_3N_3O_8$ | 572.79 | 594(M+Na) | |
| 59 | (2,5-di-6Bu)Ph | CH₂OPOPh₂ | $C_{36}H_{44}N_3O_8P$ | 677.73 | 700(M+Na) | 676(M−H) |
| 60 | (2,5-di-6Bu)Ph | CH₂OCO(2,6-di-Cl-Ph) | $C_{31}H_{37}Cl_2N_3O_8$ | 650.55 | 650/652(M+H) 672/674(M+Na) | 648/650(M−H) |
| 61 | 1,2,3,4-tetrahydro-1-naphthyl | CH₂OPOPh₂ | $C_{32}H_{34}N_3O_8P$ | 619.61 | 620(M+H) 642(M+Na) | 618(M−H) |
| 62 | 1,2,3,4-tetrahydro-1-naphthyl | CH₂OCO(2,6-di-Cl-Ph) | $C_{27}H_{27}Cl_2N_3O_8$ | 592.43 | 614/616(M+Na) | 590/592(M−H) |
| 63 | 1-adamantanyl | CH₂O(2,3,5,6-tetra-F-Ph) | $C_{30}H_{23}F_4N_3O_7$ | 613.52 | 636(M+Na) | 612(M−H) |
| 64 | 1-adamantanyl | CH₂OPOPh₂ | $C_{36}H_{32}N_3O_8$ | 665.64 | 688(M+Na) | 664(M−H) |
| 65 | 1-adamantanyl | CH₂OCO(2,6-di-Cl-Ph) | $C_{31}H_{25}Cl_2N_3O_8$ | 638.46 | 660/662(M+Na) | 636/638(M−H) |
| 66 | (2-F)Ph | CH₂O(2,3,5,6-tetra-F-Ph) | $C_{22}H_{18}F_5N_3O_7$ | 531.39 | 554(M+Na) | 530(M−H) |
| 67 | (2-F)Ph | CH₂OPOPh₂ | $C_{28}H_{27}FN_3O_8P$ | 583.51 | 606(M+Na) | 582(M−H) |
| 68 | (2-F)Ph | CH₂OCO(2,6-di-Cl-Ph) | $C_{23}H_{20}Cl_2FN_3O_8$ | 556.33 | 578/580(M+Na) | 554/556(M−H) |
| 69 | (4-n-heptyl)Ph | CH₂OPOPh₂ | $C_{35}H_{42}N_3O_8P$ | 663.71 | 686(M+Na) | 662(M−H) |
| 70 | (4-n-heptyl)Ph | CH₂OCO(2,6-di-Cl-Ph) | $C_{30}H_{35}Cl_2N_3O_8$ | 636.53 | 658/660(M+Na) | 634/636(M−H) |
| 71 | Ph(CH₂)₂ | CH₂O(2,3,5,6-tetra-F-Ph) | $C_{24}H_{23}F_4N_3O_7$ | 541.46 | 542(M+H) 564(M+Na) | 540(M−H) |
| 72 | Ph(CH₂)₂ | CH₂OPOPh₂ | $C_{30}H_{32}N_3O_8P$ | 593.57 | 594(M+H) 616(M+Na) | 592(M−H) 566/568(M+H) |
| 73 | Ph(CH₂)₂ | CH₂OCO(2,6-di-Cl-Ph) | $C_{25}H_{25}Cl_2N_3O_8$ | 566.39 | 566/568(M+H) 588/590(M+Na) | 564/566(M−H) 714(M+Na) |
| 74 | (2-1)Ph | CH₂OPOPh₂ | $C_{28}H_{27}IN_3O_8P$ | 691.41 | 714(M+Na) | 690(M−H) |
| 75 | (2-1)Ph | CH₂OCO(2,6-di-Cl-Ph) | $C_{23}H_{20}Cl_2IN_3O_8$ | 664.24 | 686/688(M+Na) | 662/664(M−H) 776(M+TFA) |
| 76 | (2-tBu)Ph | CH₂OCO(2,6-di-Cl-Ph) | $C_{27}H_{29}Cl_2N_3O_8$ | 594.45 | 616/618(M+Na) | 592/594(M−H) |
| 77 | (2-PhCH₂)Ph | CH₂O(2,3,5,6-tetra-F-Ph) | $C_{29}H_{30}N_3O_8P$ | 579.57 | | 578(M−H) |

EXAMPLE 78

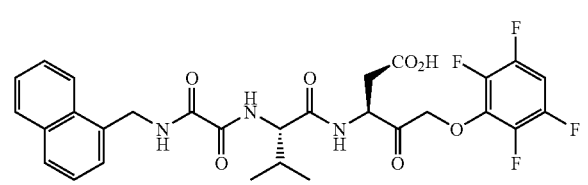

(3S)-3-[N-(N'-(1-Naphthylnethyl)Oxamyl)Valnyl]Amino-5-(2',3',5',6'-Tetrafluorophenoxy)-4-Oxopentanoic Acid Part A: [(N-Benzyloxycarbonyl)Valinyl]Aspartic Acid, β-tert-Butyl Ester To a suspension of aspartic acid β-tert-butyl ester (3.784 g, 20 mmol) in acetonitrile (200 mL) at room temperture under nitrogen was added bis(trimethylsilyl)acetamide (9.9 mL, 40 mmol). After stirring at room temperature for 30 min, the resulting clear solution was treated with (N-benzyloxycarbonyl)valine N-hydroxysuccinimide ester (6.97 g, 20 mmol). After stirring at room temperature for an additional 18 hrs, the mixture was treated with water (20 mL), concentrated on a rotovap and then partitioned between EtOAc/water. The organic phase was washed with water, 5% KHSO₄ and saturated NaCl solutions, dried over anhydrous Na₂SO₄ and evaporated to a dryness. Trituration with Et₂O-

Part B: (3S)-3-[(N-Benzyloxycarbonyl)Valinyl] Amino-5-Bromo-4-Oxopentanoic Acid tert-Butyl Ester A solution of [(N-benzyloxycarbonyl)valinyl]aspartic acid, β-tert-butyl ester (8.37 g, 19.9 mmol) and N-methylmorpholine (3.50 mL, 32 mmol) in tetrahydrofuran (100 mL) at −10° C. (NaCl/ice bath) under nitrogen was treated dropwise with isobutyl chloroformate (3.87 mL, 29.8 mmol). After stirring at −10° C. for 20 min, the mixture was filtered (sinctered glass) into a pre-cooled receiver (ice bath) washing the filter cake with additional tetrahydrofuran (approx. 30 mL). The combined filtrate was treated with excess diazomethane/$Et_2O$ solution (prepared from 7.32 g, 50 mmol of 1-methyl-3-nitro-1-nitrosoguanidine, 40 mL 40% KOH/65 ml $Et_2O$) at 0° C. (ice bath) under nitrogen. After stirring at 0° C. for 15 min and at room temperature for 30 min, the reaction mixture was again cooled to 0° C. and treated with 48% HBr(10 mL, 60 mmol)/acetic acid(10 mL). After stirring at 0° C. for 15 min and at room temperature for 30 min, the mixture was partitioned between EtOAc-water. The organic phase was washed with water, saturated $NaHCO_3$, and saturated NaCl solutions dried over anhydrous $Na_2SO_4$ and evaporated to a dryness. Trituration with hexane gave the crude title compound (9.71 g, 98%) as a white solid. TLC(EtOAc-hexane; 1:1) Rf=0.63.

Part C: (3S)-3-[N-Benzyloxycarbonyl)Valinyl] Amino-5-(2',3',5',6'-Tetrafluorophenoxy)-4-Oxopentanoic Acid tert-Butyl Ester To a solution of (3S)-3-[(N-benzyloxycarbonyl)valinyl] amino-5-bromo-4-oxopentanoic acid tert-butyl ester (9.71 g, 19.4 mmol) and 2,3,5,6-tetrafluorophenol (3.65 g, 22 mmol) in tetrahydrofuran (20 mL) at room temperature under nitrogen was added potassium fluoride (2.91 g, 50 mmol). After stirring at room temperature for 4 hrs, the mixture was diluted with EtOAc (approx. 100 mL), washed with saturated $NaHCO_3$ and saturated NaCl solutions, dried over anhydrous $Na_2SO_4$ and evaporated to a dryness. The residue was purified by flash chromatography on silica gel eluting with EtOAc-hexane (1:3) to give the title compound (9.19 g, 79%) as a white solid after trituration with $Et_2O$-hexane. TLC(EtOAc-hexane; 1:1) Rf=0.70.

Part D: (3S,4RS)-3-[(N-Benzyloxycarbonyl)Valinyl] Amino-5-(2',3',5',6'-Tetrafluorophenoxy)-4-Hydroxypentanoic Acid tert-Butyl Ester To a solution of (3S)-3-[(N-benzyloxycarbonyl)valinyl] amino-5-(2',3',5',6'-tetrafluorophenoxy)-4-oxopentanoic acid tert-butyl ester (9.19 g, 15.7 mmol) in MeOH(200 mL)/tetrahydrofuran(200 mL) at 0° C. under nitrogen was added sodium borohydride (0.594 g, 15.7 mmol). After stirring at 0° C. for 1 hr, the mixture was concentrated and the residue partitioned between EtOAc-half saturated $NH_4Cl$ solution. The organic phase was washed with saturated $NaHCO_3$ and saturated NaCl solutions, dried over anhydrous $Na_2SO_4$ and evaporated to a dryness. The residue was purified by flash chromatography on silica gel eluting with EtOAc-hexane (1:3) to give the title compound (7.99 g, 87%) as a white solid. TLC(EtOAc-hexane; 1:1) Rf=0.54.

Part E: (3S,4RS)-3-(Valinyl)Amino-5-(2',3',5',6'-Tetrafluorophenoxy)-4-Hydroxypentanoic Acid tert-Butyl Ester To a solution of (3S,4RS)-3-[(N-benzyloxycarbonyl)valinyl]amino-5-(2',3',5',6'-tetrafluorophenoxy)-4-hydroxypentanoic acid tert-butyl ester (7.99 g, 13.6 mmol) in MeOH (130 mL) was added 10% Pd—C (0.80 g) and resulting mixture stirred under a hydrogen atmosphere (balloon) for 2 hrs. The mixture was filtered through Celite washing the filter cake with $CH_2Cl_2$ and the combined filtrates evaporated to dryness. The residue purified by flash chromatography on silica gel eluting with EtOAc-hexane (1:3) then methanol to give the title compound (5.13 g, 83%) as a viscous oil. TLC(EtOAc-hexane; 1:1) Rf=0.07.

Part F: (3S,4RS)-3-[N-(N'-(1-Naphthylmethyl)Oxamyl) Valinyl]Amino-5-(2',3',5',6'-Tetrafluorophenoxy)-4-Hydroxypentanoic Acid tert-Butyl Ester To a solution of N-(1-naphthylmethyl)oxamic acid (0.051 g, 0.22 mmol, prepared from 1-naphthylmethylamine by the method described in Example 1, Part A) in N-methylpyrrolidone(1.0 mL)-$CH_2Cl_2$(1.0 mL) at room temperature under nitrogen was added O-(7-azabenzotriazol-1-yl)-N,N,N',N'-tetramethyluronium hexafluorophate (0.092 g, 0.24 mmol). After stirring for 15 min, the mixture was treated with (3S,4RS)-3-(valinyl)amino-5-(2',3',5',6'-tetrafluorophenoxy)-4-hydroxypentanoic acid tert-butyl ester (0.100 g, 0.22 mmol) and diisopropylethylamine (115 μL, 0.66 mmol). After stirring at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to give the crude title compound (0.157 g, 100%) as a viscous oil. TLC(EtOAc-hexane; 1:1) Rf=0.44.

Part G: (3S)-3-[N-(N'-(1-Naphthylmethyl)Oxamyl) Valinyl]Amino-5-(2',3',5',6'-Tetrafluorophenoxy)-4-Oxopentanoic Acid tert-Butyl Ester To a solution of (3S,4RS)-3-[N-(N'-(1-naphthylmethyl) oxamyl)valinyl]-amino-5-(2',3',5',6'-tetrafluorophenoxy)-4-hydroxypentanoic acid tert-butyl ester (0.157 g, ca 0.22 mmol) in dimethylsulfoxide (5 mL) at room temperature under nitrogen was added Dess-Martin Periodinane (0.600 g, 1.42 mmol). After stirring at room temperature for 16 hrs, the mixture was partitioned between EtOAc-water. The organic phase was washed with saturated $NaHCO_3$ and saturated NaCl solutions, dried over anhydrous $Na_2SO_4$ and evaporated to a dryness. The residue (0.175 g) was purified by flash chromatography on silica gel eluting with EtOAc-hexane (3:7) to give the title compound (0.111 g, 77%) as a white solid. TLC(EtOAc-hexane; 1:1) Rf=0.58.

Part H: (3S)-3-[N-(N'-(1-Naphthylmethyl)Oxamyl) Valinyl]Amino-5-(2',3',5',6'-Tetrafluorophenoxy)-4-Oxopentanoic Acid To a solution of (3S)-3-[N-(N'-(1-naphthylmethyl)oxamyl)valinyl]amino-5-(2',3',5',6'-tetrafluorophenoxy)-4-oxopentanoic acid, tert-butyl ester (0.108 g, 0.16 mmol) in $CH_2Cl_2$(2.0 mL)-anisole(0.1 mL)-water(0.05 mL) at room temperature under nitrogen was added trifluoroacetic acid (2.0 mL). The resulting clear solution was stirred at room temperature for 2 hr, evaporated to dryness and chased with toluene-$CH_2Cl_2$ (1:1). The residue was triturated with $Et_2O$ to give the title compound (0.098 g, 100%) as a white solid. MS(ES) for $C_{29}H_{27}F_4N_3O_7$ (MW 605.54): positive 628(M+Na); negative 604(M−H).

EXAMPLES 79–125

Starting with (3S,4RS)-3-(valinyl)amino-5-(2',3',5',6'-tetrafluorophenoxy)-4-hydroxypentanoic acid tert-butyl ester (see Example 78, Part E) and following the methods described in Example 78, Parts F through H, the compounds shown below in Table 6 were also prepared:

TABLE 6

|  |  |  |  | MS(ES) | |
|---|---|---|---|---|---|
| Ex. | R[1] | Formula | MW | pos. | neg. |
| 79 | $PhCH_2$ | $C_{25}H_{25}F_4N_3O_7$ | 555.48 | 556(M+H) 578(M+Na) | 554(M−H) |
| 80 | $Ph(CH_2)_2$ | $C_{26}H_{27}F_4N_3O_7$ | 569.51 | 592(M+Na) | 568(M−H) |
| 81 | $Ph_2CH$ | $C_{31}H_{29}F_4N_3O_7$ | 631.58 | 654(M+Na) | 630(M−H) |
| 82 | Ph | $C_{24}H_{23}F_4N_3O_7$ | 541.46 | 564(M+Na) | 540(M−H) |
| 83 | (2-Ph)Ph | $C_{30}H_{27}F_4N_3O_7$ | 617.55 | 640(M+Na) | 616(M−H) 730(M+TFA) |
| 84 | (2-$PhCH_2$)Ph | $C_{31}H_{29}F_4N_3O_7$ | 631.58 | 654(M+Na) | 630(M−H) |
| 85 | (3-PhO)Ph | $C_{30}H_{27}F_4N_3O_8$ | 633.55 | 634(M+H) 656(M+Na) | 632(M−H) |
| 86 | 4-Cl-1-naphthyl | $C_{28}H_{24}ClF_4N_3O_7$ | 625.96 | 648/650(M+Na) | 624/626(M−H) |
| 87 | 2-anthryl | $C_{32}H_{27}F_4N_3O_7$ | 641.57 | 642(M+H) | 640(M−H) |
| 88 | 2-benzimidazolyl | $C_{25}H_{23}F_4N_5O_7$ | 581.48 | 582(M+H) 604(M+Na) | 580(M−H) |
| 89 | 1-adamantanyl | $C_{28}H_{33}F_4N_3O_7$ | 599.58 | 600(M+H) | 598(M−H) |
| 90 | (2-F)Ph | $C_{24}H_{22}F_5N_3O_7$ | 559.45 | 582(M+Na) | 558(M−H) 672(M+TFA) |
| 91 | (4-F)Ph | $C_{24}H_{22}F_5N_3O_7$ | 559.45 | 582(M+Na) | 558(M−H) 672(M+TFA) |
| 92 | (2-$CF_3$)Ph | $C_{25}H_{22}F_7N_3O_7$ | 609.45 | 632(M+Na) | 608(M−H) 722(M+TFA) |
| 93 | (2-t-Bu)Ph | $C_{28}H_{31}F_4N_3O_7$ | 597.56 | 620(M+Na) | 596(M−H) 710(M+TFA) |
| 94 | (4-n-heptyl)Ph | $C_{31}H_{37}F_4N_3O_7$ | 639.64 | 662(M+Na) | 638(M−H) |
| 95 | (2-$CH_3O$)Ph | $C_{25}H_{25}F_4N_3O_8$ | 571.48 | 594(M+Na) | 570(M−H) |
| 96 | (2-PhO)Ph | $C_{30}H_{27}F_4N_3O_8$ | 633.55 | 656(M+Na) | 632(M−H) 746(M+TFA) |
| 97 | 2-naphthyl | $C_{28}H_{25}F_4N_3O_7$ | 591.51 | 614(M+Na) | 590(M−H) |
| 98 | 5,6,7,8-tetrahydro-1-naphthyl | $C_{28}H_{29}F_4N_3O_7$ | 595.55 | 618(M+Na) | 594(M−H) |
| 99 | 1-anthryl | $C_{32}H_{27}F_4N_3O_7$ | 641.57 | 664(M+Na) | 640(M−H) |
| 100 | 2-pyridinyl | $C_{23}H_{22}F_4N_4O_7$ | 542.44 | 543(M+H) | 541(M−H) |
| 101 | 4-pyridinyl | $C_{23}H_{22}F_4N_4O_7$ | 542.44 | 543(M+H) | 541(M−H) |
| 102 | 2,3,5,6-tetrafluoro-4-pyridinyl | $C_{23}H_{18}F_8N_4O_7$ | 614.40 | 615(M+H) | 613(M−H) |
| 103 | 2-pyrazinyl | $C_{22}H_{21}F_4N_5O_7$ | 543.43 | 544(M+H) | 542(M−H) |
| 104 | 1,2,3,4-tetrahydro-1-naphthyl | $C_{28}H_{29}F_4N_3O_7$ | 595.55 | 596(M+H) 618(M+Na) 634(M+K) | 594(M−H) 708(M+TFA) |
| 105 | (2-Cl)Ph | $C_{24}H_{22}ClF_4N_3O_7$ | 575.90 | 598/600(M+Na) | 574/576(M−H) |
| 106 | (2-Br)Ph | $C_{24}H_{22}BrF_4N_3O_7$ | 620.35 | 644/642(M+Na) | 620/618(M−H) 734/732(M+TFA) |
| 107 | (2-I)Ph | $C_{24}H_{22}F_4IN_3O_7$ | 667.35 | 690(M+Ma) 706(M+K) | 666(M−H) 780(M+TFA) |
| 108 | (2,6-di-F)Ph | $C_{24}H_{22}F_6N_3O_7$ | 577.44 | 600(M+Na) | 576(M−H) 690(M+TFA) |
| 109 | (2,5-di-t-Bu)Ph | $C_{32}H_{39}F_4N_3O_7$ | 653.67 | 654(M+H) 676(M+Na) 692(M+K) | 652(M−H) 688(M+Cl) 766(M+TFA) |
| 110 | 5-indanyl | $C_{27}H_{27}F_4N_3O_7$ | 581.52 | 604(M+Na) 620(M+K) | 580(M−H) 694(M+TFA) |
| 111 | (3,4,5-tri-MeO)$PhCH_2$ | $C_{28}H_{31}F_4N_3O_{10}$ | 645.56 | 646(M+H) 668(M+Na) 684(M+K) | 644(M−H) |

TABLE 6-continued

![structure with R1-NH-C(O)-C(O)-NH-CH(iPr)-C(O)-NH-CH(CO2H)-C(O)-CH2-O-C6F4]

| Ex. | R¹ | Formula | MW | MS(ES) pos. | MS(ES) neg. |
|---|---|---|---|---|---|
| 112 | methyl | $C_{19}H_{21}F_4N_3O_7$ | 479.38 | 502(M+Na) | 478(M−H)<br>592(M+TFA) |
| 113 | n-heptyl | $C_{25}H_{33}F_4N_3O_7$ | 563.55 | 586(M+Na)<br>602(M+K) | 562(M−H)<br>676(M+TFA) |
| 114 | t-octyl | $C_{26}H_{35}F_4N_3O_7$ | 577.57 | 600(M+Na) | 576(M−H) |
| 115 | cyclo-hexyl | $C_{24}H_{29}F_4N_3O_7$ | 547.50 | 548(M+H)<br>570(M+Na)<br>586(M+K) | 546(M−H)<br>660(M+TFA) |
| 116 | 5-Ph-3-pyrazolyl | $C_{27}H_{25}F_4N_5O_7$ | 607.52 | 630(M+Na)<br>646(M+K) | 606(M−H) |
| 117 | (2-F-4-I)Ph | $C_{24}H_{21}F_5IN_3O_7$ | 685.34 | 686(M+H)<br>708(M+Na)<br>724(M+K) | 684(M−H)<br>720(M+Cl) |
| 118 | (2,3,4,5-tetra-F)Ph | $C_{24}H_{19}F_8N_3O_7$ | 613.41 | 614(M+H)<br>636(M+Na)<br>652(M+K) | 612(M−H)<br>726(M+TFA) |
| 119 | (2,3,4,6-tetra-F)Ph | $C_{24}H_{19}F_8N_3O_7$ | 613.41 | 614(M+H)<br>636(M+Na)<br>652(M+K) | 612(M−H)<br>726(M+TFA) |
| 120 | (2,3,5,6-tetra-Cl)Ph | $C_{24}H_{19}Cl_4F_4N_3O_7$ | 679.23 | 700/702/704(M+Na)<br>716/718/720(M+K) | 676/678/680(M−H)<br>790/792/794(M+TFA) |
| 121 | (2,3,4,5,6-penta-F)Ph | $C_{24}H_{18}F_9N_3O_7$ | 631.40 | 654(M+Na)<br>670(M+K) | 630(M−H)<br>666(M+Cl) |
| 122 | Ph₂N | $C_{30}H_{28}F_4N_4O_7$ | 632.57 | 633(M+H)<br>655(M+Na) | 631(M−H)<br>745(M+TFA) |
| 123 | PHCH₂(Ph)N | $C_{31}H_{30}F_4N_4O_7$ | 646.59 | 647(M+H)<br>669(M+Na)<br>685(M+K) | 645(M−H)<br>681(M+Cl) |
| 124 | PhCH₂O | $C_{25}H_{25}F_4N_3O_7$ | 571.48 | 594(M+Na) | 570(M−H)<br>684(M+TFA) |
| 125 | 5-quinolinyl | $C_{29}H_{25}F_7N_4O_9$ | 706.53 | 593(M+H) | 591(M−H) |

EXAMPLE 126

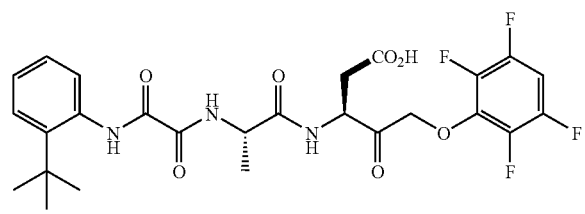

(3S)-3-[N-(N'-(2-TERT-BUTYLPHENYL)OXAMYL)ALANINYL]AMINO-5-(2',3',5',6'-TETRAFLUOROPHENOXY)-4-OXOPENTANOIC ACID

Part A: [(N-Benzyloxycarbonyl)Alaninyl]Aspartic Acid, β-tert-Butyl Ester

To a suspension of aspartic acid β-tert-butyl ester (3.784 g, 20 mmol) in dimethylformamide (150 mL) at room temperture under nitrogen was added bis(trimethylsilyl)-trifluoroacetamide (10.6 mL, 40 mmol). After stirring at room temperature for 30 min, the resulting clear solution was treated with (N-benzyloxycarbonyl)alanine N-hydroxysuccinimide ester (6.406 g, 20 mmol). After stirring at room temperature for an additional 48 hrs, the mixture was treated with water (20 mL), stirred for 15 min and then partitioned between EtOAc/water. The organic phase was washed with water, 5% KHSO₄ and saturated NaCl solutions, dried over anhydrous Na₂SO₄ and evaporated to a dryness. The residue was dissolved in Et₂O and extracted with saturated NaHCO₃. The aqueous extract was acidified (pH 2.0) with concentrated HCl and extracted with EtOAc. The EtOAc extract was washed with saturated NaCl solution, dried over anhydrous Na₂SO₄ and evaporated to a give the title compound (6.463 g, 82%) as a white foam. TLC (EtOAc-hexane-AcOH; 70:30:2) Rf=0.50.

Part B: (3S,4RS)-3-(Alaninyl)Amino-5-(2',3',5',6'-Tetrafluorophenoxy)-4-Hydroxypentanoic Acid tert-Butyl Ester Starting with [(N-benzyloxycarbonyl)alaninyl]aspartic acid, β-tert-butyl ester and following the methods described in Example 28, Parts B through E gave the title compound as a colorless, viscous oil. TLC(EtOAc-hexane; 1:1) Rf=0.06.

Part C: (3S,4RS)-3-[N-(N'-(2-tert-Butylphenyl)Ox-amyl) Alaninyl]Amino-5-(2',3',5',6'-Tetrafluorophe-noxy)-4-Hydroxypentanoic Acid tert-Butyl Ester To a solution of N-(2-tert-butylphenyl)oxamic acid (0.041 g, 0.19 mmol, prepared from 2-tert-butylaniline by the method described in Example 1, Part A) in CH$_2$Cl$_2$(6.0 mL) at 0° C. under nitrogen was added hydroxybenzotriazole hydrate (0.030 g) followed by 1-ethyl-3-(3',3'-dimethyl-1'-aminopropyl)-carbodiimide hydrochloride (0.050 g, 0.26 mmol). After stirring at 0° C. for 10 min, the mixture was treated with (3S,4RS)-3-(alaninyl)amino-5-(2',3',5',6'-tetrafluorophenoxy)-4-hydroxypentanoic acid tert-butyl ester (0.079 g, 0.19 mmol) and N-methylmorpholine (22 μL, 0.20 mmol). After stirring at room temperature for 16 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to give the crude title compound (0.090 g, 77%) as a viscous oil. TLC(EtOAc-hexane; 1:1) Rf=0.70.

Part D: (3S)-3-[N-(N'-(2-tert-Butylphenyl)Oxamyl) Alaninyl]Amino-5-(2',3',5',6'-Tetrafluorophenoxy)-4-Oxopentanoic Acid tert-Butyl Ester To a solution of (3S,4RS)-3-[N-(N'-(2-tert-butylphenyl)oxamyl)alaninyl]amino-5-(2',3',5',6'-tetrafluorophenoxy)-4-hydroxypentanoic acid tert-butyl ester (0.0.092 g, ca 0.15 mmol) in CH$_2$Cl$_2$ (6.5 mL) at room temperature under nitrogen was added iodobenzene diacetate (0.188 g, 0.58 mmol) followed by a catalytic amount of 2,2,6,6-tetramethyl-1-piperidinyloxy free radical (TEMPO, 0.0046 g, 0.03 mmol). After stirring at room temperature for 16 hrs, the mixture was partitioned between EtOAc-water. The organic phase was washed with saturated NaHCO$_3$ and saturated NaCl solutions, dried over anhydrous Na$_2$SO$_4$ and evaporated to a dryness. The residue (0.096 g) was purified by preparative layer chromatography on silica gel eluting with EtOAc-hexane (3:7) to give the title compound (0.071 g, 77%) as a colorless glass. TLC(EtOAc-hexane; 2:3) Rf=0.60.

Part E: (3S)-3-[N-(N'-(2-tert-Butylphenyl)Oxamyl) Alaninyl]Amino-5-(2',3',5',6'-Tetrafluorophenoxy)-4-Oxopentanoic Acid To a solution of (3S)-3-[N-(N'-(2-tert-butylphenyl)oxamyl)alaninyl]amino-5-(2',3',5',6'-tetrafluorophenoxy)-4-oxopentanoic acid, tert-butyl ester (0.071 g, 0.11 mmol) in CH$_2$Cl$_2$(2.5 mL)-anisole(0.05 mL) at room temperature under nitrogen was added trifluoroacetic acid (1.5 mL). The resulting clear solution was stirred at room temperature for 1 hr, evaporated to dryness and chased with toluene-CH$_2$Cl$_2$ (1:1). The residue (0.061 g) was purified by preparative layer chromatography on silica gel eluting with MeOH—CH$_2$Cl$_2$ (1:9) to give the title compound (0.044 g, 69%) as a colorless glass. MS(ES) for C$_{26}$H$_{27}$F$_4$N$_3$O$_7$ (MW 569.51): positive 570(M+H); negative 568(M−H).

EXAMPLES 127–178

Starting with (3S,4RS)-3-(alaninyl)amino-5-(2',3',5',6'-tetrafluorophenoxy)-4-hydroxypentanoic acid tert-butyl ester (see Example 79, Part B) and following the methods described in Example 79, Parts C through E, the compounds shown below in Table 7 were also prepared:

TABLE 7

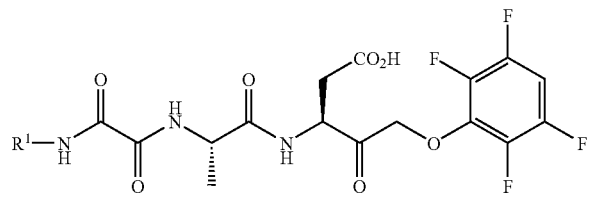

| Ex. | R$^1$ | Formula | MW | MS(ES) pos. | MS(ES) neg. |
|---|---|---|---|---|---|
| 127 | (2-CF$_3$)Ph | C$_{23}$H$_{18}$F$_7$N$_3$O$_7$ | 581.40 | 604(M+Na) | 580(M−H) |
| 128 | (2-Ph)Ph | C$_{28}$H$_{23}$F$_4$N$_3$O$_7$ | 589.50 | 612(M+Na) | 588(M−H) |
| 129 | (2-PhCH$_2$)Ph | C$_{29}$H$_{25}$F$_4$N$_3$O$_7$ | 603.53 | 604(M+H) | 602(M−H) |
| 130 | (2-PhO)Ph | C$_{28}$H$_{23}$F$_4$N$_3$O$_8$ | 605.50 | 628(M+Na) | 604(M−H) |
| 131 | (3-PhO)Ph | C$_{28}$H$_{23}$F$_4$N$_3$O$_8$ | 605.50 | 628(M+Na) | 604(M−H) |
| 132 | 5,6,7,8-tetrahydro-1-naphthyl | C$_{26}$H$_{25}$F$_4$N$_3$O$_7$ | 567.49 | 590(M+Na) | 566(M−H) |
| 133 | 1-naphthyl | C$_{26}$H$_{21}$F$_4$N$_3$O$_7$ | 563.46 | 586(M+Na) 608(M+K) | 562(M−H) |
| 134 | Ph | C$_{22}$H$_{19}$F$_4$N$_3$O$_7$ | 513.40 | 552(M+K) | 512(M−H) |
| 135 | (2,6-di-F)Ph | C$_{22}$H$_{17}$F$_6$N$_3$O$_7$ | 549.38 | 572(M+Na) | 548(M−H) 662(M+TFA) |
| 136 | (4-Ph)Ph | C$_{28}$H$_{23}$F$_4$N$_3$O$_7$ | 589.50 | — | 588(M−H) |
| 137 | (4-MeO)Ph | C$_{23}$H$_{21}$F$_4$N$_3$O$_8$ | 543.43 | 582(M+K) | 542(M−H) |
| 138 | Ph$_2$CH | C$_{29}$H$_{25}$F$_4$N$_3$O$_7$ | 603.53 | 642(M+K) | 602(M−H) |
| 139 | 4-pyridinyl | C$_{22}$H$_{20}$F$_4$N$_4$O$_9$ | 560.42 | 515(M+H) | 513(M+H) |
| 140 | 2-pyridinyl | C$_{21}$H$_{18}$F$_4$N$_4$O$_7$ | 514.39 | 515(M+H) | |
| 141 | (2-Cl)Ph | C$_{22}$H$_{18}$ClF$_4$N$_3$O$_7$ | 547.85 | | |
| 142 | (2,3,4,5-tetra-Cl)Ph | C$_{22}$H$_{15}$F$_8$N$_3$O$_7$ | 585.36 | | 584(M−H) |
| 143 | 5-indanyl | C$_{25}$H$_{23}$F$_4$N$_3$O$_7$ | 553.47 | | 552(M−H) |
| 144 | (2-Br)Ph | C$_{22}$H$_{18}$BrF$_4$N$_3$O$_7$ | 592.30 | | 590/592(M−H) |

TABLE 7-continued

| Ex. | R¹ | Formula | MW | MS(ES) pos. | MS(ES) neg. |
|---|---|---|---|---|---|
| 145 | (2,3,5,6-tetra-F)Ph | $C_{22}H_{15}ClF_4F_4N_3O_7$ | 651.18 | | 648/650/652 (M−H) |
| 146 | 1-anthryl | $C_{30}H_{23}F_4N_4O_7$ | 613.52 | 636(M+Na) | 612(M−H) |
| 147 | PhCH₂ | $C_{23}H_{21}F_4N_3O_7$ | 527.43 | | |
| 148 | Ph(CH₂)₂ | $C_{24}H_{23}F_4N_3O_7$ | 541.46 | 542(M+H) 564(M+Na) | 540(M−H) |
| 149 | (2-F)Ph | $C_{22}H_{18}F_5N_3O_7$ | 531.39 | 554(M+Na) | 530(M−H) |
| 150 | (4-F)Ph | $C_{22}H_{18}F_5N_3O_7$ | 531.39 | 554(M+Na) | 530(M−H) |
| 151 | (2-pyrrolidin-1-yl)Ph | $C_{28}H_{27}F_7N_4O_9$ | 696.53 | 583(M+H) | 581(M−H) 695(M+TFA) |
| 152 | (2-morpholin-4-yl)Ph | $C_{28}H_{27}F_7N_4O_{10}$ | 712.53 | 599(M+H) | 597(M−H) 711(M+TFA) |
| 153 | (2-morpholin-4-yl-5-trifluoromethyl)Ph | $C_{29}H_{26}F_{10}N_4O_{10}$ | 780.53 | 689(M+Na) | 664(M−H) |
| 154 | (2-pyrrolidin-1-yl-5-trifluoromethyl)Ph | $C_{29}H_{26}F_{10}N_4O_9$ | 764.53 | 651(M+H) 673(M+Na) | 649(M−H) |
| 155 | PhCH₂ | $C_{23}H_{21}F_4N_3O_7$ | 527.43 | 594(M+Na) | 590(M−H) |
| 156 | Adamantan-1-yl | $C_{26}H_{29}F_4N_3O_7$ | 571.52 | 594(M+Na) | 570(M−H) |
| 157 | cyclo-hexyl | $C_{22}H_{25}F_4N_3O_7$ | 519.45 | 558(M+K) | 518(M−H) |
| 158 | (2-Cl)Ph | $C_{22}H_{18}ICF_4N_3O_7$ | 547.85 | 570/572 (M+Na) | 546/548(M−H) |
| 159 | (2,5-di-t-Bu) | $C_{30}H_{35}F_4N_3O_7$ | 625.61 | | |
| 160 | 1,2,3,4-tetrahydro-naphthalen-1-yl | $C_{26}H_{25}F_4N_3O_7$ | 567.49 | 590(M+Na) | 566(M−H) |
| 161 | (4-n-heptyl)Ph | $C_{29}H_{33}F_4N_3O_7$ | 611.49 | 634(M+Na) | 610(M−H) |
| 162 | (2-1)Ph | $C_{22}H_{18}F_4IN_3O_7$ | 639.30 | 662(M+Na) | 638(M−H) |
| 163 | napthalen-1yl-methyl | $C_{27}H_{23}F_4N_3O_7$ | 577.49 | 600(M+Na) | 576(M−H) |
| 164 | pyrrolidin-1-yl | $C_{20}H_{22}F_4N_4O_7$ | 506.14 | 507.22 (M+H) | |
| 165 | 1-pyrrolidine | $C_{20}H_{21}F_4N_3O_7$ | 491.13 | | 509(M+NH₄) 492(M+H) |
| 166 | 1-piperidine | $C_{21}H_{23}F_4N_3O_7$ | 505.15 | 504(M+H) | |
| 167 | piperidin-1-yl | $C_{23}H_{28}F_4N_4O_9$ | 580.18 | | 519(M−H) |
| 168 | (2-tBu-5-AcNH)Ph | $C_{28}H_{30}F_4N_4O_8$ | 626.2 | | 625(M−H) |
| 169 | (2-tBu-5-NH(CO(CH₂)₃NHGmoc)Ph | $C_{45}H_{45}F_4N_5O_{10}$ | 891.31 | | 890(M−H) |
| 170 | (2,3,5,6-tetra-F)Ph | $C_{21}H_{16}F_8N_4O_6$ | 572.09 | 573(M+H) | |
| 171 | (2-(3-CH₃O-Ph))Ph | $C_{29}H_{25}F_4N_3O_8$ | 619.16 | 642(M+Na) | 618(M−H) |
| 172 | (2-(4-CH₃O-Ph))Ph | $C_{29}H_{25}F_4N_3O_8$ | 619.16 | 620(M+H) | 618(M−H) |
| 173 | (2-(2-CH₃O-Ph))Ph | $C_{29}H_{25}F_4N_3O_8$ | 619.16 | 620(M+H) | 618(M−H) |
| 174 | (2-(1-naphthyl))Ph | $C_{32}H_{25}F_4N_3O_7$ | 639.55 | 662(M+Na) | 638(M−H) |
| 175 | [2-{(3-CH₃)Ph}]Ph | $C_{29}H_{25}F_4N_3O_7$ | 603.19 | 626(M+Na) | 602(M−H) |
| 176 | [2-{(4-CH₃)Ph}]Ph | $C_{29}H_{25}F_4N_3O_7$ | 603.19 | 626(M+Na) | 602(M−H) |
| 177 | [2-{(2-CH₃)Ph}]Ph | $C_{29}H_{25}F_4N_3O_7$ | 603.19 | 626(M+Na) | 602(M−H) |

EXAMPLE 178

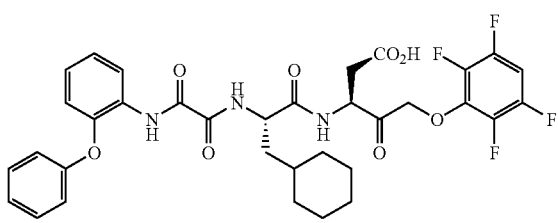

(3S)-3-[N-(N'-(2'-Phenoxyphenyl)Oxamyl)Cyclohexylalaninyl]Amino-5-(2',3',5',6'-Tetrafluorophenoxy)-4-Oxopentanoic Acid Part A: (3S)-3-(N-Benzyloxycarbonyl)Amino-5-Bromo-4-Oxopentanoic Acid tert-Butyl Ester A solution of (N-benzyloxycarbonyl)aspartic acid, β-tert-butyl ester (2.28 g, 7.06 mmol) and N-methylmorpholine (0.85 mL, 7.7 mmol) in tetrahydrofuran (40 mL) at −10° C. (NaCl/ice bath) under nitrogen was treated dropwise via syringe with isobutyl chloroformate (1.1 mL, 8.5 mmol). After stirring at −10° C. for 20 min, the mixture was filtered (sinctered glass) into a pre-cooled receiver (ice bath) washing the filter cake with additional tetrahydrofuran (approx. 10 mL). The combined filtrate was treated with excess diazomethane/Et₂O solution (prepared from 3.10 g, 21 mmol of 1-methyl-3-nitro-1-nitrosoguanidine, 20 mL 40%

KOH/10 ml Et$_2$O) at 0° C. (ice bath) under nitrogen. After stirring at 0° C. for 15 min and at room temperature for 30 min, the reaction mixture was again cooled to 0° C. and treated with 48% HBr(2.0 mL, 12 mmol)/acetic acid(2.0 mL). After stirring at 0° C. for 15 min and at room temperature for 15 min, the mixture was partitioned between EtOAc-water. The organic phase was washed with water, saturated NaHCO$_3$, and saturated NaCl solutions dried over anhydrous Na$_2$SO$_4$ and evaporated to a dryness. Trituration with hexane gave the crude title compound (3.32 g) as a yellow oil. TLC(EtOAc-hexane; 1:1) Rf=0.60 (intermediate diazoketone Rf=0.52).

Part B: (3S,4RS)-3-W-Benzyloxycarbonyl)Amino-5-(2',3',5',6'-Tetrafluorophenoxy)-4-Hydroxypentanoic Acid tert-Butyl Ester To a solution of (3S)-3-(N-benzyloxycarbonyl)amino-5-bromo-4-oxopentanoic acid tert-butyl ester (0.857 g, 2.14 mmol) and 2,3,5,6-tetrafluorophenol (0.410 g, 2.45 mmol) in dimethylformamide (5.0 mL) at room temperature under nitrogen was added potassium fluoride (0.40 g, 6.9 mmol). After stirring at room temperature for 16 hrs, the mixture was diluted with EtOAc, washed with saturated NaHCO$_3$ and saturated NaCl solutions, dried over anhydrous Na$_2$SO$_4$ and evaporated to a to give the crude tetrafluorophenoxymethyl ketone (1.08 g, 98%) as a yellow, viscous oil. TLC (EtOAc-hexane; 1:1) Rf=0.57.

To a solution of the above crude ketone (1.08 g, ca 2.14 mmol) in ethanol (10 mL) at 0° C. under nitrogen was added sodium borohydride (0.057 g, 1.5 mmol). After stirring at 0° C. for 1 hr, the excess reducing agent was discharged by treatment with acetone (1.0 mL), the mixture concentrated and the residue partitioned between EtOAc-half saturated NH$_4$Cl solution. The organic phase was washed with saturated NaHCO$_3$ and saturated NaCl solutions, dried over anhydrous Na$_2$SO$_4$ and evaporated to a dryness. The residue was purified by flash chromatography on silica gel eluting with EtOAc-hexane (1:3) to give the title compound (1.012 g, 94%) as a colorless oil. TLC(EtOAc-hexane; 1:1) Rf=0.48.

Part C: (3S,4RS)-3-[(N-9-Fluorenylmethoxycarbonyl)Cyclohexylalaninyl]Amino-5-(2',3',5',6'-Tetrafluorophenoxy)-4-Hydroxypentanoic Acid tert-Butyl Ester To a solution of (3S,4RS)-3-(N-benzyloxycarbonyl) amino-5-(2',3',5',6'-tetrafluorophenoxy)-4-hydroxypentanoic acid tert-butyl ester (1.012 g, 2.08 mmol) in MeOH (25 mL) was added 10% Pd—C (0.30 g) and resulting mixture stirred under a hydrogen atmosphere (balloon) for 4 hrs. The mixture was filtered through Celite washing the filter cake with CH$_2$Cl$_2$ and the combined filtrates evaporated to give the crude amine (0.682 g, 93%) as a viscous oil. TLC(MeOH—CH$_2$Cl$_2$; 5:95) Rf=0.21.

To a solution of (N-9-fluorenylmethoxycarbonyl)cyclohexylalanine (0.763 g, 1.94 mmol) in CH$_2$Cl$_2$(10 mL) at 0° C. (ice bath) under nitrogen was added hydroxybenzotriazole hydrate (0.282 g) followed by 1-ethyl-3-(3',3'-dimethyl-1'-aminopropyl)carbodiimide hydrochloride (0.447 g, 2.33 mmol). After stirring at 0° C. for 10 min, the mixture was treated with the above crude amine (0.682 g, ca 1.93 mmol) and the reaction allowed to warm to room temperature. After stirring at room temperature for 3 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. The residue was purified by flash chromatography eluting with EtOAc-hexane (1:2) to give the title compound (1.028 g, 73%) as yellow foam. TLC (EtOAc-hexane; 1:2) Rf=0.20.

Part D: (3S,4RS)-3-[Cyclohexylalaninyl]Amino-5-(2',3',5',6'-Tetrafluorophenoxy)-4-Hydroxypentanoic Acid tert-Butyl Ester A mixture of (3S,4RS)-3-[(N-9-fluorenylmethoxycarbonyl)cyclohexylalaninyl]amino-5-(2',3',5',6'-tetrafluorophenoxy)4-hydroxypentanoic acid tert-butyl ester (1.028 g, 1.4 mmol) and 10% piperidine/dimethylformamide (3.0 mL) was stirred at room temperature under nitrogen for 2 hrs. The mixture was diluted with CH$_2$Cl$_2$, washed with water and saturated NaHCO$_3$ solution, dried over anhydrous Na$_2$SO$_4$ and evaporated to dryness. The residue was purified by flash chromatography eluting with isopropanol-CH$_2$Cl$_2$ (7:93) to give the title compound (0.561 g, 78%) as a white solid. TLC(MeOH—CH$_2$Cl$_2$; 5:95) Rf=0.43.

Part E: (3S,4RS)-3 [N-(N'-(2'-Phenoxyphenyl)Oxamyl)Cyclohexylalaninyl]-Amino-5-(2',3',5',6'-Tetrafluorophenoxy)-4-Hydroxypentanoic Acid tert-Butyl Ester To a solution of N-(2-phenoxyphenyl)oxamic acid (0.064 g, 0.25 mmol, prepared from 2-phenoxyaniline by the method described in Example 1, Part A) and (3S,4RS)-3-[cyclohexylalaninyl]amino-5-(2',3',5',6'-tetrafluorophenoxy)-4-hydroxypentanoic Acid tert-butyl ester (0.124 g, 0.245 mmol) in CH$_2$Cl$_2$(5.0 mL) at 0° C. (ice bath) under nitrogen was added hydroxybenzotriazole hydrate (0.051 g) followed by 1-ethyl-3-(3',3'-dimethyl-1'-aminopropyl)carbodiimide hydrochloride (0.061 g, 0.32 mmol). After stirring at 0° C. for 10 min and at room temperature for 18 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to give the crude title compound (0.194 g) as yellow foam. TLC(EtOAc-hexane; 1:2) Rf=0.40.

Part F: (3S)-3-[N-(N'-(2'-Phenoxyphenyl)Oxamyl)Cyclohexylalaninyl]-Amino-5-(2',3',5',6'-Tetrafluorophenoxy)-4-Oxoxypentanoic Acid tert-Butyl Ester To a solution of crude (3S,4RS)-3-[N-(N'-(2'-phenoxyphenyl)oxamyl) cyclohexylalaninyl]amino-5-(2',3',5',6'-tetrafluorophenoxy)-4-hydroxypentanoic acid tert-butyl ester (0.194 g, ca 0.245 mmol) in CH$_2$Cl$_2$ (5 mL) at room temperature under nitrogen was added Dess-Martin Periodinane (0.150 g, 0.35 mmol). After stirring at room temperature for 2 hrs, the mixture was diluted with EtOAc, washed with 1.0 M Na$_2$S$_2$O$_3$, saturated NaHCO$_3$ and saturated NaCl solutions, dried over anhydrous Na$_2$SO$_4$ and evaporated to a dryness. The residue was purified by flash chromatography on silica gel eluting with EtOAc-hexane (1:3) to give the title compound (0.142 g, 80%) as a colorless, viscous oil. TLC(EtOAc-hexane; 1:2) Rf=0.50.

Part G: (3S)-3-[N-(N'-(2'-Phenoxyphenyl)Oxamyl) Cyclohexylalaninyl]-Amino-5-(2',3',5',6'-Tetrafluorophenoxy)-4-Oxoxypentanoic Acid To a solution of (3S)-3-[N-(N'-(2'-phenoxyphenyl)oxamyl)cyclohexylalaninyl]amino-5-(2',3',5',6'-tetrafluorophenoxy)-4-oxopentanoic acid, tert-butyl ester (0.142 g, 0.19 mmol) in $CH_2Cl_2$(2.0 mL) at room temperature under nitrogen was added trifluoroacetic acid (1.0 mL). The resulting clear solution was stirred at room temperature for 0.5 hr, evaporated to dryness and chased with toluene-$CH_2Cl_2$ (1:1) to give the title compound (0.123 g, 93%) as a white foam. MS(ES) for $C_{34}H_{33}F_4N_3O_8$ (MW 687.64): positive 688(M+H), 710(M+Na), 726(M+K); negative 686(4-H), 800(M+TFA).

EXAMPLES 179–181

Starting with (3S,4RS)-3-[cyclohexylalaninyl]amino-5-(2',3',5',6'-tetrafluoro-phenoxy)-4-hydroxypentanoic acid tert-butyl ester (see Example 178, Part D) and following the methods described in Example 178, Parts E through G the compounds shown below in Table 8 were also prepared:

TABLE 8

| Ex. | R1 | Formula | MW | MS(ES) pos. | MS(ES) neg. |
|---|---|---|---|---|---|
| 179 | (2-Ph)Ph | $C_{34}H_{33}F_4N_3O_7$ | 671.64 | 672(M+H) 694(M+Na) | 670(M–H) 784 (M+TFA) |
| 180 | (2-PhCH$_2$)Ph | $C_{35}H_{35}F_4N_3O_7$ | 685.67 | 708(M+Na) | 684(M–H) 798 (M+TFA) |
| 181 | 1-naphthyl | $C_{32}H_{31}F_4N_3O_7$ | 645.61 | 668(M+Na) | 644(M–H) 758 (M+TFA) |

EXAMPLE 182

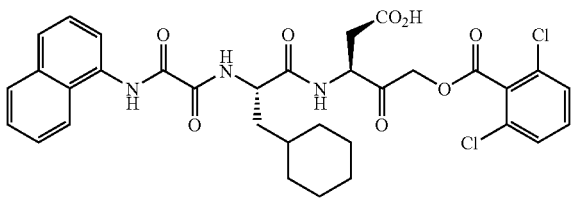

(3S)-3-[N-(N'-(5,6,7,8-Tetrahydro-1-Naphthyl)Oxamyl)-Cyclohexylalaninyl]Amino-5-(2',6'-Dichlorobenzoyloxy)-4-Oxopentanoic Acid Part A: Aspartic Acid, β-tert-Butyl, α-Methyl Ester p-Toluenesulfonate Salt To a solution of N-(benzyloxycarbonyl)-L-aspartic acid, β-tert-butyl ester (10.57 g, 32.7 mmol) in methanol(20 mL)-$CH_2Cl_2$(30 mL) at 0° C. (ice bath) was added portionwise a 2.0 M solution of (trimethylsilyl)diazomethane in hexanes (20 mL, 40 mmol). After stirring at 0° C. for 45 min, the excess reagent was quenched with formic acid (1.0 mL). The mixture was washed with saturated $NaHCO_3$ solution, dried over anhydrous $Na_2SO_4$ and evaporated to a pale yellow oil (11.34 g).

The crude product (11.34 g, ca 32.7 mmol) was taken up in methanol (100 mL), treated with p-toluenesulfonic acid mono hydrate (6.20 g, 32.6 mmol) and 10% Pd—C (0.5 g) and stirred under a hydrogen atmosphere (balloon) for 3 hrs. The mixture was filtered through Celite and concentrated to give the title compound as a white solid (12.68 g).

Part B: [(N-Benzyloxycarbonyl)Cyclohexylalaninyl]Aspartic Acid, β-tert-Butyl, α-Methyl Ester To a solution of (N-benzyloxycarbonyl)-cyclohexylalanine dicyclohexylamine salt (0.866 g, 1.77 mmol) in $CH_2Cl_2$ (10 mL) at 0° C. (ice bath) under nitrogen was added hydroxybenzotriazole hydrate (0.100 g) followed by 1-ethyl-3-(3',3'-dimethyl-1'-aminopropyl)carbodiimide hydrochloride (0.41 g, 2.14 mmol). After stirring at 0° C. for 10 min, the mixture was treated with aspartic acid, β-tert-butyl, α-methyl ester p-toluenesulfonate salt (0.665 g, 1.77 mmol) and N-methylmorpholine (0.2 mL, 1.8 mmol), and the reaction allowed to warm to room temperature. After stirring at room temperature for 2.5 hrs, the mixture was concentrated and the residue partitioned between EtOAc-water. The organic phase was washed with water, 5% $KHSO_4$, saturated $NaHCO_3$ and saturated NaCl solutions, dried over anhydrous $Na_2SO_4$ and evaporated to an oil. Purification by flash chromatography on silica gel eluting with EtOAc-hexane (1:3) gave the title compound (0.764 g, 88%) as a viscous oil. TLC(EtOAc-hexane; 1:2) Rf=0.46.

Part C: (3S)-3-[N-(N'-(5,6,7,8-Tetrahydro-1-Naphthyl)Oxamyl)-Cyclohexylalaninyl]Amino-5-(2',6'-Dichlorobenzoyloxy)-4-Oxopentanoic Acid Starting with [(N-benzyloxycarbonyl)cyclohexyl-alaninyl]aspartic acid, β-tert-butyl, α-methyl ester and following the general methods described in Example 4, Parts B through H, gave the title compound as a white solid. MS(ES) for $C_{33}H_{37}Cl_2N_3O_8$ (MW 674.58): positive 696/698(M+Na); negative 672/674(M–H), 786/788(M+TFA).

EXAMPLES 183–189

Starting with [(N-benzyloxycarbonyl)cyclohexyl-alaninyl]aspartic acid, β-tert-butyl, α-methyl ester (see Example 182, Part B), and following the general methods described in Example 4, Parts B through H, the compounds shown below in Table 9 were also prepared:

TABLE 9

| Ex. | R1 | B | Formula | MW | MS(ES) pos. | MS(ES) neg. |
|---|---|---|---|---|---|---|
| 183 | 5,6,7,8-tetrahydro-1-naphthyl | $CH_2O(2,3,5,6\text{-tetra-F-Ph})$ | $C_{32}H_{35}F_4N_3O_7$ | 649.64 | 672(M+Na) | 648(M–H) |
| 184 | 5,6,7,8-tetrahydro-1-naphthyl | $CH_2OPO(Me)Ph$ | $C_{33}H_{42}N_3O_8P$ | 639.68 | 662(M+Na) | 638(M–H); 752(M+TFA) |
| 185 | 5,6,7,8-tetrahydro-1-naphthyl | $CH_2OPOPh_2$ | $C_{38}H_{44}N_3O_8P$ | 701.75 | 724(M+Na); 740(M+K) | 700(M+H) |
| 186 | (2-PhCH$_2$)Ph | $CH_2OPO(Me)Ph$ | $C_{36}H_{42}N_3O_8P$ | 675.72 | 698(M+Na); 714(M+K) | 674(M–H); 788(M+TFA) |
| 187 | (2-PhCH$_2$)Ph | $CH_2OPOPh_2$ | $C_{41}H_{44}N_3O_8P$ | 737.79 | 760(M+Na); 776(M+K) | 736(M–H); 850(M+TFA) |
| 188 | (2-Ph)Ph | $CH_2OPO(Me)Ph$ | $C_{40}H_{42}N_3O_8P$ | 661.68 | 684(M+Na); 700(M+K) | 660(M–H); 774(M+TFA) |
| 189 | (2-Ph)Ph | $CH_2OPOPh_2$ | $C_{35}H_{40}N_3O_8P$ | 723.75 | 746(M+Na); 762(M+K) | 722(M–H); 836(M+TFA) |

EXAMPLE 190

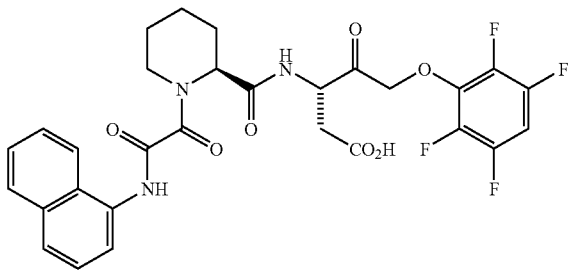

(3S)-3-[N-(N'-(1-Naphthyl)Oxamyl)Homoprolinyl]
Amino-5-(2',3',5',6'-Tetrafluorophenoxy)-4-Oxopentanoic Acid

Part A: [N-(1-Naphthyl)Oxamyl]Homoproline

To a solution of N-(1-naphthyl)oxamic acid (0.108 g, 0.50 mmol, see Example 1, Part A) in N-methylpyrrolidone(1.0 mL)-CH$_2$Cl$_2$(1.0 mL) at room temperature under nitrogen was added O-(7-azabenzotriazol-1-yl)-N,N,N',N'-tetramethyluronium hexafluorophate (0.209 g, 0.55 mmol). After stirring for 20 min, the mixture was treated with homoproline methyl ester (0.072 g, 0.50 mmol) and diisopropylethylamine (0.26 mL, 1.5 mmol). After stirring at room temperature for 4 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to give crude [N-(1-naphthyl)oxamyl]homoproline (0.156 g, 92%) as a colorless glass. TLC (EtOAc-hexane; 1:1) Rf=0.70.

To a solution of the crude methyl ester (0.156 g, ca 0.46 mmol) in dioxane(0.75 mL)-water(0.25 mL) was added 1.0 N LiOH solution (0.5 mL, 0.5 mmol). After stirring at room temperature for 1 hr. the mixture was acidified with 1.0 N HCl and extracted with EtOAc. The extract was washed with saturated NaCl solution, dried over anhydrous Na$_2$SO$_4$ and evaporated to give the title compound (0.105 g, 70%) as a white solid after trituration with Et$_2$O.

Part B: (3S,4RS)-3-[N-(N'-(1-Naphthyl)Oxamyl)
Homoprolinyl]Amino-5-(2',3',5',6'-Tetrafluorophenoxy)-4-Hydroxypentanoic Acid tert-Butyl Ester To a solution of [N-(1-naphthyl)oxamyl]homoproline (0.483 g, 1.48 mmol) in N-methylpyrrolidone(0.5 mL)-CH$_2$Cl$_2$(14 mL) at 0° C. under nitrogen was added O-(7-azabenzotriazol-1-yl)-N,N,N',N'-tetramethyluronium hexafluorophate (0.676 g, 1.78 mmol). After stirring for 20 min, the mixture was treated with a solution of (3S,4RS)-3-amino-5-(2',3',5',6'-tetraflurophenoxy)-4-hydroxypentanoic acid tert-butyl ester (0.540 g, 1.54 mmol, see Example 49, Part C) in CH$_2$Cl$_2$ (4.0 mL) followed by diisopropylethylamine (0.50 mL, 2.9 mmol). After stirring at 0° C. for 3 hrs and at room temperature for 16 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. Purification by flash chromatography on silica gel eluting with EtOAc-hexane (1:2) gave the title compound (0.268 g, 27%) as a tan foam. TLC (EtOAc-hexane; 1:1) Rf=0.39.

Part C: (3S)-3-[N-(N'-(1-Naphthyl)Oxamyl)Homoprolinyl]Amino-5-(2',3',5',6'-Tetrafluorophenoxy)-4-Oxoypentanoic Acid tert-Butyl Ester To a solution of (3S,4RS)-3-[N-(N'-(1-naphthyl)oxamyl) homoprolinyl]amino-5-(2',3',5',6'-tetrafluorophenoxy)-4-hydroxypentanoic acid tert-butyl ester (0.251 g, 0.38 mmol) in $CH_2Cl_2$ (4 mL) at room temperature under nitrogen was added Dess-Martin Periodinane (0.201 g, 0.475 mmol). After stirring at room temperature for 30 min, the mixture was diluted with EtOAc, washed with 1.0 M $Na_2S_2O_3$, saturated $NaHCO_3$ and saturated NaCl solutions, dried over anhydrous $Na_2SO_4$ and evaporated to a dryness. The residue was purified by flash chromatography on silica gel eluting with $CH_2Cl_2$-$Et_2O$-hexane (1:2:2) then EtOAc-hexane (1:2) to give the title compound (0.160 g, 64%) as a white foam. TLC(EtOAc-hexane; 1:1) Rf=0.57.

Part D: (3S,4RS)-3-[N-(N'-(1-Naphthyl)Oxamyl) Homoprolinyl]Amino-5-(2',3',5',6'-Tetrafluorophenoxy)-4-Oxoypentanoic Acid To a solution of (3S)-3-[N-(N'-(1-naphthyl)oxamyl)homoprolinyl]amino-5-(2', 3',5',6'-tetrafluorophenoxy)-4-oxopentanoic acid tert-butyl ester (0.152 g, 0.23 mmol) in $CH_2Cl_2$(1.0 mL)-anisole(0.4 mL) at room temperature under nitrogen was added trifluoroacetic acid (1.0 mL). The resulting clear solution was stirred at room temperature for 1 hr. evaporated to dryness and chased with toluene-$CH_2Cl_2$ (1:1). The residue was triturated with hexane to give the title compound (0.103 g, 74%) as an off-white solid. TLC (MeOH—$CH_2Cl_2$; 1:9) Rf=0.33. MS(ES) for $C_{29}H_{25}F_4N_3O_7$ (MW 603.53): positive 626(M+Na); negative 602(M–H).

EXAMPLE 191

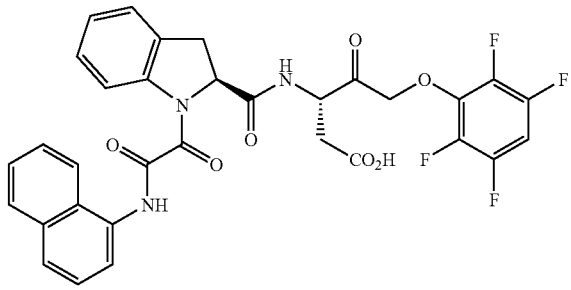

(3S)-3-[N-(1-Naphthyl)Oxamyl)Indoline-2-Carbonyl]Amino-5-(2',3',5',6'-Tetrafluorophenoxy)-4-Oxopentanoic Acid Part A:
[N-(1-Naphthyl)Oxamyl]Indoline-2-Carboxylic Acid Ethyl Ester To a solution of N-(1-naphthyl)oxamic acid (2.37 g, 11 mmol, see Example 1, Part A) in N-methylpyrrolidone(7.0 mL)-$CH_2Cl_2$(40 mL) at 0° C. (ice bath) under nitrogen was added 1,1'-carbonyldiimidazole (1.96 g, 12.1 mmol). After stirring at 0° C. for 1.5 hrs and at room temperature for 0.5 hrs, (S)-indoline-2-carboxylic acid ethyl ester hydrochloride (1.25 g, 5.5 mmol) and diisopropylethylamine (1.1 mL, 6.4 mmol) was added. After stirring at room temperature for 18 hrs, the mixture was diluted with EtOAc, washed successively with 5% $KHSO_4$, saturated $NaHCO_3$ and saturated NaCl solutions, dried over anhydrous $Na_2SO_4$ and evaporated to dryness. The crude product was purified by flash chromatography on silica gel eluting with $CH_2Cl_2$-$Et_2O$-hexane (1:1:3) to give the title compound (0.472 g, 22%) as a pale yellow oil. TLC($CH_2Cl_2$-$Et_2O$-hexane; 1:1:3) Rf=0.48.

Part B: (3S)-3-[N-(N'-(1-Naphthyl)Oxamyl)Indoline-2-Carbonyl]Amino-5-(2',3',5',6'-Tetrafluorophenoxy)-4-Oxopentanoic Acid Starting from [N-(1-naphthyl)oxamyl]indoline-2-carboxylic Acid ethyl ester, and following the methods described in Example 104, Parts A through D, the title compound was also prepared. MS(ES) for $C_{32}H_{23}F_4N_3O_7$ (MW 637.54): positive 660(M+Na),676(M+K); negative 636(M–H),672(M+Cl), 750(M+TFA).

EXAMPLE 192

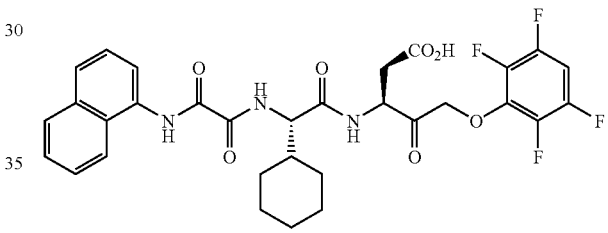

(3S)-3-[N-(N'-(1-Naphthyl)Oxamyl)Cyclohexylglycinyl]Amino-5-(2',3',5',6'-Tetrafluorophenoxy)-4-Oxopentanoic Acid Part A: (3S,4RS)-3-[(N-9-Fluorenylmethoxycarbonyl)Cyclohexylglycinyl]Amino-5-(2',3',5',6'-Tetrafluorophenoxy)-4-Hydroxypentanoic Acid tert-Butyl Ester To a solution of (N-9-fluorenylmethoxycarbonyl)cyclohexylglycine (0.514 g, 1.35 mmol) and (3S,4RS)-3-amino-5-(2',3',5',6'-tetrafluorophenoxy)-4-hydroxypentanoic acid tert-butyl ester (0.479 g, 1.36 mmol, see Example 92, Part C) in $CH_2Cl_2$(10 mL) at 0° C. (ice bath) under nitrogen was added O-(7-azabenzotriazol-1-yl)-N,N,N',N'-tetramethyluronium hexafluorophate (0.619 g, 1.62 mmol) and diisopropylethylamine (0.47 mL, 2.7 mmol). After stirring at 0° C. for 3 hrs, the reaction was allowed to warm to room temperature. After stirring at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography eluting with EtOAc-hexane (1:2) to give the title compound (0.481 g, 50%) as a white solid. TLC(EtOAc-hexane; 1:2) Rf=0.42.

Part B: (3S,4RS)-3-[Cyclohexylglycinyl]Amino-5-(2',3',5',6'-Tetrafluorophenoxy)-4-Hydroxypentanoic Acid tert-Butyl Ester A solution of (3S,4RS)-3-[(N-9-fluorenylmethoxycarbonyl)cyclohexylglycinyl]amino-5-(2',3',5',6'-tetrafluorophenoxy)-4-hydroxypentanoic acid tert-butyl ester (0.478 g, 0.67 mmol) in piperidine(0.1 mL)/dimethylformamide(2.0 mL) was stirred at room temperature under nitrogen for 1 hr. The mixture was diluted with EtOAc, washed with water and saturated NaCl solution, dried over anhydrous anhydrous $Na_2SO_4$ and evaporated to dryness. The residue was purified by flash chromatography eluting with EtOAc-hexane (1:2) to give the title compound (0.121 g, 45%) as a white solid. TLC(MeOH—$CH_2Cl_2$; 5:95) Rf=0.38.

Part C: (3S,4RS)-3-[N-(N'-(1-Naphthyl)Oxamyl) Cyclohexylglycinyl]Amino-5-(2',3',5',6'-Tetrafluorophenoxy)-4-Hydroxypentanoic Acid tert-Butyl Ester To a solution of N-(1-naphthyl)oxamic acid (0.088 g, 0.41 mmol, see Example 1, Part A) and (3S,4RS)-3-(cyclohexylglycinyl)amino-5-(2',3',5',6'-tetrafluorophenoxy)-4-hydroxypentanoic acid tert-butyl ester (0.110 g, 0.27 mmol) in N-methylpyrrolidone(0.5 mL)-$CH_2Cl_2$(3.0 mL) at 0° C. under nitrogen was added O-(7-azabenzotriazol-1-yl)-N,N,N',N'-tetramethyluronium hexafluorophate (0.125 g, 0.32 mmol) and diisopropylethylamine (90 μL, 0.54 mmol). After stirring at 0° C. for 3 hrs and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with EtOAc-hexane (1:2) to give the title compound (0.094 g, 50%) as a white foam. TLC(EtOAc-hexane; 1:1) Rf=0.50.

Part D: (3S)-3-[N-(N'-(1-Naphthyl)Oxamyl)Cyclohexylglycinyl]Amino-5-(2',3',5',6'-Tetrafluorophenoxy)-4-Oxoypentanoic Acid tert-Butyl Ester To a solution of (3S,4RS)-3-[N-(N'-(1-naphthyl)oxamyl)cyclohexylglycinyl]amino-5-(2',3',5',6'-tetrafluorophenoxy)-4-hydroxypentanoic acid tert-butyl ester (0.082 g, 0.12 mmol) in $CH_2Cl_2$(1 mL)-$CH_3CN$(2 mL)-DMSO(0.2 mL) at room temperature under nitrogen was added Dess-Martin Periodinane (0.145 g, 0.34 mmol). After stirring at room temperature for 1 hr, the mixture was diluted with EtOAc, washed with 1.0 M $Na_2S_2O_3$, saturated $NaHCO_3$ and saturated NaCl solutions, dried over anhydrous $Na_2SO_4$ and evaporated to a dryness. The residue was purified by flash chromatography on silica gel eluting with EtOAc-hexane (1:2 then 1:1) to give the title compound (0.068 g, 83%) as a tan foam. TLC(EtOAc-hexane; 1:1) Rf=0.63.

Part E: (3 S,4RS)-3-[N-(N'-(1-Naphthyl)Oxamyl) Cyclohexylglycinyl]Amino-5-(2',3',5',6'-Tetrafluorophenoxy)-4-Oxoypentanoic Acid To a solution of (3S)-3-[N-(N'-(1-naphthyl)oxamyl)cyclohexylglycinyl]amino-5-(2',3',5',6'-tetrafluorophenoxy)-4-oxopentanoic acid tert-butyl ester (0.065 g, 0.23 mmol) in $CH_2Cl_2$(1.0 mL)-anisole(0.2 mL) at room temperature under nitrogen was added trifluoroacetic acid (1.0 mL). The resulting clear solution was stirred at room temperature for 30 min, evaporated to dryness and chased with toluene-$CH_2Cl_2$ (1:1). The residue was triturated with $Et_2O$ to give the title compound (0.034 g, 56%) as an off-white solid. TLC (MeOH—AcOH—$CH_2Cl_2$; 1:1:32) Rf=0.45. MS(ES) for $C_{31}H_{29}F_4N_3O_7$ (MW 631.58): positive 654(M+Na); negative 630(M−H).

EXAMPLES 193–200

Starting from (3S,4RS)-3-amino-5-(2',3',5',6'-tetrafluorophenoxy)-4-hydroxy-pentanoic acid tert-butyl ester (see Example 178, Part C) and following the general methods described in Example 192, Parts A through E, the compounds shown below in Table 10 were also prepared:

TABLE 10

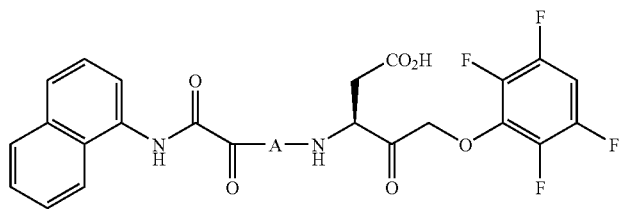

| Ex. | A | Formula | MW | MS(ES) pos. | MS(ES) neg. |
|---|---|---|---|---|---|
| 193 | norleucine | $C_{29}H_{27}F_4N_3O_7$ | 605.54 | 628(M+Na) 644(M+K) | 604(M−H) 640(M+Cl) 718(M+TFA) |
| 194 | (t-butyl)glycine | $C_{29}H_{27}F_4N_3O_7$ | 605.54 | 606(M+H) 628(M+Na) 644(M+K) | 604(M−H) 640(M+Cl) 718(M+TFA) |
| 195 | (t-butyl)alanine | $C_{20}H_{29}F_4N_3O_7$ | 619.57 | 620(M+H) 642(M+Na) 658(M+K) | 618(M−H) 732(M+TFA) |
| 196 | phenylglycine | $C_{31}H_{23}F_4N_3O_7$ | 625.53 | 626(M+H) 648(M+Na) 664(M+K) | 624(M−H) 660(M+Cl) 738(M+TFA) |

TABLE 10-continued

| Ex. | A | Formula | MW | MS(ES) pos. | MS(ES) neg. |
|---|---|---|---|---|---|
| 197 | phenylalanine | $C_{32}H_{25}F_4N_3O_7$ | 639.56 | 640(M+H) 662(M+Na) 678(M+K) | 638(M−H) 674(M+Cl) 712(M+TFA) |
| 198 | homophenylalanine | $C_{33}H_{27}F_4N_3O_7$ | 653.59 | 654(M+H) 676(M+Na) 692(M+K) | 652(M−H) 688(M+Cl) 766(M+TFA) |
| 199 | 1-aminocyclopentane carboxylic acid | $C_{29}H_{25}F_4N_3O_7$ | 603.53 | 626(M+Na) 642(M+K) | 602(M−H) |
| 200 | histidine | $C_{29}H_{23}F_4N_5O_7$ | 629.15 | 630(M+H) | 28(M−H) |

EXAMPLE 201

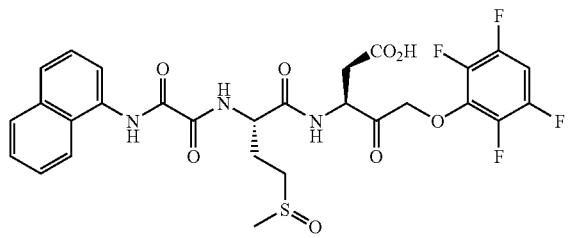

(3S)-3-[N-(1-Naphthyl)Oxamyl)Methioninyl(Sulfoxide)]Amino-5-(2',3',5',6'-Tetrafluorophenoxy)-4-Oxopentanoic Acid Part A: (3S,4RS)-3-[N-(N'-(1-Naphthyl)Oxamyl) Methioninyl]Amino-5-(2',3',5',6'-Tetrafluorophenoxy)-4-Hydroxypentanoic Acid tert-Butyl Ester Starting from (N-9-fluorenylmethoxycarbonyl)methionine and following the methods described in Example 106, Parts A through C, the title compound was also prepared. TLC(EtOAc-hexane; 1:2) Rf=0.39.

Part B: (3S)-3-[N-(N'-(1-Naphthyl)Oxamyl)Methioninyl(Sulfoxide)]Amino-5-(2',3',5',6'-Tetrafluorophenoxy)-4-Oxoypentanoic Acid tert-Butyl Ester To a solution of (3S,4RS)-3-[N-(N'-(1-naphthyl)oxamyl)methioninyl]amino-5-(2',3',5',6'-tetrafluorophenoxy)-4-hydroxypentanoic acid tert-butyl ester (0.251 g, 0.37 mmol) in $CH_2Cl_2$(4.0 mL) at room temperature under nitrogen was added Dess-Martin Periodinane (0.203 g, 0.48 mmol). After stirring at room temperature for 1 hr, the mixture was diluted with EtOAc, washed with 1.0 M $Na_2S_2O_3$, saturated $NaHCO_3$ and saturated NaCl solutions, dried over anhydrous $Na_2SO_4$ and evaporated to a dryness. The residue was purified by flash chromatography on silica gel eluting with EtOAc-hexane (1:2 then 1:1) followed by MeOH—$CH_2Cl_2$ (5:95 then 1:9) to give a mixture of two isomeric sulfoxides (0.225 g); TLC(MeOH—$CH_2Cl_2$; 1:9) Rfs 0.48 and 0.43. The mixture was re-chromatographed on silica gel eluting with isopropanol-$CH_2Cl_2$ (2.5% to 5% to 10%) to give sulfoxide isomer A (less polar, 0.051 g), sulfoxide isomer B (more polar, 0.086 g) and a mixture of isomers A and B (0.040 g). Both isomers have virtually identical mass spectra. MS(ES) for $C_{32}H_{33}F_4N_3O_8S$ (MW 695.68): positive 718(M+Na); negative 694(M−H).

Part C: (3S,4RS)-3-[N-(N'-(1-Naphthyl)Oxamyl) Methioninyl(Sulfoxide)]Amino-5-(2',3',5',6'-Tetrafluorophenoxy)-4-Oxoypentanoic Acid To a solution of (3S)-3-[N-(N'-(1-naphthyl)oxamyl)methioninyl(sulfoxide)]amino-5-(2',3',5',6'-tetrafluorophenoxy)-4-oxopentanoic acid tert-butyl ester (isomer A, 0.046 g, 0.07 mmol) in $CH_2Cl_2$(2.0 mL)-anisole(0.1 mL) at room temperature under nitrogen was added trifluoroacetic acid (1.0 mL). The resulting clear solution was stirred at room temperature for 30 min, evaporated to dryness and chased with toluene-$CH_2Cl_2$ (1:1). The residue was triturated with $Et_2O$-hexane to give the title compound, isomer A (0.034 g, 81%) as an off-white solid. TLC(MeOH-AcOH—$CH_2Cl_2$; 1:1:32) Rf=0.20. MS(ES) for $C_{28}H_{25}F_4N_3O_8S$ (MW 639.57): positive 640(M+H), 662(M+Na), 678(M+K); negative 638(M−H), 752(M+TFA). Under the same conditions sulfoxide isomer B (0.081 g, 0.12 mmol) gave the title compound, isomer B (0.055 g, 74%). MS(ES) for $C_{28}H_{25}F_4N_3O_8S$ (MW 639.57): positive 640(M+H), 662 (M+Na), 678(M+K); negative 638(M−H), 674(M+Cl), 752 (M+TFA).

EXAMPLE 202

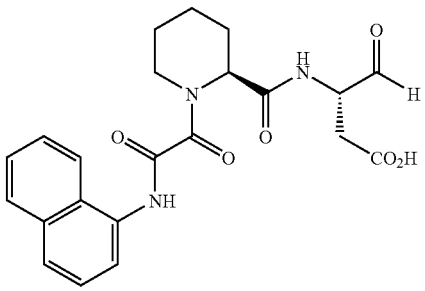

(3S)-3-[N-(N'-(1-Naphthyl)Oxamyl)Homoprolinyl]
Amino-4-Oxobutanoic Acid

Part A: (3S)-3-[N-(N'-(1-Naphthyl)Oxamyl)Homoprolinyl]Amino-4-Oxobutanoic Acid (tert)-Butyl Ester Semicarbazone To a solution of [N-(1-naphthyl)oxamyl]homoproline (0.103 g, 0.32 mmol, see Example 104, Part A) in $CH_2Cl_2$ (3.0 mL) at 0° C. under nitrogen was added hydroxybenzotriazole hydrate (0.058 g) followed by 1-ethyl-3-(3',3'-dimethyl-1'-aminopropyl)carbodiimide hydrochloride (0.91 g, 0.47 mmol). After stirring at 0° C. for 10 min, the mixture was treated with (3S)-amino-4-oxobutanoic acid (tert)-butyl ester semicarbazone, p-toluenesulfonate salt (0.127 g, 0.32 mmol) and N-methylmorpholine (42 µL, 0.38 mmol). After stirring at 0° C. for 2 hrs, the mixture was concentrated and the residue partitioned between EtOAc-5% $KHSO_4$. The organic phase was washed with 5% $KHSO_4$, saturated $NaHCO_3$ and saturated NaCl solutions, dried over anhydrous $Na_2SO_4$ and evaporated to give the crude title compound (0.119 g, 70%) as a colorless glass.

Part B: (3S)-3-[N-(N'-(1-Naphthyl)Oxamyl)Homoprolinyl]Amino-4-Oxobutanoic Acid Semicarbazone To a solution of (3S)-3-[N-(N'-(1-naphthyl)oxamyl)homoprolinyl]amino-4-oxobutanoic acid semicarbazone tert-butyl ester (0.119 g, 0.21 mmol) in $CH_2Cl_2$(2.0 mL)-anisole (0.05 mL)-water(0.05 mL) at room temperature under nitrogen was added trifluoroacetic acid (0.32 mL). The resulting clear solution was stirred at room temperature for 18 hrs, evaporated to dryness and chased with toluene-$CH_2Cl_2$ (1:1). The residue was triturated with Et2O to give the title compound (0.079 g, 74%) as a white solid.

Part C: (3S)-3-[N-(N'-(1-Naphthyl)Oxamyl)Homoprolinyl]Amino-4-Oxobutanoic Acid

A suspension of (3S)-3-[N-(N'-(1-naphthyl)oxamyl)homoprolinyl]amino-4-oxobutanoic acid semicarbazone (0.079 g, 0.16 mmol) in 37% aqueous formaldehyde(0.6 mL)-acetic acid(0.6 mL)-methanol(1.8 mL) was stirred at room temperature under nitrogen for 18 hrs. The resulting clear solution was diluted with water and mixture concentrated on a rotovap. The aqueous solution was then frozen and lyophilized. The residue was taken up in methanol, filtered through Celite and filtrate evaporated to dryness. Trituration of the residue with $Et_2O$ gave the title compound (0.037 g, 53%) as a white solid. MS(ES) for $C_{22}H_{23}N_3O_6$ (MW 425.44): positive 448(M+Na); negative 424(M−H).

EXAMPLE 203

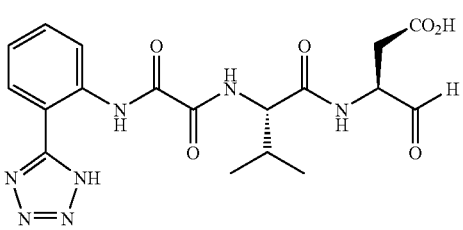

(3S)-3-[N-(N'-(2-(1H-Tetrazol-5-yl)Phenyl)Oxamyl)Valinyl]Amino-4-Oxobutanoic Acid Part A: 2-(1'-Phenylmethyl-5'-Tetrazolyl)Aniline Hydrochloride A solution of 2-cyano-acetanilide (0.801 g, 5.0 mmol) and tri-n-butyltin azide (2.05 mL, 7.5 mmol) in anhydrous toluene (10 mL) was heated at reflux for 48 hrs. The mixture was allowed to cool to room temperature and treated with 2.0 N HCl in $Et_2O$ (5.0 mL). The resulting precipate was collected by suction, washed with hexane and dried in vacuo to give 2-(1H-tetrazol-5-yl)acetanilide (0.917 g, 90%) as a white solid.

To a suspension of 2-(1H-tetrazol-5-yl)acetanilide (0.203 g, 1.0 mmol) in tetrahydrofuran (2.0 mL) at 0° C. under nitrogen was added triethylamine (0.170 mL, 1.2 mmol) and benzyl bromide (0.125 mL, 1.05 mmol). After stirring at 0° C. for 3 hrs and at room temperature for 16 hrs, the mixture was partitioned between EtOAc-water. The organic phase was washed with saturated $NaHCO_3$ and saturated NaCl solutions, dried over anhydrous $Na_2SO_4$ and evaporated to a dryness. The residue was triturated with hexane to give 2-(1'-phenylmethyl-5'-tetrazolyl)acetanilide (0.218 g, 74%) as a white solid. $^1$H-NMR indicates that the product is a single regioisomer. Assignment of regiochemistry should be considered tentative. $^1$H-NM($CDCl_3$): δ 2.22 ppm (3H,s), 5.84 (2H,s), 7.16 (1H, dt, J=7.8, 1.5 Hz), 7.40 (6H, m), 8.19 (1H, dd, J=7.8, 1.5 Hz), 8.63 (1H, d, J=8.4 Hz). 10.58 (1H, bs).

A mixture of 2-(1'-phenylmethyl-5'-tetrazolyl)acetanilide (0.216 g, 0.74 mmol) and 10% aqueous HCl (3.0 mL) was refluxed for 18 hrs. The mixture was evaporated to dryness and the residue triturated with $Et_2O$ to give the title compound (0.187 g, 88%) as a white solid.

Part B: N-[2-(1'-Phenylmethyl-5'-Tetrazolyl)Phenyl] Oxamic Acid

To a solution of 2-(1'-phenylmethyl-5'-tetrazolyl)aniline hydrochloride (0.177 g, 0.615 mmol), 4-dimethylaminopyridine (0.008 g, 0.065 mmol) and triethylamine (0.19 mL, 1.4 mmol) in $CH_2Cl_2$ (1.0 mL) at 0° C. (ice bath) under nitrogen was added methyl oxalyl chloride (62 µL, 0.67 mmol). After stirring at 0° C. for 2 hrs, the mixture was allowed to come to room temperature, stirred for 18 hrs and then partitioned between EtOAc-5% $KHSO_4$. The organic phase was washed with saturated NaCl solution, dried over anhydrous $Na_2SO_4$ and evaporated to dryness.

The crude methyl ester (0.207 g, ca 0.615 mmol) was taken up in dioxane (2.0 mL) and treated with 1.0 N LiOH solution (0.68 mL, 0.68 mmol) and stirred at room temperature for 1 hr. The mixture was acidified with 1.0 N HCl and extracted with EtOAc. The extract was washed with saturated NaCl solution, dried over anhydrous $Na_2SO_4$ and evaporated to dryness. Trituration of the crude product with hexane gave the title compound (0.121 g, 61%) as a white solid.

Part C: (3S)-3-[N-(N'-(2-(1'-Phenylmethyl-5'-Tetrazolyl)Phenyl)Oxamyl)Valinyl]Amino-4-Oxobutanoic Acid Semicarbazone tert-Butyl Ester To a solution of N-[2-(1'-phenylmethyl-5'-tetrazolyl)phenyl]oxamic acid (0.065 g, 0.20 mmol) in $CH_2Cl_2$(2.0 mL) at 0° C. under nitrogen was added hydroxybenzotriazole hydrate (0.037 g) followed by 1-ethyl-3-(3',3'-dimethyl-1'-aminopropyl)-carbodiimide hydrochloride (0.058 g, 0.30 mmol). After stirring at 0° C. for 10 min, the mixture was treated with (3S)-3-(valinyl)amino-4-oxobutanoic acid (tert)-butyl ester semicarbazone (0.066 g, 0.20 mmol, prepared by the method described for the corresponding leucine analogue in Example 1, Parts B and C) and N-methylmorpholine (26 μL, 0.24 mmol). After stirring at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to give the crude title compound (0.090 g, 62%) as a colorless glass.

Part D: (3S)-3-[N-(N'-(2-(1'H-5'-Tetrazolyl)Phenyl)Oxamyl)Valinyl]Amino-4-Oxobutanoic Acid Semicarbazone tert-Butyl Ester To a solution of crude (3S)-3-[N-(N'-(2-(1'-phenylmethyl-5'-tetrazolyl)phenyl)oxamyl)valinyl]amino-4-oxobutanoic acid semicarbazone tert-butyl ester (0.089 g, ca. 0.14 mmol) in MeOH (1.0 mL) was added 10% Pd—C (0.009 g) and resulting mixture stirred under a hydrogen atmosphere (balloon) for 48 hrs. The mixture was filtered through Celite washing the filter cake with $CH_2Cl_2$ and the combined filtrates evaporated to dryness. The residue was triturated with $Et_2O$ to give the title product (0.060 g, 79%) as a white solid.

Part E: (3S)-3-[N-(N'-(2-(1'H-5'-Tetrazolyl)Phenyl)Oxamyl)Valinyl]Amino-4-Oxobutanoic Acid Semicarbazone To a solution of (3S)-3-[N-(N'-(2-(1'H-5'-tetrazolyl)phenyl)oxamyl)valinyl]amino-4-oxobutanoic acid tert-butyl ester (0.058, 0.11 mmol) in $CH_2Cl_2$(1.0 mL)-anisole(0.05 mL) at room temperature under nitrogen was added 6.0 M HCl/AcOH (1.0 mL). The resulting solution was stirred at room temperature for 18 hrs, evaporated to dryness and chased with toluene-$CH_2Cl_2$ (1:1). The residue was triturated with $Et_2O$ to give the title compound (0.048 g, 92%) as a white solid.

Part F: (3S)-3-[N-(N'-(2-(1'H-5'-Tetrazolyl)Phenyl)Oxamyl)Valinyl]Amino-4-Oxobutanoic Acid A solution of (3S)-3-[N-(N'-(2-(1'H-5'-tetrazolyl)phenyl)oxamyl)valinyl]amino-4-oxobutanoic acid semicarbazone (0.048 g, 0.10 mmol) in 37% aqueous formaldehyde(0.4 mL)-acetic acid(0.4 mL)-methanol(1.2 mL) was stirred at room temperature under nitrogen for 18 hrs. The resulting clear solution was diluted with water and mixture concentrated on a rototvap. The aqueous solution was then frozen and lyophilized. The residue was taken up in methanol, filtered through Celite and filtrate evaporated to dryness. Trituration of the residue with $Et_2O$ gave the title compound (0.025 g, 59%) as a white solid. MS(ES) for $C_{18}H_{21}N_7O_6$ (MW 431.41): positive 454(M+Na); negative 430(M-H).

EXAMPLE 204

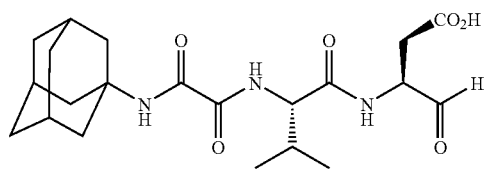

(3S)-3-[N—(N 1-Adamantanyl)Oxamyl)Valinyl]
Amino-4-Oxobutanoic Acid

Part A: (3S)-3-[N-(9-Fluorenylmethoxycabonyl)Valinyl]Amino-4-Oxobutanoic Acid (tert-Butyl) Ester Semicarbazonyl-4-[2'-(4-Ethyl-Phenoxyacetyl)]Aminomethylpolystrene Aminomethylpolystryene resin (10.0 g, 100–200 mesh, 0.71 meq/g) was placed in a 200 mL filter tube equipped with a vacuum stopcock and glass frit and washed successively with $CH_2Cl_2$(50 mL)/dimethylformamide(50 mL), diisopropylethylamine(5 mL)/dimethylformamide(30 mL), dimethylformamide (2×50 mL) and tetrahydrofuran (30 mL). The resin was suspended in tetrahydrofuran(20 mL)/N-methylpyrolidinone(20 mL) with nitrogen agitation through the bottom of the frit and treated with diisopropylethylamine (1.9 mL, 10.9 mmol) and (3S)-3-(9-fluorenylmethoxycabonyl)amino-4-oxobutanoic acid (tert-butyl)ester semicarbazonyl-4-[2'-(4-ethyl-phenoxyacetic acid)] (2.24 g, 3.56 mmol). After all of the solid had dissolved (approx. 10 min), the mixture was treated with pyBOP [benzotriazolyloxy-tris(N-pyrolidinyl)phosphonium hexafluorophosphate, 2.78 g, 5.34 mmol) in one portion. After mixing by nitrogen agitation for 3 hrs, the supernatant was removed by suction and the resin washed successively with tetrahydrofuran (2×50 mL), dimethylformamide (3×50 mL) and $CH_2Cl_2$ (2×50 mL). Unreacted amine groups were capped by treatment with a mixture of acetic anhydride(10 mL)/dimethylformamide(30 mL)/diisopropylethylamine(1.0 mL). After mixing by nitrogen agitation for 1 hr, the supernatant was removed by suction and the resin washed with dimethylformamide(4×50 mL).

The resin was treated with piperidine(10 mL)/dimethylformamide(40 mL) and mixed by nitrogen agitation for 1 hr. The supernatant was removed by suction and the resin washed with dimethylformamide (4×50 mL) and tetrahydrofuran (50 mL).

The resin was suspended in tetrahydrofuran(20 mL)/N-methylpyrolidinone(20 mL), treated with N-(9-fluorenylmethoxycabonyl)valine (3.63 g, 10.7 mmol), diisopropylethylamine (5.7 mL, 32.7 mmol) and pyBOP (8.34 g, 16.0 mmol) and mixed by nitrogen agitation for 2.5 hrs. The supernatant was removed by suction and the resin washed successively with dimethylformamide (3×40 mL) and $CH_2Cl_2$ (3×40 mL), methanol (2×40 mL) and $Et_2O$ (2×40 mL). The resin was dried in vacuo to give the title product (12.69 g, quantitative). Based on the starting semicarbazone-acid, the resin loading was calculated as approximately 0.28 meq/g.

Part B: (3S)-3-[N-(N'-(1-Adamantanyl)Oxamyl)Valinyl]Amino-4-Oxobutanoic Acid

An aliquot of the Part A resin (0.125 g, ca 0.035 mmol) was placed in a 6 mL Supelco™ filtration tube equipped with a 20 μm polyethylene frit, treated with piperidine-dimethylformamide (1.0 mL, 1:4 v/v) and mixed on an orbital shaker for 1 hr. The supernatant was removed by suction and the resin washed with dimethylformamide (4×1.0 mL) and $CH_2Cl_2$ (3×1.0 mL). The resin was treated with 0.5M $iPr_2NEt$ in N-methylpyrolidinone (0.40 mL, 0.20 mmol), (1-adamantanyl)oxamic acid (0.0246 g, 0.11 mmol) and 0.25M O-(7-azabenzotriazol-1-yl)-N,N,N',N'-tetramethyluronium hexafluorophate in N-methylpyrolidinone (0.40 mL, 0.10 mmol). The mixture was mixed on an orbital shaker under an nitrogen atmosphere for 16 hrs. The supernatant was removed by suction and the resin washed successively with dimethylformamide (3×1.0 mL) and $CH_2Cl_2$ (3×1.0 mL), methanol (2×1.0 mL) and $Et_2O$ (2×1.0 mL).

The resin was treated with 1.0 mL of $CH_2Cl_2$ and allowed to re-swell for 15 min. The solvent was removed by suction and the resin treated with trifluoroacetic acid-$CH_2Cl_2$-anisole (1.0 mL, 4:3:1 v/v/v). After mixing on an orbital shaker under nitrogen for 5.5 hrs, the supernatant was removed by suction and the resin washed with $CH_2Cl_2$ (4×1.0 mL). The resin was treated with 37% aqueous formaldehyde-acetic acid-tetrahydrofuran-trifluoroacetic acid (1.0 mL, 1:1:5:0.025 v/v/v/v) and mixed on an orbital shaker under nitrogen for 4.5 hrs. The supernatant was collected by suction, the resin washed with tetrahydrofuran (3×0.5 mL). The combined filtrates were blown down under nitrogen. The residue was taken up in methanol (0.5 mL), filtered and applied directly to a 3 mL Supelco™ LC-18 reverse phase extraction tube which had been pre-conditioned with water, and eluted successively with 3 mL each of 10% MeOH-water, 30% MeOH-water, 60% MeOH-water and 90% MeOH-water. The product-containing fractions (TLC) were combined and evaporated to dryness to give the title compound (0.0114 g, 77%) as a colorless glass. TLC(AcOH-MeOH—$CH_2Cl_2$; 1:1:20) Rf=0.23. MS(ES) for $C_{21}H_{31}N_3O_6$ (MW 421.49): positive 444(M+Na), 460(M+K); negative 420(M−H), 534(M+TFA).

EXAMPLES 205–219

Starting with (3S)-3-[N-(9-fluorenylmethoxycabonyl)valinyl]amino-4-oxobutanoic acid (tert-butyl)ester semicarbazonyl-4-[2'-(4-ethyl-phenoxyacetyl)]aminomethylpolystrene (see Example 204, Part A) and following the methods described in Example 204, Part B, the compounds shown below in Table 11 were also prepared:

TABLE 11

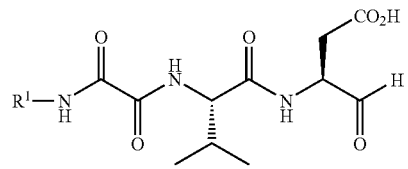

| Ex. | $R^1$ | Formula | MW | MS(ES) pos. | MS(ES) neg. |
|---|---|---|---|---|---|
| 205 | Ph | $C_{17}H_{21}N_3O_6$ | 363.37 | 386(M+Na) 402(M+K) | 362(M−H) |
| 206 | $PhCH_2$ | $C_{18}H_{23}N_3O_6$ | 377.40 | 400(M+Na) | 376(M−H) |
| 207 | $Ph(CH_2)_2$ | $C_{19}H_{25}N_3O_6$ | 391.42 | 414(M+Na) 430(M+K) | 390(M−H) 504(M+TFA) |
| 208 | $(2\text{-}CF_3)Ph$ | $C_{18}H_{20}F_3N_3O_6$ | 431.37 | 454(M+Na) | 430(M−H) |
| 209 | (2-t-Bu)Ph | $C_{21}H_{29}N_3O_6$ | 419.48 | 442(M+Na) 458(M+K) | 418(M−H) 532(M+TFA) |
| 210 | (2-Ph)Ph | $C_{23}H_{25}N_3O_6$ | 439.47 | 462(M+Na) 478(M+K) | 438(M−H) 552(M+TFA) |
| 211 | $(2\text{-}PhCH_2)Ph$ | $C_{24}H_{27}N_3O_6$ | 453.49 | 476(M+Na) 492(M+K) | 452(M−H) 566(M+TFA) |
| 212 | (2-PhO)Ph | $C_{23}H_{25}N_3O_7$ | 455.47 | 478(M+Na) 494(M+K) | 454(M−H) 568(M+TFA) |
| 213 | 2-naphthyl | $C_{21}H_{23}N_3O_6$ | 413.43 | 436(M+Na) 452(M+K) | 412(M−H) 526(M+TFA) |
| 214 | 1-naphthyl | $C_{21}H_{23}N_3O_6$ | 413.43 | 436(M+Na) 452(M+K) | 412(M−H) 526(M+TFA) |
| 215 | 4-Cl-1-naphthyl | $C_{21}H_{22}ClN_3O_6$ | 447.87 | 470/472(M+Na) 486/488(M+K) | 446/448(M−H) |
| 216 | 5,6,7,8-tetrahydro-1-naphthyl | $C_{21}H_{27}N_3O_6$ | 417.46 | 440(M+Na) 456(M+K) | 416(M−H) 530(M+TFA) |
| 217 | 1,2,3,4-tetrahydro-1-naphthyl | $C_{21}H_{27}N_3O_6$ | 417.46 | 440(M+Na) 456(M+K) | 416(M−H) 530(M+TFA) |
| 218 | $(1\text{-naphthyl})CH_2$ | $C_{22}H_{25}N_3O_6$ | 427.46 | 450(M+Na) 466(M+K) | 426(M−H) 540(M+TFA) |
| 219 | 2-benzimidazoyl | $C_{18}H_{21}N_5O_6$ | 403.39 | — | — |

EXAMPLE 220

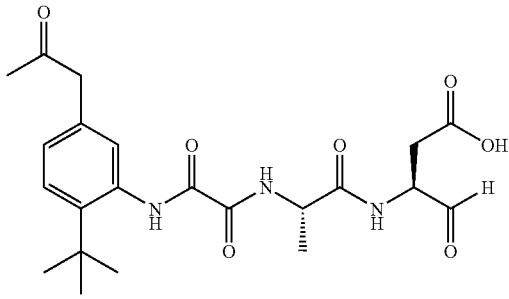

N-(5-ACETYLAMINO-2-TERT-BUTYL-PHENYL)-N'-[1-(2-HYDROXY-5-OXO-TETRAHYDRO-FURAN-3-YLCARBAMOYL)-ETHYL]-OXALAMIDE

Part A: 2-tert-Butyl-5-nitro-phenylamine

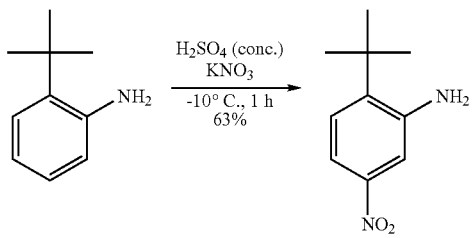

To H$_2$SO$_4$ (50.0 g, 509.79 mmol) was slowly added 2-tert-Butylaniline (5.0 g, 33.50 mmol). The mixture was stirred at room temperature until it became Homogeneous, then was cooled to −10° C. before slow addition of KNO$_3$ in small portions (5.00 g, 49.45 mmol) via a powder addition funnel. After stirring at −10° C. for an hour, the reaction mixture was poured over a small portion of ice in a 250 mL beaker, allowed to stand for 10 min, then filtered and discarded white precipitate. The aqueous solution was neutralized with NH$_4$OH until pH 8–9 (Litmus pH paper) and partitioned between EtOAc/water. The organic phase was washed with water, and saturated NaCl solutions, dried over anhydrous Na$_2$SO$_4$ and evaporated to a dryness (brown oil). The brown residue was recrystallized from methanol/water to give the desired compound (4.1 g, 63%) as dark brown crystals. TLC (20% EtOAc/Hexane) R$_f$=0.66; $^1$HNMR (CDCl$_3$) δ 7.55 (dd, J=8.4, 2.4 Hz, 1H), 7.46 (d, J=2.7 Hz, 1H), 7.35–7.33 (d, J=8.7 Hz), 4.16 (br.s, 2H), 1.44 (s, 9H).

Part B: N-(2-tert-Butyl-5-nitro-phenyl)-oxalamic acid methyl ester

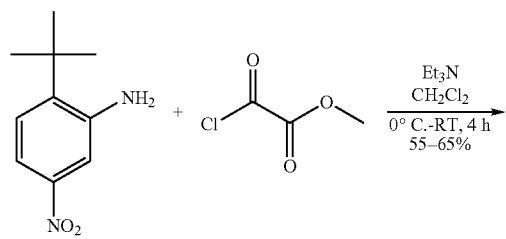

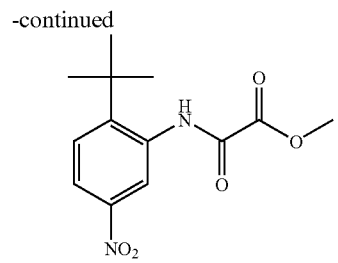

To a suspension of 2-tert-Butyl-5-nitro-phenylamine (4.04 g, 20.80 mmol) in CH$_2$Cl$_2$ (20 mL) at 0° C. was added 1.1 equiv of Methyl chlorooxoacetate (2.10 mL, 22.88 mmol) and followed by dropwise addition of 1.1 equiv of Et$_3$N (3.19 mL, 22.88 mmol). After stirring at 0° C. and allowing to warm up to room temperature over 4 hrs, the reaction mixture was treated with water (20 mL), stirred for 10 min and then partitioned between EtOAc/water. The organic phase was washed with 0.5N HCl (2×25 mL), and saturated NaCl solution (50 mL), dried over Na$_2$SO$_4$ and evaporated to dryness. The residue was purified by flask column chromatography on silica gel eluting with EtOAc/Hexane (5–25%) to give the title compound (3.25 g, 56%) as light yellow crystals. TLC (30% EtOAc/Hexane) R$_f$=0.39; $^1$HNMR (CDCl$_3$) δ 9.36 (br.s, 1H), 8.97 (d, J=2.4 Hz, 1H), 8.02 (dd, J=9.0, 2.4 Hz, 1H), 7.60 (d, J=9.0 Hz, 1H), 4.03 (s, 3H), 1.52 (s, 9H).

Part C: N-(5-Amino-2-tert-butyl-phenyl)-oxalamic acid methyl ester

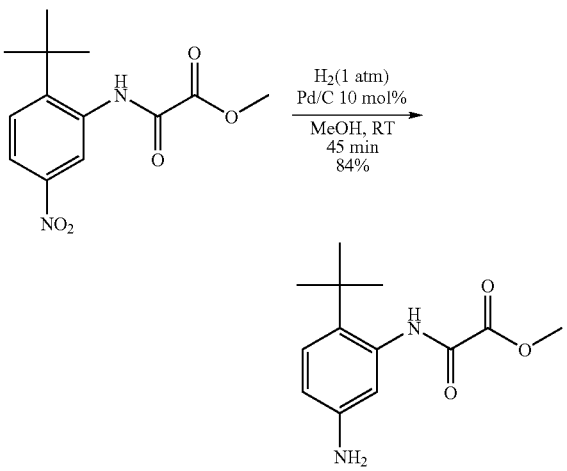

To a suspension of N2-tert-Butyl-5-nitro-phenyl)-oxalamic acid methyl ester (1.50 g, 5.32 mmol) in MeOH (100 mL) was added Pd/C 10 mol % (0.10 g). The reaction flask was purged with H$_2$ (1atm)/vacuum three times, then stirred under H$_2$ (1atm) at room temperature. After stirring for 45 min, the reaction was filtered through celite and evaporated to dryness. The residue was triturated with hexane to give the title compound (1.12 g, 84%) as a gray solid. TLC (40% EtOAc/Hexane) R$_f$=0.21; $^1$HNMR(CDCl$_3$) δ 9.21 (br.s, 1H), 7.47 (d, J=2.4 Hz, 1H), 7.18 (d, J=8.7 Hz, 1H), 6.50 (dd, J=8.4, 2.7 Hz, 1H), 4.00 (s, 3H), 1.42 (s, 9H); MS(ES) for C13H18N2O5 (MW=250.29) positive 251 (MH+).

Part D: N-(5-Acetylamino-2-tert-butyl-phenyl)-oxalamic acid methyl ester

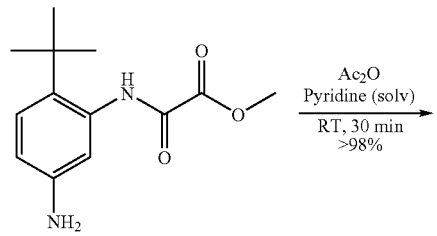

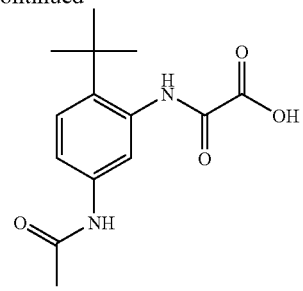

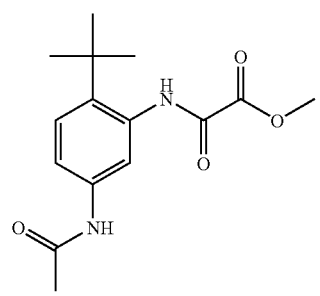

To a suspension of N-(5-Amino-2-tert-butyl-phenyl)-oxalamic acid methyl ester (1.10 g, 4.39 mmol) in pyridine (5 mL) at room temperature was added 1.1 equiv of Acetic anhydride (0.45 mL, 4.83 mmol). After stirring at room temperature for 30 min, the reaction mixture was treated with 0.5N CuSO₄ (50 mL), stirred for 5 min and then partitioned between EtOAc/water. The organic phase was washed with 0.5N HCl (2×25 mL), and saturated NaCl solution (50 mL), dried over Na₂SO₄ and evaporated to dryness to give the tittle compound as a white foam (1.28 g, >98%). TLC (70% EtOAc/Hexane) $R_f$=0.43; ¹HNMR (CDCl₃) δ 9.26 (br.s, 1H), 7.90 (d, J=2.4 Hz, 1H), 7.65–7.61 (dd, J=8.7, 2.4 Hz, 1H), 7.47 (br.s, 1H), 7.35 (d, J=8.7 Hz, 1H), 4.10 (s, 3H), 2.16 (s, 3H), 1.44 (s, 9H); MS(ES) for $C_{15}H_{20}N_2O_4$ (MW=292.33): positive 293 (MH+).

Part E: N-(5-Amino-2-tert-butyl-phenyl)-oxalamic acid

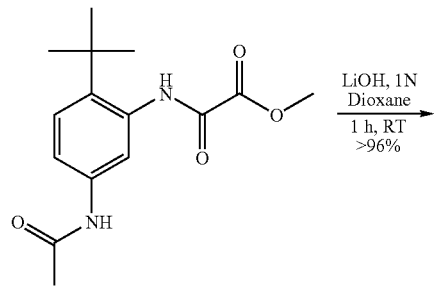

To a suspension of N-(5-Acetylamino-2-tert-butyl-phenyl)-oxalamic acid methyl ester (1.28 g, 4.38 mmol) in 1,4-Dioxane (5 mL) at room temperature was added 1.05 equiv of 1.0N LiOH (4.60 mL, 4.60 mmol). After stirring at room temperature for 30 min, the reaction mixture was treated with 0.5N HCl (20 mL), stirred for 5 min and then partitioned between EtOAc/water. The organic phase was washed with saturated NaCl solution (50 mL), dried over Na₂SO₄ and evaporated to dryness. The oily residue was recrystallized from CH₂Cl₂/Hexane to give the title compound as a white fine crystal (1.74 g, 96%). ¹HNMR (DMSO-d₆) δ 10.05 (s, 1H), 9.96 (s, 1H), 7.50 (d, J=2.1 Hz, 1H), 7.42 (dd, J=9.0, 2.1 Hz, 1H), 7.33 (d, J=8.7 Hz, 1H), 2.02 (s, 3H), 1.30 (s, 9H); MS(ES) for $C_{14}H_{18}N_2O_4$ (MW=278.30): negative 277 ([M–H]⁻).

Part F: (2S)-2-[(5-Acetylamino-2-tert-butyl-phenylaminooxalyl)-amino]-propaneperoxoic acid methyl ester

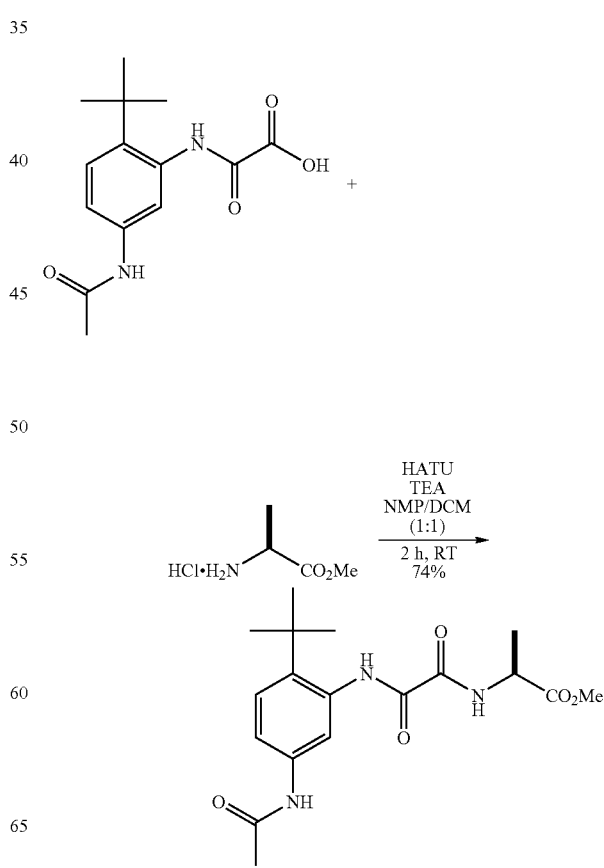

To a solution of N-(5-Amino-2-tert-butyl-phenyl)-oxalamic acid (0.35 g, 1.36 mmol) in CH₂Cl₂/1-methyl-2-pyrolidinone (NMP) (1:1) (3 mL) at room temperature under N₂ was added 1.5 equiv O-(7-Azabenzotriazol-1-yl)-N,N,N',N'-tetramethyluronium hexafluorophosphate (HATU) (0.72 g, 1.89 mmol). The mixture solution was stirred at room temperature under N₂ for 45 min before addition of HClH-Ala-OMe (0.16 g, 1.51 mmol), followed by Et₃N (0.53 mL, 3.78 mmol). After stirring at room temperature for 2 hrs, the mixture was partitioned between EtOAc-water. The organic phase was washed with water, 5% KHSO₄, saturated NaHCO₃, and saturated NaCl solutions, dried over anhydrous Na₂SO₄ and evaporated to give crude title compound. The residue was purified by flask column chromatography on silica gel eluting with EtOAc/Hexane (20–60%) to give the tittle compound (0.34 g, 74%) as a white solid. TLC (80% EtOAc/Hexane) $R_f$=0.51; ¹HNMR (CDCl₃) δ 9.63 (br.s, 1H), 8.11 (d, J=7.8 Hz, 1H), 8.01 (d, J=2,4 Hz, 1H), 7.60 (dd, J=8.4, 2.1 Hz, 1H), 7.50 (s, 1H), 7.35 (d, J=98.7 Hz, 1H), 4.71–4.61 (dq, J=15, 7.5 Hz, 1H), 3.80 (s, 3H), 2.15 (s, 3H), 1.55 (d, J=7.2 Hz, 3H), 1.44 (s, 9H). MS(ES) for C₁₈H₂₅N₃O₆ (MW=363.41): positive 381 ([M+NH₄]⁺).

Part G: (2S)-2-[(5-Acetylamino-2-tert-butyl-phenylaminooxalyl)-amino]-propionic acid

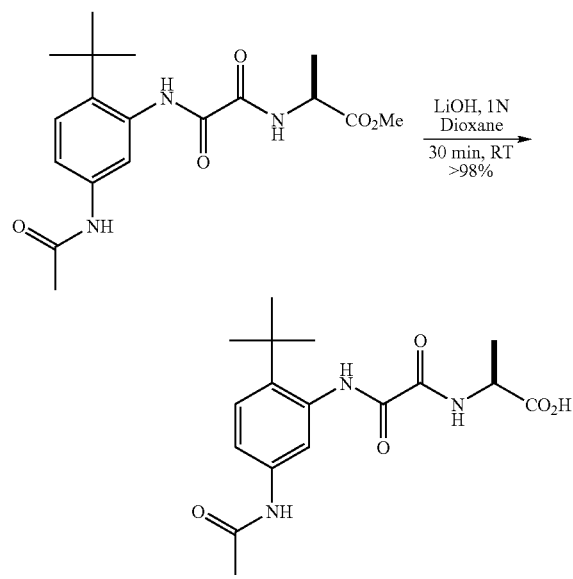

To a suspension of (2S)-2-[(5-Acetylamino-2-tert-butyl-phenylaminooxalyl)-amino]-propionic acid methyl ester (0.32 g, 0.88 mmol) in 1,4-Dioxane (2 mL) at room temperature was added 1.05 equiv of 1.0N LiOH (0.92 mL, 0.92 mmol). After stirring at room temperature for 30 min, the reaction mixture was treated with 0.5N HCl (10 mL), stirred for 5 min and then partitioned between EtOAc/water. The organic phase was washed with saturated NaCl solution (50 mL), dried over Na₂SO₄ and evaporated to dryness. The oil residue was recrystallized from EtOAc/Hexane to give the title compound as a white fine powder (0.31 g, 99%). ¹HNMR (CDCl₃) δ 9.66 (s, M1), 8.42 (d, J=8.4 Hz, 1H), 8.14 (s, 1H), 7.91 (s, 1H), 7.55–7.52 (dd, J=8.4, 1.8 Hz, 1H), 7.33 (d, J=9.0 Hz, 1H), 4.72–4.63 (q, J=7.5 Hz, 11), 4.20–3.90 (bs, 1H), 2.13 (s, 3H), 1.53 (d, J=7.2 Hz, 3H), 1.41 (s, 3H); MS(ES) for C₁₄H₁₈N₂O₄ (MW=349.38): negative 348 ([M−H]⁻).

Part H: 3-Benzyloxycarbonylamino-N-methoxy-N-methyl-succinamic acid tert-butyl ester

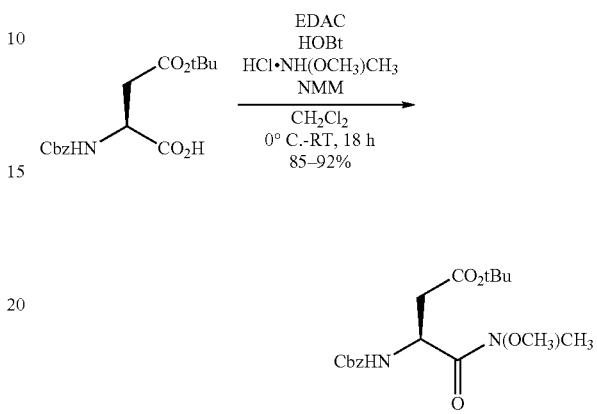

To a solution of 2-Benzyloxycarbonylamino-succinic acid 4-tert-butyl ester (15.00 g, 46.39 mmol) in CH₂Cl₂ (150 mL) at 0° C. under N₂ was added 1.2 equiv of 1-(3-Dimethylaminopropyl)-3-ethylcarbodiimide.HCl (EDAC) (10.67 g, 55.67 mmol) and 1.1 equiv of HOBt.H₂O (7.81 g, 51.03 mmol). The mixture was stirred at 0° C. under N₂ for 15 min before addition of HCl.HN(OMe)Me (5.88 g, 60.31 mmol), followed by 4-Methylmorpholine (NMM) (7.65 mL, 69.59 mmol). After stirring at 0° C. to room temperature for 18 hrs, the mixture was partitioned between EtOAc/water. The organic phase was washed with water, 5% KHSO₄, saturated NaHCO₃, and saturated NaCl solutions, dried over anhydrous Na₂SO₄ and evaporated to give crude title compound. The residue was recrystallized from Et₂O/n-Hexane to give the tittle compound (14.61 g, 86%) as a white solid. TLC (50% EtOAc/Hexane) $R_f$=0.58; ¹HNMR (CDCl₃) δ 7.34 (m, 5H), 5.64 (d, J=9.3 Hz, 1H), 5.15–5.05 (dd, J=18.3, 12.3 Hz, 2H), 5.05–5.00 (m, 1H), 3.78 (s, 3H), 3.22 (s, 1H), 2.74–2.68 (dd, J=15.0, 5.4 Hz, 1H), 2.58–2.51 (dd, J=15.6, 7.2 Hz, 1H, 1.42 (s, 9H). MS(ES) for C₁₈H₂₆N₂O₆ (MW=366.4): positive 367 (MH⁺).

Part I: 3-Benzyloxycarbonylamino-4-oxo-butyric acid tert-butyl ester

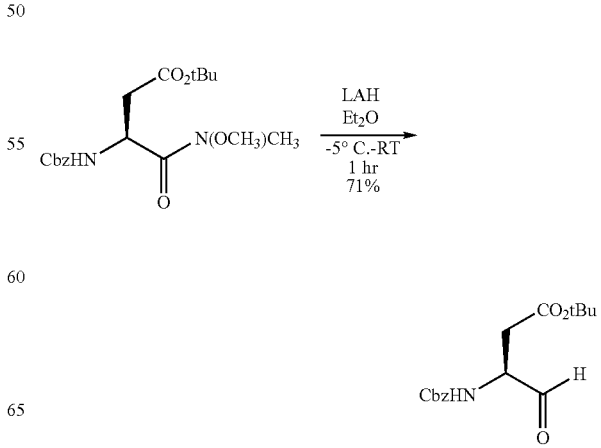

To a suspension of 3-Benzyloxycarbonylamino-N-methoxy-N-methyl-succinamic acid tert-butyl ester (10.00 g, 27.29 mmol) in Ethyl ether (200 mL) at −5° C. was added dropwise 0.5 equiv of 1.0M Lithium aluminum hydride (LAH) in ethyl ether (13.65 mL, 13.65 mmol). After stirring at −5° C. to room temperature for 1 hr. the reaction mixture was treated with 5% $KHSO_4$ (200 mL), stirred for 5 min and then partitioned between EtOAc/water. The organic phase was washed with saturated NaCl solution (200 mL), dried over $Na_2SO_4$ and evaporated to dryness. The residue was purified by flask column chromatography on silica gel eluting with EtOAc/Hexane (20–80%) to give the tittle compound (6.00 g, 71%) as a clear oil. TLC (40% EtOAc/Hexane) $R_f$=0.38; $^1$HNMR ($CDCl_3$) δ 9.62 (s, 1H), 7.39 (s, 5H), 5.88 (d, J=7.8 Hz, 1H), 5.15 (s, 2H), 4.43–4.37 (dt, J=9.3, 4.5 Hz, 1H), 3.01–2.94 (dd, J=17.4, 4.8 Hz, 1H), 2.80–2.73 (dd, J=17.4, 4.8 Hz, 1H), 1.42 (s, 9H). MS(ES) for $C_{16}H_{21}NO_5$ (MW=307.14): positive 308 (MH+).

Part J:
3-Benzyloxycarbonylamino-4,4-diethoxy-butyric acid tert-butyl ester

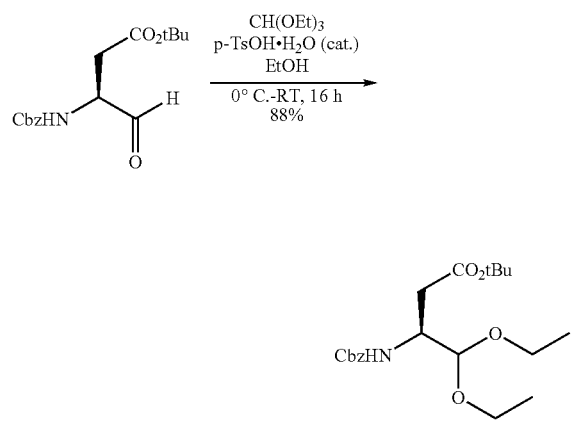

To a suspension of 3-Benzyloxycarbonylamino-4-oxobutyric acid tert-butyl ester (4.46 g, 14.53 mmol) in Ethanol (40 mL) at 0° C. was added 0.20 equiv $TsOH.H_2O$ (0.55 g, 2.91 mmol) and followed by dropwise 8.0 equiv of $CH(OEt)_3$ (19.34 mL, 116.25 mmol). After stirring at 0° C. to room temperature for 16 hrs, the reaction mixture was treated with saturated $NaHCO_3$ (100 mL), stirred for 5 min and then partitioned between EtOAc/water. The organic phase was washed with saturated NaCl solution (200 mL), dried over $Na_2SO_4$ and evaporated to dryness. The residue was purified by flask column chromatography on silica gel eluting with EtOAc/Hexane (20%) to give the tittle compound (4.88 g, 88%) as a clear oil. TLC (30% EtOAc/Hexane) $R_f$=0.33; $^1$HNMR ($CDCl_3$) δ 7.38 (m, 5H), 5.28 (d, J=9.9 Hz, 1H), 5.15–5.05 (dd, J=18.0, 12.3 Hz, 2H), 4.48 (d, J=3.6 Hz, 1H), 4.21–4.16 (m, 1H), 3.75–3.65 (m, 2H), 3.59–3.47 (m, 2H), 2.59–2.46 (dd, J=15.6, 5.7 Hz, 2H), 1.42 (s, 9H), 1.21–1.16 (t, J=6.9 Hz, 3H).

Part K: 3-Amino-4,4-diethoxy-butyric acid tert-butyl ester

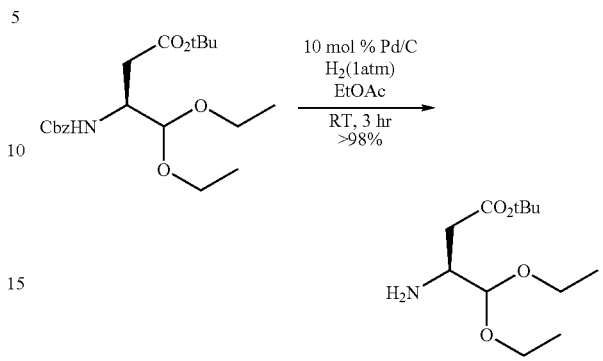

To a suspension of 3-Benzyloxycarbonylamino-4,4-diethoxy-butyric acid tert-butyl ester (0.50 g, 1.31 mmol) in Ethyl acetate (50 mL) at room temperature was added 10 mol % Pd/C (~0.05 g). The reaction flask was purged between $H_2$ (1atm) and vacuum three times before stirring under $H_2$ (1atm) at room temperature. After stirring at room temperature for 3 hrs, the reaction mixture was filtered through celite and then evaporated to dryness to give the title compound (0.32 g, 98%) as a clear oil. $^1$HNMR ($CDCl_3$) δ 4.29 (d, J=5.4 Hz, 1H), 3.79–3.67 (m, 2H), 3.61–3.49 (m, 2H), 3.29–3.21 (m, 1H), 2.60–2.53 (dd, J=16.2, 4.2 Hz, 1H), 2.30–2.21 (dd, J=16.2, 9.0 Hz, 1H), 1.46 (s, 9H), 1.25–1.19 (m, 3H).

Part L: (3S)-3-{(2S)-2-[(5-Acetylamino-2-tert-butylphenylaminooxalyl)-amino]-propionylamino}-4,4-diethoxy-butyric acid tert-butyl ester

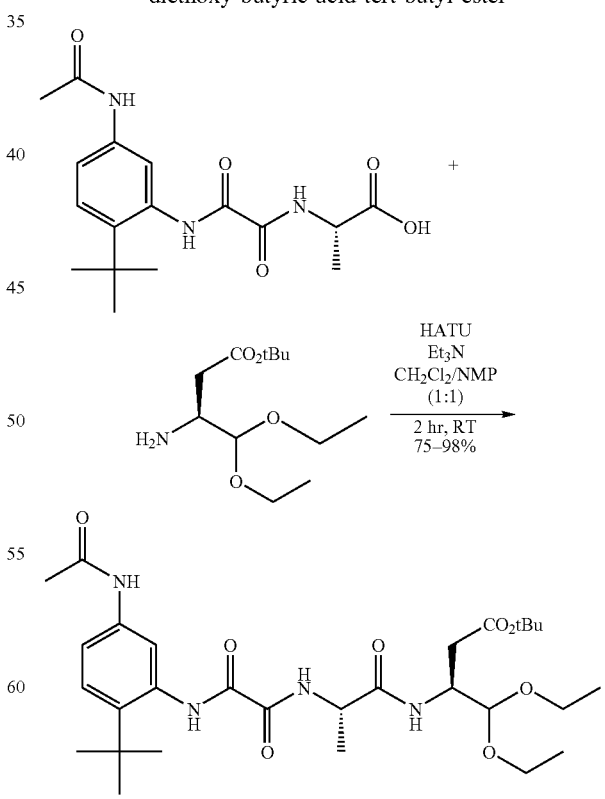

To a solution of (2S)-2-[(5-Acetylamino-2-tert-butyl-phenylaminooxalyl)-amino]-propanepanoic acid (0.16 g, 0.46 mmol) in CH$_2$Cl$_2$/NMP (1:1, 3 mL) at room temperature under N$_2$ was added 1.5 equiv HATU (0.26 g, 0.69 mmol). The mixture was stirred at room temperature under N$_2$ for 45 min before addition of 3-Amino-4,4-diethoxy-butyric acid tert-butyl ester (0.13 g, 0.51 mmol), followed by Et$_3$N (0.19 mL, 1.38 mmol). After stirring at room temperature for 3 hrs, the mixture was partitioned between EtOAc-water. The organic phase was washed with water, 5% KHSO$_4$, saturated NaHCO$_3$, and saturated NaCl solutions, dried over anhydrous Na$_2$SO$_4$ and evaporated to give crude title compound. The residue was purified by flask column chromatography on silica gel eluting with EtOAc/Hexane (30–70%) to give the title compound (0.26 g, 99%) as a white foam. TLC (70% EtOAc/Hexane) R$_f$=0.31; $^1$HNMR (CDCl$_3$) δ 9.80 (bs, 1H), 8.81 (d, J=8.1 Hz, 1H), 8.54 (s, 1H), 8.00 (d, J=2.1 Hz, 1H), 7.86–7.83 (dd, J=8.7, 2.1 Hz, 1H), 7.37–7.34 (d, J=8.7 Hz, 1H), 6.85 (d, J=8.7 Hz, 1H), 4.61–4.33 (m, 3H), 3.77–3.39 (m, 4H), 2.50–2.46 (dd, J=6.3, 2.4 Hz, 2H), 2.18 (s, 3H). 1.50 (d, J=6.9 Hz, 3H), 1.46 (s, 9H); MS(ES) for C$_{29}$H$_{46}$N$_4$O$_8$ (MW=578.70): positive 596 ([M+NH$_4$]$^+$).

Part M: N-(5-Acetylamino-2-tert-butyl-phenyl)-N'-[1-(2-hydroxy-5-oxo-tetrahydro-furan-3-ylcarbamoyl)-ethyl]-oxalamide

EXAMPLE 221

N-(5-Acetylamino-2-tert-butyl-phenyl)-N'-[1-(2-ethoxy-5-oxo-tetrahydro-furan-3-ylcarbamoyl)-ethyl]-oxalamide

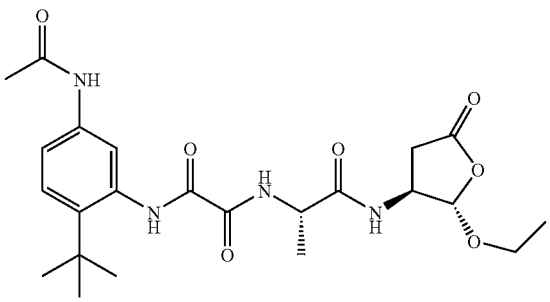

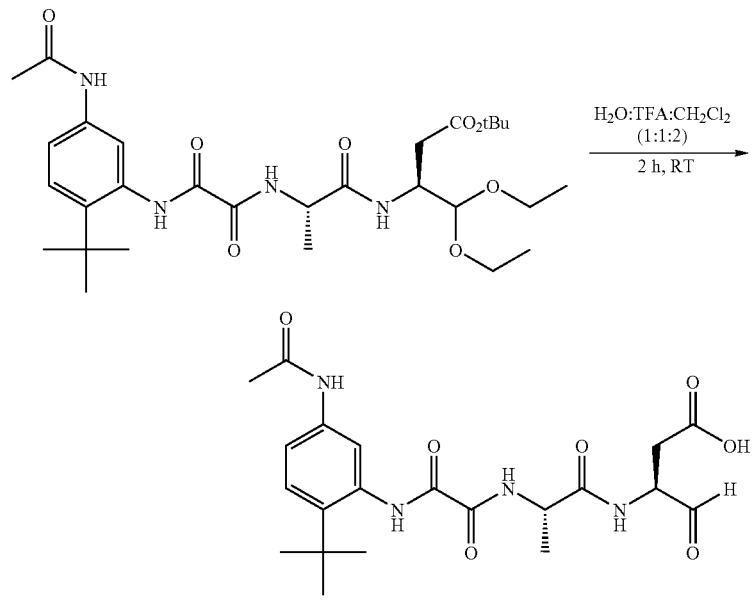

The starting material, (3S)-3-{(2S)-2-[(5-Acetylamino-2-tert-butyl-phenylaminooxalyl)-amino]-propionylamino}-4,4-diethoxy-butyric acid tert-butyl ester (0.24 g, 0.42 mmol) was stirred in Water/TFA/CH$_2$Cl$_2$ (1:1:2, 4 mL) at room temperature. After stirring for 2 hrs, the reaction solution was concentrated in vacuo to dryness yielding the crude title compound. The residue was purified by preparative HPLC (C$_{18}$ column eluding with 10–90% of 0.1% aqueous formic acid/ACN over 60 min) to give the title compound (0.09 g, 46%) as a white solid. MS(ES) for C$_{21}$H$_{28}$N$_4$O$_7$ (MW=448.47): positive 449 ([MH$^+$]).

Part A:
(2-Ethoxy-5-oxo-tetrahydro-furan-3-yl)-carbamic acid benzyl ester

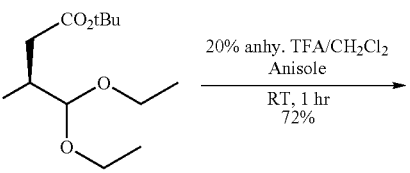

-continued

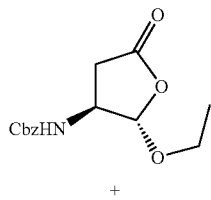

+

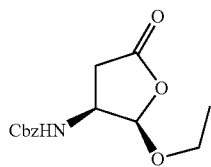

To a suspension of 3-Benzyloxycarbonylamino-4,4-diethoxy-butyric acid tert-butyl ester (4.61 g, 12.09 mmol) in 20% anhydrous TFA/CH$_2$Cl$_2$ (20 mL) at room temperature was added Anisole (0.4 mL). After stirring at room temperature for 1 hr, the reaction mixture was evaporated to dryness to give the crude title compounds as a clear oil. The residue was purified by flask column chromatography on silica gel eluting with EtOAc/Hexane (10–30%) to give:

(2S,3 S)-2-Ethoxy-5-oxo-tetrahydro-furan-3-yl)-carbamic acid benzyl ester (1.54 g, 46%) as a clear oil. TLC (30% EtOAc/Hexane) R$_f$=0.52; $^1$HNMR (CDCl$_3$) δ 7.38 (m, 5H), 5.40 (br.s, 1H), 5.11 (br.s, 2H), 5.00 (br.s, 2H), 4.21 (t, J=6.6 Hz, 1H), 3.90–3.80 (dd, J=7.2, 2.4 Hz, 1H), 3.66–3.61 (d, J=8.1 Hz, 1H), 2.90–2.81 (dd, J=17.1, 8.4 Hz, 1H), 2.51–2.41 (dd, J=17.4, 10.5 Hz, 1H), 1.24 (t, J=6.9 Hz, 3H). MS (ES) for C$_{14}$H$_{17}$NO$_5$ (MW=279.29): positive 278 ([MH$^+$]).

(2R,3 S)-(2-Ethoxy-5-oxo-tetrahydro-furan-3-yl)-carbamic acid benzyl ester (0.89 g, 26%) as a clear oil. TLC (30% EtOAc/Hexane) R$_f$=0.42 $^1$HNMR (CDCl$_3$) δ 7.37 (m, 5H), 5.43 (d, J=5.1 Hz, 1H), 5.11 (br.s, 2H), 5.34 (d, J=9.3 Hz, 1H), 4.61–4.50 (m, 1H), 3.95–3.85 (dq, J=9.3, 6.9 Hz, 1H), 3.68–3.58 (dq, J=9.3, 6.9 Hz, 1H), 2.90–2.81 (dd, J=17.1, 8.4 Hz, 1H), 2.51–2.41 (dd, J=17.4, 10.5 Hz, 1H), 1.24 (t, J=6.9 Hz, 3H). MS(ES) for C$_{14}$H$_{17}$NO$_5$ (MW=279.29): positive 278 ([MH$^+$]).

Part B:
(4S,5S)-4-Amino-5-ethoxy-dihydro-furan-2-one

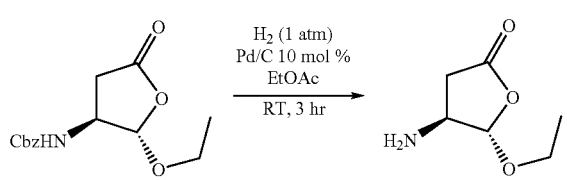

To a suspension of (2S,3S)-(2-Ethoxy-5-oxo-tetrahydro-furan-3-yl)-carbamic acid benzyl ester (0.43 g, 1.54 mmol) in Ethyl acetate (50 mL) at room temperature was added 10 mol % Pd/C (~0.05 g). The reaction flask was purged between H$_2$ (1atm) and vacuum three times before stirring under H$_2$ (1atm) at room temperature. After stirring at room temperature for 3 hrs, the reaction mixture was filtered through celite and then evaporated to dryness to give the title compound (0.21 g, 94%) as a clear oil. $^1$HNMR (CDCl$_3$) δ 5.17 (d, J=1.2 Hz, 1H), 3.93–3.82 (dq, J=9.6, 7.2 Hz, 1H), 3.67–3.57 (dq, J=9.3, 6.9 Hz, 1H), 2.95–287 (dd, J=17.7, 6.9 Hz, 1H), 2.56–2.19 (dd, J=17.4, 2.7 Hz, 1H), 1.26–1.21 (t, J=7.2 Hz, 3H). MS(ES) for C$_6$H$_{11}$NO$_3$ (MW=145.16): positive 146 ([MH$^+$]).

Part C: (4S.
5R)-4-Amino-5-ethoxy-dihydro-furan-2-one

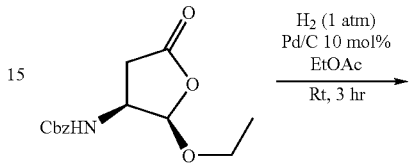

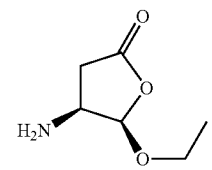

To a suspension of (2R, 3S)-(2-Ethoxy-5-oxo-tetrahydro-furan-3-yl)-carbamic acid benzyl ester (0.22 g, 0.86 mmol) in Ethyl acetate (25 mL) at room temperature was added 10 mol % Pd/C (~0.03 g). The reaction flask was purged between H$_2$ (1atm) and vacuum three times before stirring under H$_2$ (1atm) at room temperature. After stirring at room temperature for 3 hrs, the reaction mixture was filtered through celite and then evaporated to dryness to give the title compound (0.12 g, 97%) as a clear oil.

$^1$HNMR (CDCl$_3$) δ 5.31 (d, J=5.1 Hz, 1H), 3.98–3.87 (dq, J=9.6, 7.2 Hz, 1H), 3.76–3.59 (m, 2H), 3.52–3.45 (q, J=7.2 Hz, 1H), 2.72–2.64 (dd, J=17.4, 8.1 Hz, 1H), 2.45–2.36 (dd, J=17.1, 10.2 Hz, 1H), 1.29–1.24 (t, J=6.9 Hz, 3H). MS(ES) for C$_6$H$_{11}$NO$_3$ (MW=145.16): positive 146 ([MH$^+$]).

Part D: N-(5-Acetylamino-2-tert-butyl-phenyl)-N'-[1-(2-ethoxy-5-oxo-tetrahydro-furan-3-ylcarbamoyl)ethyl]-oxalamide

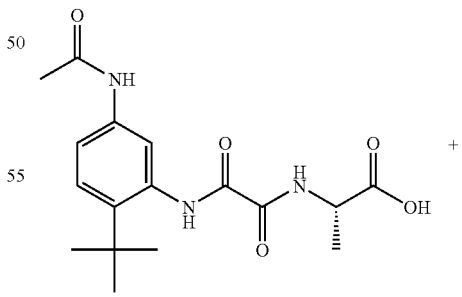

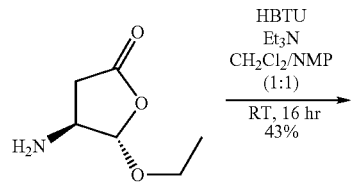

-continued

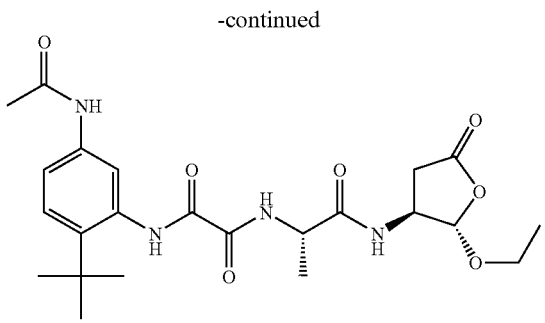

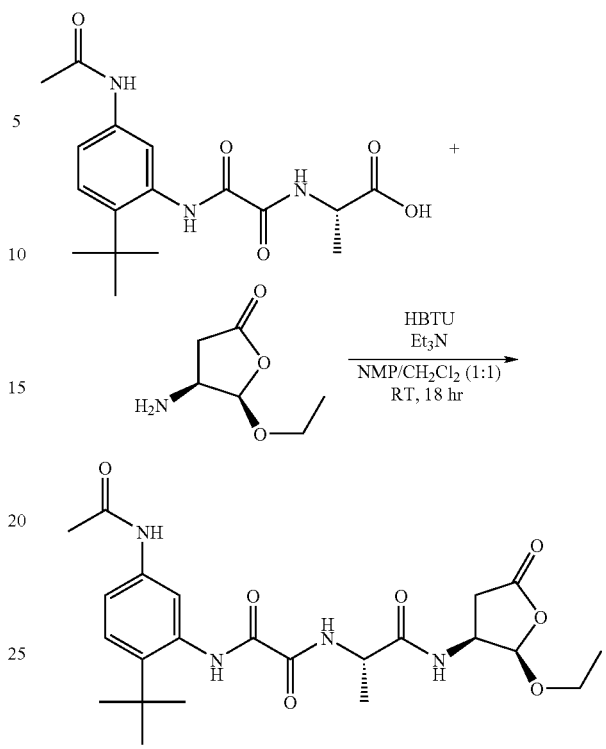

To a solution of (2S)-2-[(5-Acetylamino-2-tert-butyl-phenylaminooxalyl)-amino]-propanoic acid (0.24 g, 0.68 mmol) in CH$_2$Cl$_2$/NMP (1:1, 3 mL) at room temperature under N$_2$ was added 1.5 equiv O-benzotriazol-1-yl-N,N,N', N'-tetramethyluronium hexafluorophosphate (HBTU) (0.26 g, 0.69 mmol). The mixture was stirred at room temperature under N$_2$ for 45 min before added (4S,5S)-4-Amino-5-ethoxy-dihydro-furan-2-one (0.12 g, 0.82 mmol) and followed by Et$_3$N (0.24 mL, 1.70 mmol). After stirring at room temperature for 16 hrs, the mixture was partitioned between EtOAc-water. The organic phase was washed with water, and saturated NaCl solutions, dried over anhydrous Na$_2$SO$_4$ and evaporated to give crude title compound. The residue was purified by flask column chromatography on silica gel eluding with EtOAc/Hexane (60–80%) to give the title compound (0.14 g, 43%) as a white solid. TLC (100% EtOAc) R$_f$=0.51; $^1$HNMR (CDCl$_3$) δ 9.82 (t, J=10.5 Hz, 1H), 8.85–8.44 (m, 2H), 8.00–7.94 (m, 1H), 7.80–7.68 (m, 1H), 7.38–7.34 (m, 1H), 5.41–5.33 (dd, J=22.2, 4.8 Hz, 1H), 4.74–4.63 (m, 1H), 4.59–4.35 (m, 1H), 3.88–3.77 (dq, J=9.6, 7.2 Hz, 1H), 3.70–3.56 (m, 1H), 3.39–3.22 (m, 1H). 3.03–2.88 (ddd, J=18.3, 7.8, 2.4 Hz, 1H), 2.56–2.35 (m, 1H), v 2.19 (s, 3H), 1.57–1.52 (dd, J=7.2, 3.0 Hz, 3H), 1.45 (s, 9H); MS(ES) for C$_{23}$H$_{32}$N$_4$O$_7$ (MW=476.52): positive 477 ([MH$^+$]).

EXAMPLE 222

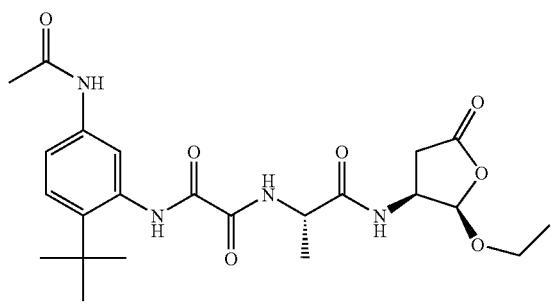

N-(5-ACETYLAMINO-2-TERT-BUTYL-PHENYL)-N'-[1-(2-ETHOXY-5-OXO-TETRAHYDRO-FURAN-3-YLCARBAMOYL)-ETHYL]-OXALAMIDE

To a solution of (2S)-2-[(5-Acetylamino-2-tert-butyl-phenylaminooxalyl)-amino]-propanoic acid (0.08 g, 0.23 mmol) in CH$_2$Cl$_{21}$NMP (1:1, 1.5 mL) at room temperature under N$_2$ was added 1.5 equiv HBTU (0.13 g, 0.35 mmol). Mixture solution was stirred at room temperature under N$_2$ for 45 nm before added (4S,5R)-4-Amino-5-ethoxy-dihydro-furan-2-one (0.05 g, 0.35 mmol) and followed by Et$_3$N (0.10 mL, 0.69 mmol). After stirring at room temperature for 18 hrs, the mixture was partitioned between EtOAc-water. The organic phase was washed with water, and saturated NaCl solutions, dried over anhydrous Na$_2$SO$_4$ and evaporated to give crude title compound. The residue was purified by flask column chromatography on silica gel eluting with EtOAc/Hexane (60–90%) to give the title compound (0.10 g, 91%) as a white solid. TLC (100% EtOAc) R$_f$=0.52; $^1$HNMR (CDCl$_3$) δ 9.77 (s, 1H), 8.70–8.65 (t, J=8.1 Hz, 1H), 8.48 (s, 1H), 8.00 (s, 1H), 7.82 (d, J=11.4 Hz, 1H), 7.39–7.36 (d, J=8.7 Hz, 1H), 7.06 (d, J=7.5 Hz, 1H), 1H), 4.49 (d, J=5.1 Hz, 1H), 4.78–4.57 (m, 2H), 3.98–3.86 (m, 1H), 3.72–3.57 (m, 1H), 2.49–2.35 (m, 1H), 2.17 (s, 3H), 2.08–1.97 (m, 1H), 1.55 (d, J=7.2 Hz, 3H) 1.46 (s, 9H), 1.28–1.22 (t, J=14.1 Hz, 3H). MS(ES) for C$_{23}$H$_{32}$N$_4$O$_7$ (MW=476.52): positive 477([MH$^+$]), 499 ([M+Na]$^+$).

EXAMPLE 223

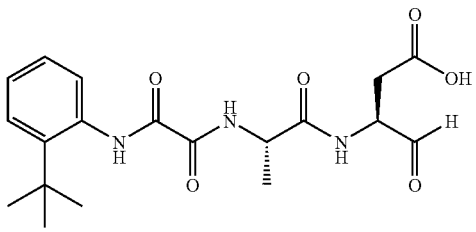

N-(2-TERT-BUTYL-PHENYL)-N'-[1-(2-ETHOXY-5-OXO-TETRAHYDRO-FURAN-3-YLCARBAMOYL)-ETHYL]-OXALAMIDE

Part A: Methyl 2-(2-tert-Butylphenylamino)-2-oxoacetate

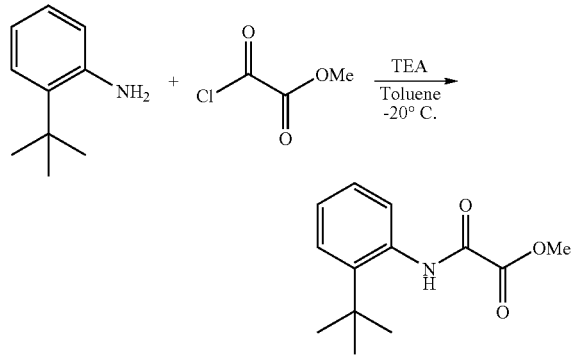

A 3-L, 3-necked round-bottomed flask, equipped with a mechanic stirrer and a thermal probe (under nitrogen) was charged with 2-tert-Butylaniline (109 g, 114 mL, 732 mmoles), triethylamine (81.4 g, 112 mL, 804 mmoles, 1.1 equiv.) and toluene (600 mL). The resulting mixture was stirred at a moderate speed at −30° C. An additon funnel was charged with Methyl chlorooxoacetate (100 g, 816 mmoles, 1.11 equiv.) with toluene (200 mL), and the mixture added to the reaction mixture at such a rate that the internal batch temperature is less than −20° C. After addition, the reaction was warmed to room temperature for an hour, quenched with water, then partitioned between EtOAc/water. The aqueous phase was extracted with EtOAc (200 mL), and the combined organic layers were washed successively with KHSO$_4$ (200 mL), NaHCO$_3$ (sat'd) (200 mL) and brine (200 mL), then dried the organic over MgSO$_4$. The organic phase was concentrated by rotary evaporation, yielding the title compound as a pale yellow solid [Methyl 2-(2-tert-Butylphenylamino)-2-oxoacetate, 160 g, 93.1%]. MP 61.7–63.6° C. IR (KBr) 3409, 2954, 1736, 1724, 1530, 1299, 1166, 766 cm$^{-1}$; $^1$H NMR (300 MHz, CDCl$_3$): δ(ppm): 9.20 (br, 1H), 7.97 (dd, J=7.8 Hz, J'=1.8 Hz, 1H), 7.43 (dd, J=7.8 Hz, J'=1.8 Hz, 1H), 7.31–7.16 (m, 2H), 4.00 (s, 3H), 1.47(s, 9H). The product thus obtained can be used directly for the subsequent reaction.

Part B: 2-(2-tert-Butyl phenylamino)-2-oxoacetic acid

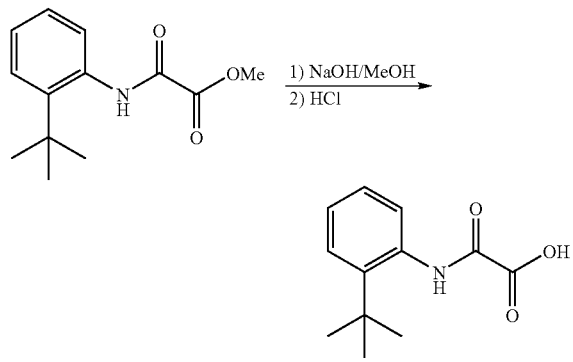

A 3-L, 3-necked round-bottomed flask, equipped with a mechanic stirrer and a thermal probe (under nitrogen) was charged with Methyl 2-(2-tert-Butylphenylamino)-2-oxoacetate (154 g, 655 mmoles) and MeOH (1000 mL). The resulting mixture was stirred at a moderate speed at room temperature. A solution of 1N NaOH/MeOH (800 mL) was added dropwise to the reaction mixture via addition funnel. After 1 hour, agitation was stopped, and the suspension transferred to a filtration funnel and filtered to afford a white solid. This solid was then taken up in water (1200 mL) and the pH adjusted to 1.5–2 with addition of conc. HCl with stirring. After mixing for 1 hour, filtration and drying yielded the title compound as a white crystalline mass (127 g, 574 mmoles, 87.6%). TLC (silica F254, 3/1 v/v dichloromethane/MeOH, detection 254 nm) showed one spot and HPLC confirmed that. MP 110.9–112.6° C.; IR (KBr) 3405, 2973, 1688, 1548, 1300, 757 cm$^{-1}$; $^1$H NMR (300 MHz, CDCl$_3$): δ (ppm): 9.37 (br, 1H), 7.91 (dd, J=7.8 Hz, J'=1.8 Hz, 1H), 7.44 (dd, J=7.8 Hz, J'=1.8 Hz, 1H), 7.25 (m, 2H), 1.46 (s, 9H); $^{13}$C (300 MHz, CDCl$_3$): δ (ppm): 160.87, 155.24, 141.18, 133.19, 126.92, 126.69, 126.63, 124.24, 34.21, 30.49.

Part C: Methyl(2S)-2-({N-[2-(tert-butyl)phenyl]carbamoyl}carbonylamino)propanoate

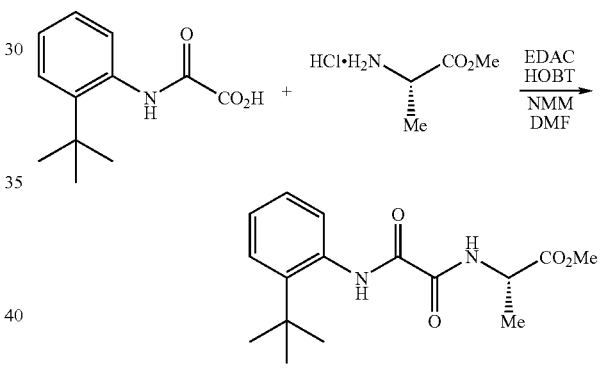

A 3-L, 3-necked round-bottomed flask, equipped with a mechanic stirrer and a thermal probe (under nitrogen) was charged with the following solids: 2-(2-tert-Butylphenylamino)-2-oxoacetate (70.008 g, 316.402 mmol), alanine methyl ester hydrochloride (44.368 g, 317.862 mmol), hydroxybenzotriazole hydrate (HOBT) (47.324 g, 350.210 mmol), and 1-[3-(Dimethylamino)propyl]-3-ethylcarbodiimide hydrochloride (EDAC.HCl) (121.668 g, 635.4 mmol). N,N'-dimethylformamide (DMF) (1250 mL) was added via graduated cylinder, and the reaction mixture stirred to partially dissolve and suspend the solid reagents. N-methylmorpholine (108 mL, 99.36 g, 982 mmol) was then added in one portion via graduated cylinder. After stirring at room temperature for 18 hours, the reaction mixture was partitioned between EtOAc (ca. 600 mL) and 1N HCl (ca. 500 mL). The aqueous phase was washed two times with EtOAc (ca. 300 mL), and the combined organic layers were washed successively with 1N HCl (ca. 300 mL), H$_2$O (ca 300 mL), saturated NaHCO$_3$ (ca. 300 mL), and brine (ca. 300 mL). The resulting pale yellow organic solution was dried over MgSO$_4$, then concentrated to yield a pale yellow crystalline mass (95 g, 97%). TLC: (silica, 1:1 hexanes/EtOAc) R$_f$: 0.54. MP: 60.1–62.1° C.; IR (KBr) 3284, 1747, 1662, 1503, 1216, 755 cm$^{-1}$; $^1$H NMR: (CDCl$_3$, TMS) δ 9.55 (br, 1H), 8.01 (dd, J=7.8 Hz, J'=1.8 Hz, 1H), 7.42 (dd, J=7.8 Hz, J'=2.6 Hz, 1H), 7.15–7.31 (m, 2H), 4.64 (p, J=7.5 Hz, 1H), 3.80 (s, 3H), 1.54 (d, J=7.5 Hz, 3H), 1.46 (s, 9H) ppm.

Part D: (2S)-2-({N-[2-(tert-butyl)phenyl]carbamoyl}carbonylamino)propanoic acid

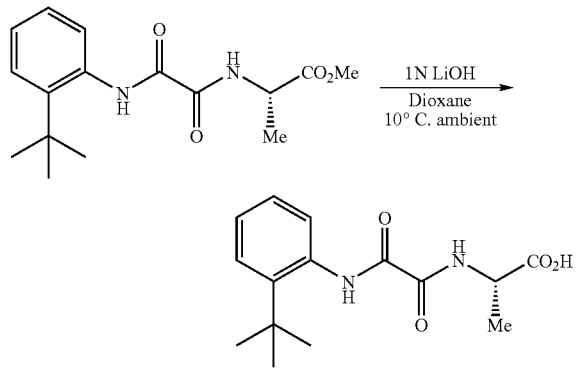

A 3-L, 3-necked round-bottomed flask, equipped with a mechanic stirrer and a thermal probe (under nitrogen) was charged with methyl(2S)-2-({N-[2-(tert-butyl)phenyl]-carbamoyl}carbonylamino)propanoate (85.0 g, 276.5 mmol, dissolved in dioxane (664 mL) and the resulting solution cooled in an ice water bath to 8° C. as monitored by an internal temperature probe. To this was added 1N LiOH (332 mL) in three approximately equal portions such that the temperature did not exceed 10° C. with stirring. The bath was removed and stirring continued over 2.5 hours (as the reaction comes to room temperature) at which point TLC analysis (silica gel, 1:1 EtOAc/hexanes) of the reaction mixture showed that the starting material had been consumed. The reaction mixture was partitioned between 1N HCl (300 mL) and EtOAc (500 mL) in a 2 L separatory funnel and separated. The aqueous phase tested to pH 1–2 by test strip. The resulting aqueous fraction was washed with three (3) additional portions of EtOAc (3×200 mL), then the organic fractions were combined and washed consecutively with 10% citric acid solution (200 mL) and brine (200 mL). The organic phase was then concentrated to a mobile gold oil and further dried under high vacuum 20 h to yield a crude yellow solid mass (about 90 g, very moist). The solid mass was recrystallized from EtOAc/Hexanes, and dried to afford a highly crystalline white solid (58.545 g, 200 mmol, 72.4%). TLC: (silica, 19:1 $CH_2Cl_2$/MeOH) $R_f$: 0.18; MP: 164.4–166.1° C.; IR (KBr) 3323, 1719, 1677, 1517, 1448, 1248, 762 cm$^{-1}$; $^1$H NMR: (300 MHz, $CDCl_3$) δ 9.57 (br, 1H), 8.10 (d, J=7.8 Hz, 1H), 7.97 (dd, J=7.8 Hz, J'=1.8 Hz, 1H), 7.43 (dd, J=7.8 Hz, J'=1.8 Hz, 1H), 7.25–7.30 (m, 1H), 7.15–7.21 (m, 1H), 4.67 (p, J=7.5 Hz, 1H), 1.60 (d, J=7.2 Hz, 3H), 1.46 (s, 9H) ppm; $^{13}$C NMR: (300 MHz, $CDCl_3$) δ 175.71, 159.97, 156.33, 140.92, 133.77, 126.79, 126.47, 126.01, 124.01, 48.31, 34.21, 30.42, 17.50; Elemental Analysis: Calcd for $C_{15}H_{20}N_2O_4$: C, 61.63; H, 6.90; N, 9.58. Found: C, 61.80; H, 6.95; N, 9.50.

Part E: (3S)-3-{(2S)-2-[(2-tert-Butyl-phenylaminooxalyl)-amino]-propionylamino}-4,4-diethoxy-butyric acid tert-butyl ester

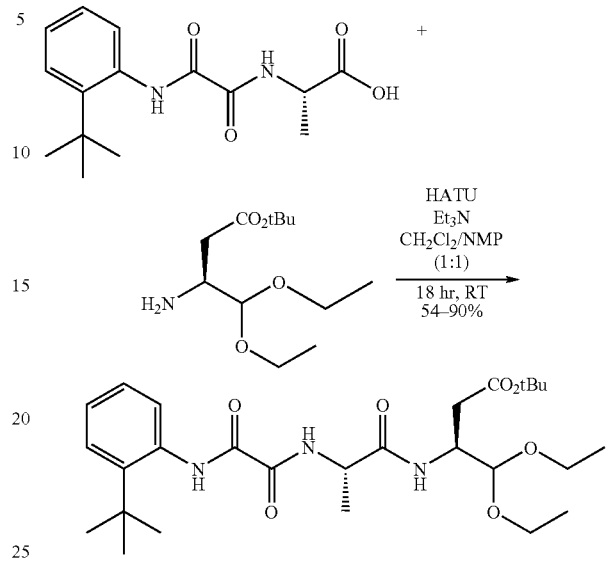

To a solution of (2S)-2-[(2-tert-butyl-phenylaminooxalyl)-amino]-propanoic acid (1.20 g, 4.10 mmol) in $CH_2Cl_2$/NMP (1:1, 10 mL) at room temperature under $N_2$ was added 1.5 equiv HATU (0.26 g, 6.15 mmol). The mixture solution was stirred at room temperature under $N_2$ for 45 min before addition of 3-Amino-4,4-diethoxy-butyric acid tert-butyl ester (1.01 g, 4.10 mmol), followed by $Et_3N$ (1.71 mL, 12.30 mmol). After stirring at room temperature for 16 hrs, the mixture was partitioned between EtOAc-water. The organic phase was washed with water, 5% $KHSO_4$, saturated $NaHCO_3$, and saturated NaCl solutions, dried over anhydrous $Na_2SO_4$ and evaporated to give crude title compound. The residue was purified by flask column chromatography on silica gel eluding with EtOAc/Hexane (20%) to give the tittle compound (1.93 g, 90%) as a white foam. TLC (40% EtOAc/Hexane) $R_f$=0.60; $^1$HNMR ($CDCl_3$) δ 9.54 (s, 1H), 8.09 (d, J=7.5 Hz, 1H), 8.00 (dd, J=8.1, 1.5 Hz, 1H), 7.42 (dd, J=9.6, 1.5 Hz, 1H), 7.27 (dt, J=7.2, 0.9 Hz, 1H), 7.17 (dd, J=7.8, 1.5 Hz, 1H), 6.52 (d, J=9.0 Hz, 1H), 4.53 (d, J=3.9, 1H), 4.50–4.37 (m, 2H), 3.77–3.64 (m, 2H), 3.60–3.46 (m, 2H). 2.52 (d, J=6.9 Hz, 2H), 1.51–1.42 (m, 12H), 1.29–1.16 (m, 6H); MS(ES) for $C_{27}H_{43}N_3O_7$ (MW=521.66): negative 521([M–H]$^-$).

Part F: (2-tert-Butyl-phenyl)-N'-[1-(2-hydroxy-5-oxo-tetrahydro-furan-3-ylcarbamoyl)-ethyl]-oxalamide

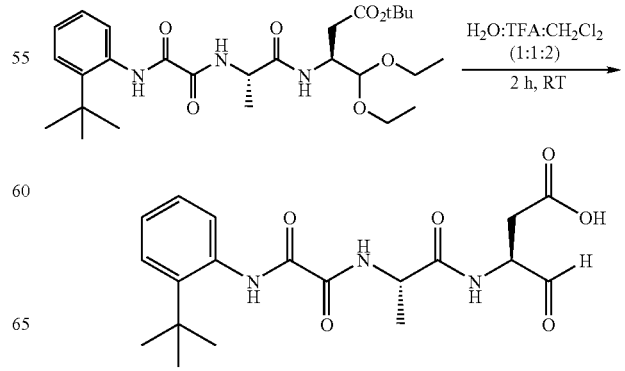

(3S)-3-{(2S)-2-[(2-tert-Butyl-phenylaminooxalyl)-amino]-propionylamino}-4,4-diethoxy-butyric acid tert-butyl ester (1.39 g, 2.66 mmol) was stirred in Water/TFA/CH$_2$Cl$_2$ (30 mL, 1:1:2) at room temperature. After stirring for 2 hrs, the reaction solution was concentrated in vacuo until dryness to give crude title compound. The residue was purified by preparative HPLC (C$_{18}$ column eluding with 30–90% of 0.1% aqueous formic acid/ACN over 60 min) to give the title compound (0.91 g, 87%) as a white solid. LCMS for C$_{19}$H$_{25}$N$_3$O$_6$ (MW=391.42): negative 390.32 ([MH$^-$]). Purity assay using reverse phase Zorbax C8 4.6× 150 mm Rx column over 30 min., with retention time t=10.75 min.

EXAMPLE 225

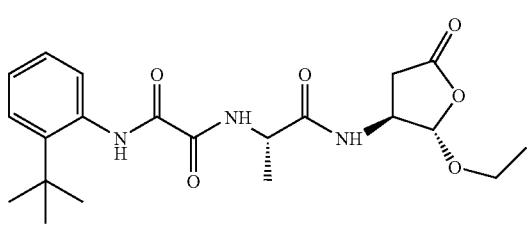

N-(2-TERT-BUTYL-PHENYL)-N'-[1-(2-ETHOXY-5-OXO-TETRAHYDRO-FURAN-3-YLCARBAMOYL)-ETHYL]-OXALAMIDE

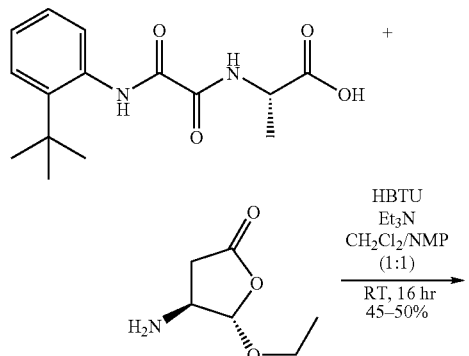

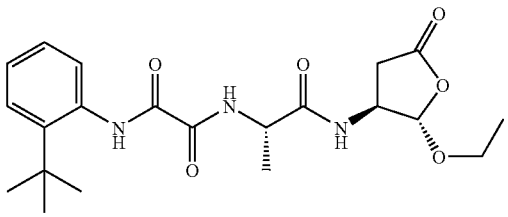

To a solution of (2S)-2-[(2-tert-Butyl-phenylaminooxalyl)-amino]-propanoic acid (1.00 g, mmol) in CH$_2$Cl$_{12}$/NMP (1:1, 3 mL) at room temperature under N$_2$ was added 1.5 equiv HBTU (0.26 g, 3.42 mmol). Mixture solution was stirred at room temperature under N$_2$ for 45 min before added (4S,5S)-4-Amino-5-ethoxy-dihydro-furan-2-one (0.42 g, 2.86 mmol) and followed by Et$_3$N (1.20 mL, 8.58 mmol). After stirring at room temperature for 16 hrs, the mixture was partitioned between EtOAc-water. The organic phase was washed with water, then brine, dried over anhydrous Na$_2$SO$_4$ and evaporated to give crude title compound. The residue was purified by flask column chromatography on silica gel eluting with EtOAc/Hexane (10–40%) to give the title compound (0.53 g, 44%) as a white solid. TLC (50% EtOAc/Hexane) R$_f$=0.45; $^1$HNMR (CDCl$_3$) δ 9.52 (s, 1H), 7.95 (m, 2H), 7.43 (dd, J=7.8, 1.5 Hz, 1H), 7.31–7.25 (dt, J=7.2, 1.2 Hz, 1H), 7.22–7.16 (dt, J=7.5, 1.5 Hz, 1H), 6.88 (d, J=6.9 Hz, 1H), 5.37 (s, 1H), 4.50–4.39 (m, 2H), 3.89–3.79 (dq, J=9.6, 7.2 Hz, 1H), 3.69–3.59 (dq, J=9.3, 6.6 Hz, 1H), 3.07–2.98 (dd, J=18.0, 7.5 Hz, 1H). 2.39–2.33 (dd, J=19.5, 1.2 Hz, 1H), 1.50 (d, J=7.2 Hz, 1H), 1.46 (s, 9H), 1.23 (t, J=7.2 Hz, 3H); LCMS for C$_{21}$H$_{29}$N$_3$O$_6$ (MW=419.47): negative 418 (MH$^-$), positive 420 ([MH$^+$]).

EXAMPLES 226–312

Starting with (3S)-3-[N-(9-fluorenylmethoxycarbonyl) alanyl]amino-4-oxobutanoic acid (tert-butyl)ester semicarbazonyl-4[2'-(4-ethyl-phenoxyacetyl)]aminomethylpolystene (see Example 204, Part A) and following the methods described in Example 204, Part B, or by the procedures set forth in Examples 220–225, the compounds shown below in Table 12 were prepared:

TABLE 12

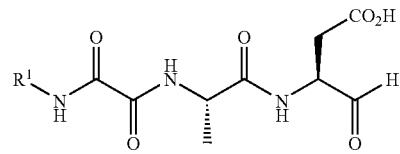

| Ex. | R$^1$ | Formula | MW | MS(ES) Pos | neg |
|---|---|---|---|---|---|
| 226 | (4-Ac)Ph | C$_{17}$H$_{19}$N$_3$O$_7$ | 377.35 | — | 376(M–H) |
| 227 | (4-OH)Ph | C$_{15}$H$_{17}$N$_3$O$_7$ | 351.32 | — | — |
| 228 | (3,5-di-Cl-4-OH)Ph | C$_{15}$H$_{15}$Cl$_2$N$_3$O$_7$ | 420.21 | — | 418/420(M–H) |
| 229 | (3-CF3)PhCH2 | C$_{17}$H$_{18}$F$_3$N$_3$O$_6$ | 417.34 | — | — |
| 230 | (2-F)PhCH2 | C$_{16}$H$_{18}$FN$_3$O$_6$ | 367.33 | — | — |

TABLE 12-continued

| Ex. | R[1] | Formula | MW | MS(ES) Pos | MS(ES) neg |
|---|---|---|---|---|---|
| 231 | (2,4-di-Cl)Ph | $C_{17}H_{19}Cl_2N_3O_6$ | 432.26 | — | — |
| 232 | (3,4-di-OCH3)Ph | $C_{18}H_{23}N_3O_8$ | 409.40 | — | — |
| 233 | CH3 | $C_{10}H_{15}N_3O_6$ | 273.25 | — | — |
| 234 | S-(1-naphthyl)CH(CH3) | $C_{21}H_{23}N_3O_6$ | 413.43 | — | — |
| 235 | R-(1-naphthyl)CH(CH3) | $C_{21}H_{23}N_3O_6$ | 413.43 | — | — |
| 236 | (2-(1-naphthyl))Ph | $C_{25}H_{23}N_3O_6$ | 461.47 | 484 (M+Na) | 460(M–H) |
| 237 | 5-Ph-3-pyrazolyl | $C_{18}H_{19}N_5O_6$ | 401.38 | — | 400(M–H) |
| 238 | 5,6,7,8-tetrahydro-1-naphthyl | $C_{19}H_{23}N_3O_6$ | 389.41 | — | — |
| 239 | Ph2CH | $C_{22}H_{23}N_3O_6$ | 425.44 | — | — |
| 240 | (2-I)Ph | $C_{15}H_{16}IN_3O_6$ | 461.21 | — | — |
| 241 | (2,3,5,6-tetra-Cl)Ph | $C_{15}H_{13}Cl_4N_3O_6$ | 473.10 | — | — |
| 242 | (4-Ph)Ph | $C_{21}H_{21}N_3O_6$ | 411.41 | — | — |
| 243 | (2-PhO)Ph | $C_{21}H_{21}N_3O_7$ | 427.41 | — | — |
| 244 | 2-naphthyl | $C_{19}H_{19}N_3O_6$ | 385.38 | — | — |
| 245 | 1,2,3,4-tetrahydro-1-naphthyl | $C_{19}H_{23}N_3O_6$ | 389.41 | — | — |
| 246 | 1-naphthylCH2 | $C_{20}H_{21}N_3O_6$ | 399.40 | — | — |
| 247 | 1-adamantyl | $C_{19}H_{27}N_3O_6$ | 393.44 | — | — |
| 248 | 4-pyridyl | $C_{14}H_{16}N_4O_6$ | 336.30 | — | — |
| 249 | (2,3,4,5,6-penta-F)Ph | $C_{15}H_{12}F_5N_3O_6$ | 425.27 | — | — |
| 250 | (2-F-4-I)Ph | $C_{15}H_{15}FIN_3O_6$ | 479.20 | — | — |
| 251 | 1,1,3,3-tetramethylbutyl | $C_{17}H_{29}N_3O_6$ | 371.43 | — | — |
| 252 | Ph(CH2)2 | $C_{17}H_{21}N_3O_6$ | 363.37 | — | — |
| 253 | n-heptyl | $C_{16}H_{27}N_3O_6$ | 357.41 | — | — |
| 254 | (4-n-heptyl)Ph | $C_{22}H_{31}N_3O_6$ | 433.50 | — | — |
| 255 | (2,5-di-tBu)Ph | $C_{23}H_{33}N_3O_6$ | 447.53 | — | — |
| 256 | (2-PhCH2)Ph | $C_{22}H_{23}N_3O_6$ | 425.44 | — | — |
| 257 | (2-pyrrolidin-1yl-5-CF3)Ph | $C_{20}H_{23}F_3N_4O_6$ | 472.42 | — | — |
| 258 | 2,3,5,6-tetra-F-4-pyridyl | $C_{14}H_{12}F_4N_4O_6$ | 408.27 | — | — |
| 259 | (2-Ph)Ph | $C_{21}H_{21}N_3O_6$ | 411.41. | 450(M+K) | 410(M–H) |
| 260 | (3,4,5-tri-Cl)Ph | $C_{15}H_{14}Cl_3N_3O_6$ | 438.65 | — | — |
| 261 | (4-OCH3)Ph | $C_{16}H_{19}N_3O_7$ | 365.34 | — | — |
| 262 | PhNH(CS)NH | $C_{16}H_{18}N_4O_6S$ | 394.40 | — | — |
| 263 | (2,4-di-Br)Ph | $C_{15}H_{15}Br_2N_3O_6$ | 493.11 | — | — |
| 264 | 6-quinolinyl | $C_{18}H_{18}N_4O_6$ | 386.36 | — | — |
| 265 | (3,4,5-tri-OCH3)PhCH2 | $C_{19}H_{25}N_3O_9$ | 439.42 | — | — |
| 266 | (4-CH3)Ph | $C_{16}H_{19}N_3O_6$ | 349.34 | 372(M+Na) | 348(M–H) |
| 267 | (2-F)Ph | $C_{15}H_{16}FN_3O_6$ | 353.31 | — | — |
| 268 | (2-Br-4-Cl-6-F)Ph | $C_{15}H_{14}BrClFN_3O_6$ | 466.65 | — | — |
| 269 | PhCH2 | $C_{16}H_{19}N_3O_6$ | 349.34 | — | 348(M–H) |
| 270 | Ph | $C_{15}H_{17}N_3O_6$ | 335.32 | — | — |
| 271 | (2,6-di-F)Ph | $C_{15}H_{15}F_2N_3O_6$ | 371.30 | — | — |
| 272 | (2,3,4,6-tetra-F)Ph | $C_{15}H_{13}F_4N_3O_6$ | 407.28 | — | — |
| 273 | (2,4-di-Cl)Ph | $C_{15}H_{15}Cl_2N_3O_6$ | 404.21 | — | 402/404(M–H) |
| 274 | (2-CF3)Ph | $C_{16}H_{16}F_3N_3O_6$ | 403.31 | 426(M+Na) | 402(M–H) |
| 275 | 5-indanyl | $C_{18}H_{21}N_3O_6$ | 375.38 | — | — |
| 276 | (3-OPh)Ph | $C_{21}H_{21}N_3O_7$ | 427.41 | — | — |
| 277 | 4-Cl-1-naphthyl | $C_{19}H_{18}ClN_3O_6$ | 419.82 | 458/460(M+K) | 418/420(M–H) |
| 278 | 1,4-benzodioxan-6-yl | $C_{17}H_{19}N_3O_8$ | 393.35 | — | — |
| 279 | (2-Cl)Ph | $C_{15}H_{16}ClN_3O_6$ | 369.76 | — | 368/370(M–H) |
| 280 | (2-Br)Ph | $C_{15}H_{16}BrN_3O_6$ | 414.21 | 414/416(M+H), 434/436(M+Na), 452/454(M+K) | 412/414(M–H), 526/528(M+TFA) |
| 281 | 1-naphthyl | $C_{19}H_{19}N_3O_6$ | 385.38 | — | — |
| 282 | (2-tBu)Ph | $C_{19}H_{25}N_3O_6$ | 391.42 | — | 390(M–H) |
| 283 | (2-tBu-5-NHAc)Ph | $C_{21}H_{28}N_4O_7$ | 448.48 | 449(M+H) | — |
| 284 | 5-isoquinolinyl | $C_{18}H_{18}N_4O_6$ | 386.36 | 387(M+H) | 385(M–H) |
| 285 | 1-indanyl | $C_{18}H_{21}N_3O_6$ | 375.38 | — | — |
| 286 | (2-F)Ph(CH2)2 | $C_{17}H_{20}FN_3O_6$ | 381.36 | — | — |
| 287 | (2,4-di-F)PhCH2 | $C_{16}H_{17}F_2N_3O_6$ | 385.32 | 408(M+Na) | 384(M–H), 498 (M+TFA) |
| 288 | (2,4-di-Cl)PhCH2 | $C_{16}H_{17}Cl_2N_3O_6$ | 418.23 | — | — |
| 289 | PhNNH | $C_{21}H_{22}N_4O_6$ | 426.43 | — | — |
| 290 | PhCONH | $C_{16}H_{18}N_4O_7$ | 378.34 | — | — |
| 291 | PhCH2(Ph)N | $C_{22}H_{24}N_4O_6$ | 440.46 | — | — |

TABLE 12-continued structure: R¹-NH-C(O)-C(O)-NH-CH(CH₃)-C(O)-NH-CH(CH₂CO₂H)-C(O)-H

| Ex. | R¹ | Formula | MW | MS(ES) Pos | MS(ES) neg |
|---|---|---|---|---|---|
| 292 | Ph(Me)N | C₁₆H₂₀N₄O₆ | 364.36 | — | 439 (M–H) |
| 293 | PhSO2 | C₁₅H₁₇N₃O₈S | 399.38 | — | — |
| 294 | PhCH2O | C₁₆H₁₉N₃O₇ | 365.34 | — | — |
| 295 | (2,6-di-Cl)Ph | C₁₅H₁₆Cl₂N₄O₆ | 419.22 | — | — |
| 296 | (4-Me)Ph | C₁₆H₂₀N₄O₆ | 364.36 | — | — |
| 297 | Ph2NCONH | C₂₂H₂₃N₅O₇ | 469.45 | — | — |
| 298 | (4-Cl)Ph | C₁₅H₁₇ClN₄O₆ | 384.78 | 384/386(M+H) | 383/385(M–H) |
| 299 | (4-NO2)PhCONH | C₁₆H₁₇N₅O₉ | 423.34 | — | — |
| 300 | (2,4-di-NO2)PhNH | C₁₅H₁₆N₆O₁₀ | 440.33 | — | — |
| 301 | PhNHCONH | C₁₆H₁₉N₅O₇ | 393.36 | — | — |
| 302 | (2-NO2)PhCONH | C₁₆H₁₇N₅O₉ | 423.34 | — | — |
| 303 | (2,3,4,5,6-penta-F)PhNH | C₁₅H₁₃F₅N₄O₆ | 440.28 | — | — |
| 304 | (4-Br)PhNH | C₁₅H₁₇BrN₄O₆ | 429.23 | — | — |
| 305 | (4-NO2)PHCHN | C₁₆H₁₇N₅O₈ | 407.34 | — | 406(M–H) |
| 306 | PhNH | C₁₅H₁₈N₄O₆ | 350.33 | — | 349(M–H) |
| 307 | (2,3,5,6-tetra-F)PhNH | C₁₅H₁₄F₄N₄O₆ | 422.29 | — | 421(M–H) |
| 308 | (4-F)PhNH | C₁₅H₁₇FN₄O₆ | 368.32 | — | 367(M–H) |
| 309 | (3-Cl-4-Me)PhNH | C₁₆H₁₉ClN₄O₆ | 398.80 | 397/398/399 (M+H) | 397(M–H) |
| 310 | (3-Cl)PhNH | C₁₅H₁₇FN₄O₆ | 368.32 | — | 367(M–H) |
| 311 | 3-[2-ethyl-4(3H)]quinazolinonyl | C₁₉H₂₁N₅O₇ | 431.40 | — | — |
| 312 | (3-Br)PhCONH | C₁₇H₂₁BrN₄O₇ | 473.28 | — | 471 (M–H) |

EXAMPLES 313–318

By the procedures disclosed in Examples 226–312, but starting with the corresponding tertiary amine, the compounds shown below in Table 13 were also prepared:

TABLE 13 structure: (R¹)(R¹')N-C(O)-C(O)-NH-CH(CH₃)-C(O)-NH-CH(CH₂CO₂H)-C(O)-H

| Ex. | (R¹)(R¹')N— | Formula | MW | MS(ES) Pos | MS(ES) neg |
|---|---|---|---|---|---|
| 313 | (1-naphthyl)(Me)N— | C₂₀H₂₁N₃O₆ | 399.40 | — | — |
| 314 | Ph₂N— | C₂₁H₂₁N₃O₆ | 411.41 | — | — |
| 315 | 1-pyrrolidine | C₂₀H₂₁F₄N₃O₇ | 491.13 | — | 509 (M + NH₄) 429 (M + H) |
| 316 | 1-piperidine | C₂₁H₂₃F₄N₃O₇ | 505.15 | 504 (M + H) | — |
| 317 | (1-naphthyl)(Me)N— | C₂₀H₂₁N₃O₆ | 399.40 | — | — |
| 318 | Ph₂N— | C₂₁H₂₁N₃O₆ | 411.41 | — | — |

EXAMPLES 319–394

By the procedures disclosed in Examples 22, but starting with 2-(9H-flouren-9ylmethoxycarbonylamino)-succinic acid 4-tert-butylester and the appropriate alcohol, the compounds shown below in Table 14A were also made:

TABLE 14A

| Ex. | R¹ | R¹' | R² | Formula | MW | MS(ES) |
|---|---|---|---|---|---|---|
| 319 | 5-AcNH-2-tBuPh | H | ethyl | C₂₃H₃₂N₄O₇ | 476.53 | 477(M + H), 499(M + Na) |
| 320 | 2-BrPh | H | ethyl | C₁₁H₂₀BrN₃O₆ | 422.27 | 480/482 (M + K), 464/466 (M + Na), 442/444 (M + H) |
| 321 | 2-BnPh | H | ethyl | C₂₄H₂₇N₃O₆ | 453.49 | 476 (M + Na), 492(M + K) |

By the above procedures, the compounds listed in Table 14B may also be made.

TABLE 14A

| Ex. | R¹ | R¹' | R² |
|---|---|---|---|
| 322 | 2-trifluoromethyl-Ph | H | methyl |
| 323 | 2-BzPh | H | benzyl |

TABLE 14A-continued

| Ex. | R¹ | R¹' | R² |
|---|---|---|---|
| 324 | 2-trifluoromethyl-Ph | H | ethyl |
| 325 | 1-naphthyl | methyl | methyl |
| 326 | 1-naphthyl | methyl | methyl |
| 327 | 2-trifluoromethyl-Ph | H | tBu |
| 328 | methylPh | H | H |
| 329 | PhPh | H | methyl |
| 330 | PhPh | H | ethyl |
| 331 | 3,4-dimethoxyBr | H | methyl |
| 332 | 3,4-dimethoxyBr | H | ethyl |
| 333 | 1-naphthalen-1-yl-ethyl | H | methyl |
| 334 | 1-naphthalen-1-yl-ethyl | H | ethyl |
| 335 | 3,4,5-trimethoxyPh | H | methyl |
| 336 | 3,4,5-trimethoxyPh | H | ethyl |
| 337 | 2-(2-F-Ph)-ethyl | H | methyl |
| 338 | 2-(2-F-Ph)-ethyl | H | ethyl |
| 339 | 1-naphthyl | H | methyl |
| 340 | 1-naphthyl | H | ethyl |
| 341 | 2-methyl Ph | H | H |
| 342 | 2,6-diF-Ph | H | methyl |
| 343 | 2,6-diF-Ph | H | ethyl |
| 344 | 2,6-diF-Ph | H | tBu |
| 345 | 2,6-diF-Ph | H | Bn |
| 346 | Br | H | ethyl |
| 347 | Br | H | methyl |
| 348 | Br | H | tBu |
| 349 | Br | H | Bn |
| 350 | 2,4-diF-Ph | H | tBu |
| 351 | 2-PhPh | H | tBu |
| 352 | 2-BrPh | H | tBu |
| 353 | 1-naphthalen-1-yl-Ph | H | tBu |
| 354 | 2-trifluromethylPh | H | tBu |
| 355 | 3,4,5-trimethoxy-Ph | H | tBu |
| 356 | 3-trifluormethylPh | H | tBu |
| 357 | 2-(2-F-Ph)-ethyl | H | tBu |
| 358 | 1-naphthyl | H | tBu |
| 359 | 2-I-Ph | H | methyl |
| 360 | 2-I-Ph | H | ethyl |
| 361 | 2-I-Ph | H | tBu |
| 362 | 2-I-Ph | H | Bn |
| 363 | 2-Br-Ph | H | methyl |
| 364 | 2-Br-Ph | H | ethyl |
| 365 | 2-Br-Ph | H | tBu |
| 366 | 2-Br-Ph | H | Bn |
| 367 | 1-napthyl | methyl | Bn |
| 368 | 3-trifluoromethylPh | H | Bn |
| 369 | 3-trifluoromethylPh | H | methyl |
| 370 | 3-trifluoromethylPh | H | ethyl |
| 371 | PhCH(Ph) | H | methyl |
| 372 | PhCH(Ph) | H | ethyl |
| 373 | PhCH(Ph) | H | Bn |
| 374 | Ph | Ph | Bn |
| 375 | Ph | Ph | ethyl |
| 376 | Ph | Ph | methyl |
| 377 | 2-BrPh | H | methyl |
| 378 | 2-trifluoromethylPh | H | Bn |
| 379 | 2-tBuPh | H | methyl |
| 380 | 2-Ph-Ph | H | Bn |
| 381 | 3,4-dimethoxyPh | H | Bn |
| 382 | 1-naphthalin-1-yl-ethyl | H | Bn |
| 383 | 3,4,5-trimethoxyPh | H | Bn |
| 384 | 2-(3-F-Ph)-ethyl | H | Bn |
| 385 | 1-naphthyl | H | Bn |
| 386 | 2,4-diF-Br | H | Bn |
| 387 | 2,4-diF-Br | H | tBu |
| 388 | 2,4-diF-Br | H | ethyl |
| 389 | 2,4-diF-Br | H | methyl |
| 390 | Br | H | tBu |
| 391 | 3,4-dimethoxy-Br | H | tBu |
| 392 | 1-naphthyl | methyl | tBu |
| 393 | PhCH(Ph) | H | tBu |
| 394 | Ph | Ph | tBu |

EXAMPLES 395–397

By the procedurees disclosed in Examples 193–200, but starting with (N-9-flourenylmethoxycarbonyl)-tert-butyl glycine, the compounds shown below in Table 15were made:

TABLE 15

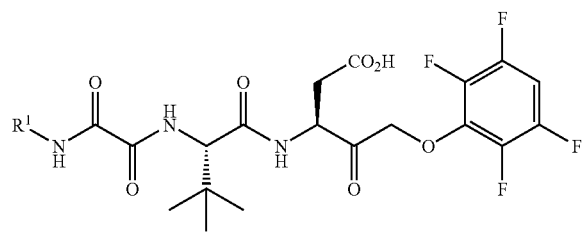

| Ex. | R¹= | Formula | MW | MS(ES) Pos | MS(ES) neg |
|---|---|---|---|---|---|
| 395 | 5-indanyl | $C_{28}H_{29}F_4N_3O_7$ | 595.5466 | — | 594(M + H) |
| 396 | (2,3,5,6-tetra-Cl)Ph | $C_{25}H_{21}Cl_4F_4N_3O_7$ | 693.2624 | — | 690/692/694 (M − H) |
| 397 | (2-Br)Ph | $C_{25}H_{24}BrF_4N_3O_7$ | 634.3781 | — | 632/634(M − H) |

EXAMPLES 398–419

By the procedures disclosed in Examples 5–21, but starting with the appropriate amino acid and oxamic acid, the compounds shown in Table 16 were also made:

TABLE 16

$$R^1-\underset{H}{N}-\underset{O}{\overset{O}{C}}-\underset{O}{\overset{O}{C}}-A-\underset{H}{N}-\underset{\underset{O}{\overset{|}{C}}}{\overset{CO_2R^2}{\overset{|}{C}}}-B$$

| Ex. | R¹ | R² | A | B | Formula | MW | MS(ES) pos | MS(ES) neg |
|---|---|---|---|---|---|---|---|---|
| 398 | (2-tBu)Ph | OtBu | valine | CH₂O(2,3,5,6-tetra-F—Ph) | $C_{23}H_{39}F_4N_3O_7$ | 653.27 | 676(M + Na) | 652(M − H) |
| 399 | (2-tBu)Ph | OCH₃ | valine | CH₂O(2,3,5,6-tetra-F—Ph) | $C_{29}H_{33}F_4N_3O_7$ | 611.58 | 634(M + Na) | 610(M − H) 646(M + Cl—) |
| 400 | 5-quinolin-1-yl | OH | valine | OPOPh₂CH₂ | $C_{35}H_{34}F_3N_3O_{10}P$ | 758.2 | | |
| 401 | (2-Ph)Ph | OH | alpha-methyl-phenylalanine | CH₂O(2,3,5,6-tetra-F—Ph) | $C_{35}H_{29}F_4N_3O_7$ | 679.19 | 702(M + Na) 718(M + JK) | |
| 402 | (2-tBu)Ph | OCH₂Ph | alanine | CH₂O(2,3,5,6-tetra-F—Ph) | $C_{33}H_{33}F_4N_3O_7$ | 659.62 | 660(M + H) | 568(M − H) |
| 403 | (2-Br)Ph | CH₂O(2,3,5,6-tetraF—Ph) | valine | OH | $C_{24}H_{22}BrF_4N_3O_7$ | 619.06 | | 618/620 (M − H) |
| 404 | (2,3,4,5-tetra-F)Ph | CH₂O(2,3,5,6-tetraF—Ph) | valine | OH | $C_{24}H_{19}F_8N_3O_7$ | 613.11 | | 612(M − H) |
| 405 | (2-tBu)Ph | OCH₂Ph | alanine | CH₂O(2,3,5,6-tetra-F-4-Br)Ph | $C_{33}H_{32}BrF_4N_3O_7$ | 737.14 | 737.88/739.8 (M + H) | 735.90/737.90 (M − H) |
| 406 | (2-tBu)Ph | OH | histidine | CH₂O(2,3,5,6-tetra-F—Ph) | $C_{29}H_{29}F_4N_3O_7$ | 635.2 | 636(M + H) | |
| 407 | (2-CF₃)Ph | OCH₂Ph | alanine | CH₂O(2,3,5,6-tetra-F—Ph) | $C_{30}H_{24}F_7N_3O_7$ | 671.15 | 672(M + H) | 670(M − H) |
| 408 | (2-tBu)Ph | OH | Cys(CH₂Ph) | CH₂O(2,3,5,6-tetra-F—Ph) | $C_{33}H_{33}F_4N_3O_8$ | 675.22 | | 674(M − H) |
| 409 | (2-tBu)Ph | OH | Cys | CH₂O(2,3,5,6-tetra-F—Ph) | $C_{26}H_{27}F_4N_4O_7$ | 585.17 | | 584(M − H) |
| 410 | (2-tBu)Ph | OH | tryptophan | CH₂O(2,3,5,6-tetra-F—Ph) | $C_{34}H_{32}F_4N_4O_7$ | 684.22 | | 683(M − H) |
| 411 | (2-tBu)Ph | OH | lysine | CH₂O(2,3,5,6-tetra-F—Ph) | $C_{29}H_{34}F_4N_4O_7$ | 626.24 | | 625(M − H) |
| 412 | 2-(2CH₃O—Ph)Ph | OCH₂Ph | alanine | CH₂O(2,3,5,6-tetra-F—Ph) | $C_{36}H_{31}F_4N_3O_8$ | 709.2 | | |
| 413 | piperidin-1-yl | OCH₂Ph | alanine | CH₂O(2,3,5,6-tetra-F—Ph) | $C_{28}H_{30}F_4N_4O_7$ | 610.21 | 611(M + H) | |
| 414 | pyrrolidin-1-yl | OCH₂Ph | alanine | CH₂O(2,3,5,6-tetra-F—Ph) | $C_{24}H_{30}F_4N_4O_7$ | 596.19 | 597.28 (M + H) | |
| 415 | Cbz | OH | valine | CH₂O(2,3,5,6-tetra-F—Ph) | $C_{26}H_{25}F_4N_3O_9$ | 599.15 | 622(M + Na) | 598(M − H) |
| 416 | 5-indanyl | OH | (t-butyl) glycine | CH₂O(2,3,5,6-tetra-F—Ph) | $C_{28}H_{29}F_4N_3O_7$ | 595.55 | — | 594(M − H) |
| 417 | (2,3,5,6-tetra-Cl)Ph | OH | (t-butyl) glycine | CH₂O(2,3,5,6-tetra-F—Ph) | $C_{25}H_{21}Cl_4F_4N_3O_7$ | 693.26 | — | 690/692/694 (M − H) |
| 418 | (z-Br)Ph | OH | (t-butyl) glycine | CH₂O(2,3,5,6-tetra-F—Ph) | $C_{25}H_{24}BrF_4N_3O_7$ | 634.38 | — | 632/634 (M − H) |
| 419 | 2-(2-CH₃Oph)Ph | OCH₂Ph | alanine | CH₂O(2,3,5,6-tetra-F—Ph) | $C_{36}H_{31}F_4N_3O_8$ | 709.2 | 710(M + H) | 708(M − H) |

EXAMPLES 420–426

By the procedures disclosed in Example 126, but starting with intermediates having the desired stereochemistry, the compounds shown in Table 17 were also made:

TABLE 17

| Ex. | $R^2$ | Ala stereochemistry | Asp stereochemistry | Formula | MW | MS(ES) pos | MS(ES) neg |
|---|---|---|---|---|---|---|---|
| 420 | OBn | R | R | $C_{33}H_{33}F_4N_3O_7$ | 659.62 | 660(M + H) | 658(M − H) |
| 421 | OBn | R | S | $C_{33}H_{33}F_4N_3O_7$ | 659.62 | 660(M + H) | 658(M − H) |
| 422 | OBn | S | R | $C_{33}H_{33}F_4N_3O_7$ | 659.62 | 660(M + H) | 658(M − H) |
| 423 | H | S | S | $C_{35}H_{29}F_4N_3O_7$ | 569.5 | 570(M + H) | 568(M − H) |
| 424 | H | R | R | $C_{33}H_{33}F_4N_3O_7$ | 569.5 | 570(M + H) | 568(M − H) |
| 425 | H | R | S | $C_{24}H_{22}BrF_4N_3O_7$ | 569.5 | 570(M + H) | 568(M − H) |
| 426 | H | S | R | $C_{24}H_{19}F_8N_3O_7$ | 569.5 | 570(M + H) | 568(M − H) |

Although the invention has been described with reference to the examples provided above, it should be understood that various modifications can be made without departing from the spirit of the invention. Accordingly, the invention is limited only by the claims.

We claim:

1. A method for treating hepatitis, comprising administering an effective amount of a pharmaceutical composition to a patient in need thereof, wherein the pharmaceutical composition comprises a pharmaceutically acceptable carrier and a compound of the following formula:

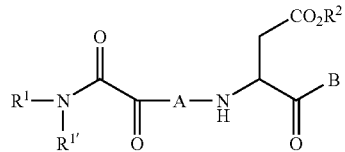

Formula I wherein:

A is a natural or unnatural amino acid of Formula IIa–i:

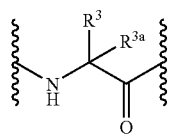

IIa

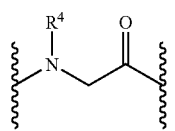

IIb

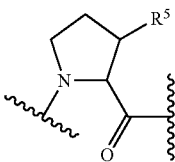

IIc

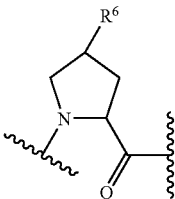

IId

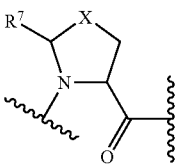

IIe

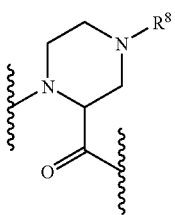

IIf

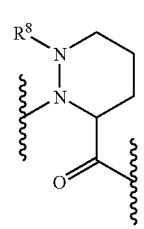

IIg

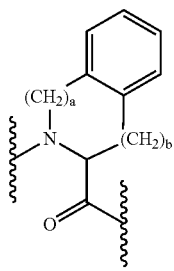

IIh

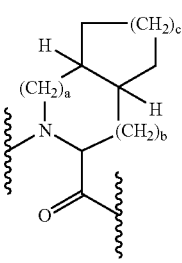

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, —$(CH_2)_n$cycloalkyl, —$(CH_2)_n$phenyl, —$(CH_2)_n$(substituted phenyl), —$(CH_2)_n$(1 or 2-naphthyl), —$(CH_2)_n$(substituted 1 or 2-naphthyl), —$(CH_2)_n$(heteroaryl), —$(CH_2)_n$(substituted heteroaryl), halomethyl, —$CO_2R^{12}$, —$CONR^{13}R^{14}$, —$CH_2ZR^{15}$, —$CH_2OCO$(aryl), —$CH_2OCO$(heteroaryl), —$CH_2OCO$(substituted heteroaryl), or —$CH_2OPO(R^{16})R^{17}$, where Z is an oxygen or a sulfur atom, or B is a group of the Formula IIIa–c:

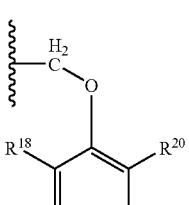

IIIa

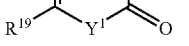

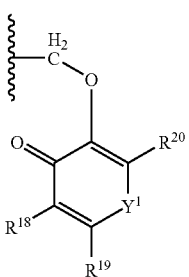

IIIb

IIIc

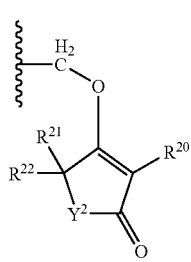

R¹ is alkyl, cycloalkyl, substituted cycloalkyl, (cycloalkyl)alkyl, (substituted cycloalkyl)alkyl, phenyl, substituted phenyl, phenylalkyl, (substituted phenyl)alkyl, naphthyl, substituted naphthyl, (1- or 2-naphthyl)alkyl, (substituted 1- or 2-naphthyl)alkyl, heterocycle, substituted heterocycle, (heterocycle)alkyl, (substituted heterocycle)alkyl, —NR$^{1a}$(R$^{1b}$), or —OR$^{1c}$;

R$^{1'}$ is hydrogen, alkyl, phenyl, substituted phenyl, naphthyl, substituted naphthyl, heterocycle or substituted heterocycle;

or R¹ and R$^{1'}$ taken together with the nitrogen atom to which they are attached form a heterocycle or substituted heterocycle;

R² is hydrogen, lower alkyl, cycloalkyl, (cycloalkyl)alkyl, phenyl, substituted phenyl, phenylalkyl, (substituted phenyl)alkyl, naphthyl, substituted naphthyl, (1- or 2-naphthyl)alkyl, or (substituted 1 or 2 naphthyl)alkyl;

and wherein:

R$^{1a}$ and R$^{1b}$ are independently hydrogen, alkyl, cycloalkyl, (cycloalkyl)alkyl, phenyl, substituted phenyl, phenylalkyl, (substituted phenyl)alkyl, naphthyl, substituted naphthyl, (1- or 2-naphthyl)alkyl, (substituted 1 or 2 naphthyl)alkyl, heteroaryl, substituted heteroaryl, (heteroaryl)alkyl, or (substituted heteroaryl)alkyl, with the proviso that R$^{1a}$ and R$^{1b}$ cannot both be hydrogen;

R$^{1c}$ is alkyl, cycloalkyl, (cycloalkyl)alkyl, phenyl, substituted phenyl, phenylalkyl, (substituted phenyl)alkyl, naphthyl, substituted naphthyl, (1 or 2 naphthyl)alkyl, (substituted 1- or 2-naphthyl)alkyl, heteroaryl, substituted heteroaryl, (heteroaryl)alkyl, or (substituted heteroaryl)alkyl;

R³ is lower alkyl, cycloalkyl, phenyl, substituted phenyl, —(CH$_2$)$_n$NH$_2$, —(CH$_2$)$_n$NHCOR$^9$, —(CH$_2$)$_n$N(C═NH)NH$_2$, —(CH$_2$)$_m$CO$_2$R², —(CH$_2$)$_m$OR$^{10}$, —(CH$_2$)$_m$SR$^{11}$, —(CH$_2$)$_n$cycloalkyl, —(CH$_2$)$_n$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{3a}$ is hydrogen or methyl, or R³ and R$^{3a}$, taken together are —(CH$_2$)$_d$—where d is an interger from 2 to 6;

R⁴ is phenyl, substituted phenyl, —(CH$_2$)$_m$phenyl, —(CH$_2$)$_m$(substituted phenyl), cycloalkyl, or benzofused cycloalkyl;

R⁵ is hydrogen, lower alkyl, cycloalkyl, phenyl, substituted phenyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R⁶ is hydrogen, fluorine, oxo, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), —OR$^{10}$, —SR$^{11}$, or —NHCOR$^9$;

R⁷ is hydrogen, oxo, lower alkyl, cycloalkyl, phenyl, substituted phenyl, naphthyl, —(CH$_2$)$_n$cycloalkyl, —(CH$_2$)$_n$phenyl, (CH$_2$)$_n$(substituted phenyl), or —(CH$_2$)$_n$(1- or 2-naphthyl);

R⁸ is lower alkyl, cycloalkyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), or —COR$^9$;

R⁹ is hydrogen, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), —OR$^{12}$, or —NR$^{13}$R$^{14}$;

R$^{10}$ is hydrogen, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{11}$ is lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{12}$ is lower alkyl, cycloalkyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{13}$ is hydrogen, lower alkyl, cycloalkyl, phenyl, substituted phenyl, naphthyl, substituted naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{14}$ is hydrogen or lower alkyl;

or R$^{13}$ and R$^{14}$ taken together form a five to seven membered carbocyclic or heterocyclic ring;

R$^{15}$ is phenyl, substituted phenyl, naphthyl, substituted naphthyl, heteroaryl, substituted heteroaryl, —(CH$_2$)$_n$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{16}$ and R$^{17}$ are independently lower alkyl, cycloalkyl, phenyl, substituted phenyl, naphthyl, phenylalkyl, (substituted phenyl)alkyl, or (cycloalkyl)alkyl;

R$^{18}$ and R$^{19}$ are independently hydrogen, alkyl, phenyl, substituted phenyl, —(CH$_2$)$_n$phenyl, —(CH$_2$)$_n$(substituted phenyl), or R$^{18}$ and R$^{19}$ taken together are —(CH═CH)$_2$—;

R$^{20}$ is hydrogen, alkyl, phenyl, substituted phenyl, —(CH$_2$)$_n$phenyl, or —(CH$_2$)$_n$(substituted phenyl);

R$^{21}$, R$^{22}$ and R$^{23}$ are independently hydrogen or alkyl;

X is —CH$_2$—, —(CH$_2$)$_2$—, —(CH$_2$)$_3$—, or —S—;

Y¹ is —O— or —N(R$^{23}$)—;

Y² is —CH$_2$—, —O—, or —N(R$^{23}$)—;

a is 0 or 1;

b is 1 or 2, provided that when a is 1 then b is 1;

c is 1 or 2, provided that when c is 1 then a is 0 and b is 1;

m is 1 or 2; and n is 1, 2, 3 or 4, or a pharmaceutically acceptable salt thereof.

2. A method for treating hepatitis, comprising administering an effective amount of a pharmaceutical composition to a patient in need thereof, wherein the pharmaceutical composition comprises a pharmaceutically acceptable carrier and a compound of the following formula:

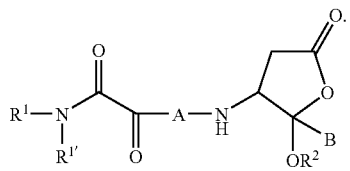

wherein:

A is a natural or unnatural amino acid of Formula IIa–i:

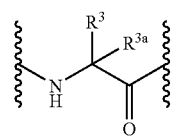　IIa

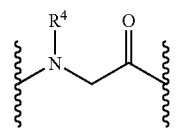　IIb

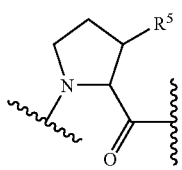　IIc

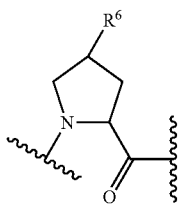　IId

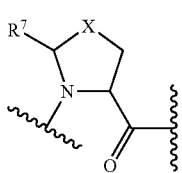　IIe

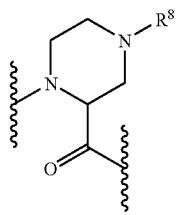　IIf

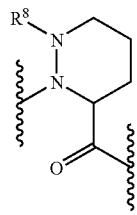　IIg

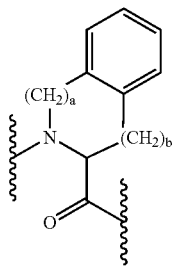　IIh

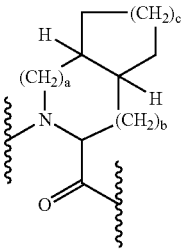　IIi

B is a hydrogen atom, a deuterium atom, alkyl, cycloalkyl, phenyl, substituted phenyl, naphthyl, substituted naphthyl, 2-benzoxazolyl, substituted 2-oxazolyl, —$(CH_2)_n$cycloalkyl, —$(CH_2)_n$phenyl, —$(CH_2)_n$(substituted phenyl), —$(CH_2)_n$(1 or 2-naphthyl), —$(CH_2)_n$(substituted 1 or 2-naphthyl), —$(CH_2)_n$(heteroaryl), —$(CH_2)_n$(substituted heteroaryl), halomethyl, —$CO_2R^{12}$, —$CONR^{13}R^{14}$, —$CH_2ZR^{15}$, —$CH_2OCO$(aryl), —$CH_2OCO$(heteroaryl), —$CH_2OCO$(substituted heteroaryl), or —$CH_2OPO(R^{16})R^{17}$, where Z is an oxygen or a sulfur atom, or B is a group of the Formula IIIa–c:

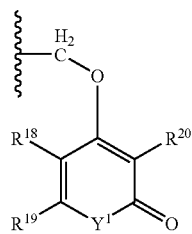　IIIa

-continued

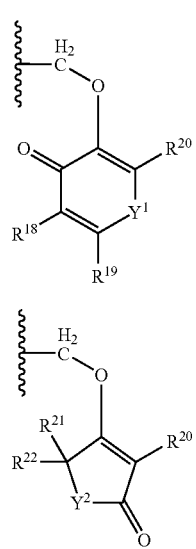

IIIb

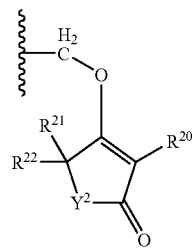

IIIc

R¹ is alkyl, cycloalkyl, substituted cycloalkyl, (cycloalkyl)alkyl, (substituted cycloalkyl)alkyl, phenyl, substituted phenyl, phenylalkyl, (substituted phenyl)alkyl, naphthyl, substituted naphthyl, (1-or 2-naphthyl)alkyl, (substituted 1-or 2-naphthyl)alkyl, heterocycle, substituted heterocycle, (heterocycle)alkyl, (substituted heterocycle)alkyl, —NR$^{1a}$(R$^{1b}$), or —OR$^{1c}$;

R$^{1'}$ is hydrogen, alkyl, phenyl, substituted phenyl, naphthyl, substituted naphthyl, heterocycle or substituted heterocycle;

or R¹ and R$^{1'}$ taken together with the nitrogen atom to which they are attached form a heterocycle or substituted heterocycle;

R² is hydrogen, lower alkyl, cycloalkyl, (cycloalkyl)alkyl, phenyl, substituted phenyl, phenylalkyl, (substituted phenyl)alkyl, naphthyl, substituted naphthyl, (1-or 2-naphthyl)alkyl, or (substituted 1 or 2 naphthyl)alkyl;

and wherein:

R$^{1a}$ and R$^{1b}$ are independently hydrogen, alkyl, cycloalkyl, (cycloalkyl)alkyl, phenyl, substituted phenyl, phenylalkyl, (substituted phenyl)alkyl, naphthyl, substituted naphthyl, (1-or 2-naphthyl)alkyl, (substituted 1 or 2 naphthyl)alkyl, heteroaryl, substituted heteroaryl, (heteroaryl)alkyl, or (substituted heteroaryl)alkyl, with the proviso that R$^{1a}$ and R$^{1b}$ cannot both be hydrogen;

R$^{1c}$ is alkyl, cycloalkyl, (cycloalkyl)alkyl, phenyl, substituted phenyl, phenylalkyl, (substituted phenyl)alkyl, naphthyl, substituted naphthyl, (1 or 2 naphthyl)alkyl, (substituted 1-or 2-naphthyl)alkyl, heteroaryl, substituted heteroaryl, (heteroaryl)alkyl, or (substituted heteroaryl)alkyl;

R³ is lower alkyl, cycloalkyl, phenyl, substituted phenyl, —(CH$_2$)$_n$NH$_2$, —(CH$_2$)$_n$NHCOR⁹, —(CH$_2$)$_n$N(C═NH)NH$_2$, —(CH$_2$)$_m$CO$_2$R², —(CH$_2$)$_m$OR$^{10}$, —(CH$_2$)$_m$SR$^{11}$, —(CH$_2$)$_m$cycloalkyl, —(CH$_2$)$_m$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{3a}$ is hydrogen or methyl, or R³ and R$^{3a}$, taken together are —(CH$_2$)$_d$—where d is an integer from 2 to 6;

R⁴ is phenyl, substituted phenyl, —(CH$_2$)$_m$phenyl, —(CH$_2$)$_m$(substituted phenyl), cycloalkyl, or benzofused cycloalkyl;

R⁵ is hydrogen, lower alkyl, cycloalkyl, phenyl, substituted phenyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R⁶ is hydrogen, fluorine, oxo, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), —OR$^{10}$, —SR$^{11}$, or —NHCOR⁹;

R⁷ is hydrogen, oxo, lower alkyl, cycloalkyl, phenyl, substituted phenyl, naphthyl, —(CH$_2$)$_n$cycloalkyl, —(CH$_2$)$_n$phenyl, (CH$_2$)$_n$(substituted phenyl), or —(CH$_2$)$_n$(1- or 2-naphthyl);

R⁸ is lower alkyl, cycloalkyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), or —COR⁹;

R⁹ is hydrogen, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), —(CH$_2$)$_n$(1- or 2-naphthyl), —OR$^{12}$, or —NR$^{13}$R$^{14}$;

R$^{10}$ is hydrogen, lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{11}$ is lower alkyl, cycloalkyl, phenyl, substituted phenyl, naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{12}$ is lower alkyl, cycloalkyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{13}$ is hydrogen, lower alkyl, cycloalkyl, phenyl, substituted phenyl, naphthyl, substituted naphthyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R$^{14}$ is hydrogen or lower alkyl;

or R$^{13}$ and R$^{14}$ taken together form a five to seven membered carbocyclic or heterocyclic ring;

R$^{15}$ is phenyl, substituted phenyl, naphthyl, substituted naphthyl, heteroaryl, substituted heteroaryl, —(CH$_2$)$_n$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{16}$ and R$^{17}$ are independently lower alkyl, cycloalkyl, phenyl, substituted phenyl, naphthyl, phenylalkyl, (substituted phenyl)alkyl, or (cycloalkyl)alkyl;

R$^{18}$ and R$^{19}$ are independently hydrogen, alkyl, phenyl, substituted phenyl, —(CH$_2$)$_n$phenyl, —(CH$_2$)$_n$(substituted phenyl), or R$^{18}$ and R$^{19}$ taken together are —(CH═CH)$_2$—;

R$^{20}$ is hydrogen, alkyl, phenyl, substituted phenyl, —(CH$_2$)$_n$phenyl, or —(CH$_2$)$_n$(substituted phenyl);

R$^{21}$, R$^{22}$ and R$^{23}$ are independently hydrogen or alkyl;

X is —CH$_2$—, —(CH$_2$)$_2$—, —(CH$_2$)$_3$—, or —S—;

Y¹ is —O— or —N(R$^{23}$)—;

Y² is —CH$_2$—, —O—, or —N(R$^{23}$)—;

a is 0 or 1;

b is 1 or 2, provided that when a is 1 then b is 1;

c is 1 or 2, provided that when c is 1 then a is 0 and b is 1;

m is 1 or 2; and n is 1, 2, 3 or 4, or a pharmaceutically acceptable salt thereof.

3. The method of claim 1 wherein:
$R^1$ is substituted phenyl;
$R^{1'}$ is hydrogen;
$R^2$ is hydrogen or lower alkyl;
B is hydrogen or —$CH_2ZR^{15}$ where Z is oxygen and $R^{15}$ is substituted phenyl;
A is a natural or unnatural amino acid of Formula IIa:

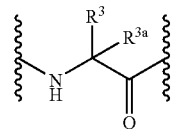

IIa $R^3$ is lower alkyl; and
$R^{3a}$ is hydrogen.

4. The method of claim 3 wherein $R^1$ is phenyl substituted with one or more alkyl groups.

5. The method of claim 4 wherein $R^1$ is 2-tert-butyl-phenyl.

6. The method of claim 3 wherein $R^1$ is phenyl substituted with one or more halogen atoms.

7. The method of claim 6 wherein $R^1$ is 2-fluorophenyl.

8. The method of claim 6 wherein $R^1$ is 2-bromo-4-chloro-6-fluoro-phenyl.

9. The method of claim 3 wherein $R^1$ is 2-trifluoromethylphenyl.

10. The method of claim 3 wherein $R^1$ is 3-trifluoromethylphenyl.

11. The method of claim 3 wherein $R^2$ is hydrogen.

12. The method of claim 3 wherein $R^2$ is lower alkyl.

13. The method of claim 12 wherein $R^2$ is ethyl.

14. The method of claim 12 wherein $R^3$ is methyl.

15. The method of claim 3 wherein B is hydrogen.

16. The method of claim 3 wherein B is —$CH_2ZR^{15}$ and $R^{15}$ is phenyl substituted with one or more halogen atoms.

17. The method of claim 16 wherein $R^{15}$ is 2,6-dihalophenyl, 2,4,6-trihalophenyl, or 2,3,5,6-tetrahalophenyl.

18. The method of claim 17 wherein $R^{15}$ is 2,3,5,6-tetrafluorophenyl.

19. The method of claim 3 wherein $R^1$ is 2-bromo-4-chloro-6-fluoro-phenyl, $R^3$ is methyl, B is hydrogen.

20. The method of claim 19 wherein the compound is (3S)-3-[N-(N'-(2-bromo-4-chloro-6-fluoro-phenyl)Oxamyl)Alaninyl]Amino-4-Oxobutanoic Acid.

21. The method of claim 3 wherein the compound is (3S)-3-[N-(N'-(2-tert-Butylphenyl)Oxamyl)Alaninyl] Amino-5-(2',3',5',6'-Tetrafluorophenoxy)-4-Oxopentanoic Acid.

22. The method of claim 3 wherein the compound is (3S)-3-[N-(N'-(2-Trifluoromethylphenyl)Oxamyl)Alaninyl] Amino-5-(2',3',5',6'-Tetrafluorophenoxy)-4-Oxopentanoic Acid.

23. The method of claim 1 wherein B is —$CH_2ZR^{15}$ wherein Z is oxygen.

24. The method of claim 23 wherein $R^{15}$ is heteroaryl or substituted heteroaryl.

25. The method of claim 24 wherein $R^{15}$ is pyrimidyl or substituted pyrimidyl.

26. The method of claim 25 wherein $R^{15}$ is pyrimidyl substituted with trifluoromethyl.

27. A method of prolonging the viability of an organ that has been removed from a donor or isolated cells derived from an organ for the purpose of a future transplantation procedure, comprising applying an effective amount of a pharmaceutical composition to the organ or isolated cells to prolong the viability of the same as compared to untreated organ or isolated cells, wherein the pharmaceutical composition comprises a pharmaceutically acceptable carrier and a compound of the following formula:

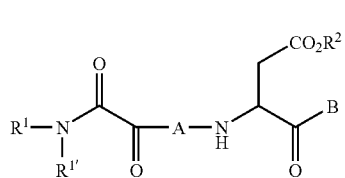

Formula I wherein:
A is a natural or unnatural amino acid of Formula IIa–i:

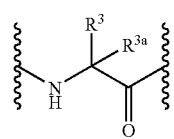

IIa

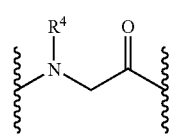

IIb

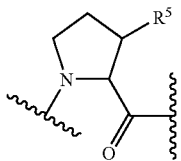

IIc

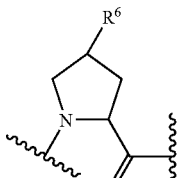

IId

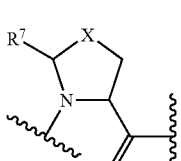

IIe

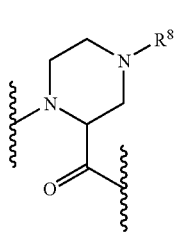

IIf

-continued

IIg

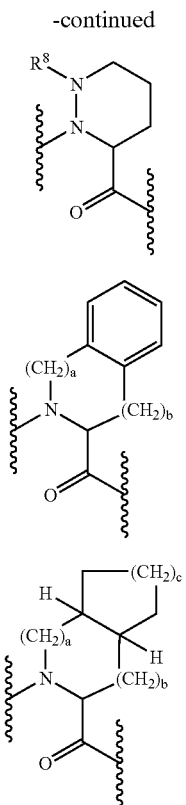

IIh

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, —(CH$_2$)$_n$cycloalkyl, —(CH$_2$)$_n$phenyl, —(CH$_2$)$_n$(substituted phenyl), —(CH$_2$)$_n$(1 or 2-naphthyl), —(CH$_2$)$_n$(substituted 1 or 2-naphthyl), —(CH$_2$)$_n$(heteroaryl), —(CH$_2$)$_n$(substituted heteroaryl), halomethyl, —CO$_2$R$^{12}$, —CONR$^{13}$R$^{14}$, —CH$_2$ZR$^{15}$, —CH$_2$OCO(aryl), —CH$_2$OCO(heteroaryl), —CH$_2$OCO(substituted heteroaryl), or —CH$_2$OPO(R$^{16}$)R$^{17}$, where Z is an oxygen or a sulfur atom, or B is a group of the Formula IIIa–c:

IIIa

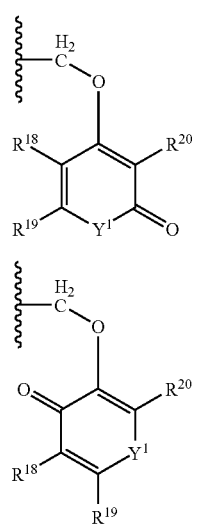

IIIb

-continued

IIIc

R$^1$ is alkyl, cycloalkyl, substituted cycloalkyl, (cycloalkyl)alkyl, (substituted cycloalkyl)alkyl, phenyl, substituted phenyl, phenylalkyl, (substituted phenyl)alkyl, naphthyl, substituted naphthyl, (1- or 2-naphthyl)alkyl, (substituted 1- or 2-naphthyl)alkyl, heterocycle, substituted heterocycle, (heterocycle)alkyl, (substituted heterocycle)alkyl, —NR$^{1a}$(R$^{1b}$), or —OR$^{1c}$;

R$^{1'}$ is hydrogen, alkyl, phenyl, substituted phenyl, naphthyl, substituted naphthyl, heterocycle or substituted heterocycle;

or R$^1$ and R$^{1'}$ taken together with the nitrogen atom to which they are attached form a heterocycle or substituted heterocycle;

R$^2$ is hydrogen, lower alkyl, cycloalkyl, (cycloalkyl)alkyl, phenyl, substituted phenyl, phenylalkyl, (substituted phenyl)alkyl, naphthyl, substituted naphthyl, (1- or 2-naphthyl)alkyl, or (substituted 1 or 2 naphthyl)alkyl;

and wherein:

R$^{1a}$ and R$^{1b}$ are independently hydrogen, alkyl, cycloalkyl, (cycloalkyl)alkyl, phenyl, substituted phenyl, phenylalkyl, (substituted phenyl)alkyl, naphthyl, substituted naphthyl, (1- or 2-naphthyl)alkyl, (substituted 1 or 2 naphthyl)alkyl, heteroaryl, substituted heteroaryl, (heteroaryl)alkyl, or (substituted heteroaryl) alkyl, with the proviso that R$^{1a}$ and R$^{1b}$ cannot both be hydrogen;

R$^{1c}$ is alkyl, cycloalkyl, (cycloalkyl)alkyl, phenyl, substituted phenyl, phenylalkyl, (substituted phenyl)alkyl, naphthyl, substituted naphthyl, (1 or 2 naphthyl)alkyl, (substituted 1- or 2-naphthyl)alkyl, heteroaryl, substituted heteroaryl, (heteroaryl)alkyl, or (substituted heteroaryl)alkyl;

R$^3$ is lower alkyl, cycloalkyl, phenyl, substituted phenyl, —(CH$_2$)$_n$NH$_2$, —(CH$_2$)$_n$NHCOR$^9$, —(CH$_2$)$_n$N(C=NH)NH$_2$, —(CH$_2$)$_m$CO$_2$R$^2$, —(CH$_2$)$_m$OR$^{10}$, —(CH$_2$)$_m$SR$^{11}$, —(CH$_2$)$_n$cycloalkyl, —(CH$_2$)$_n$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{3a}$ is hydrogen or methyl, or R$^3$ and R$^{3a}$, taken together are —(CH$_2$)$_d$—where d is an interger from 2 to 6;

R$^4$ is phenyl, substituted phenyl, —(CH$_2$)$_m$phenyl, —(CH$_2$)$_m$(substituted phenyl), cycloalkyl, or benzofused cycloalkyl;

R$^5$ is hydrogen, lower alkyl, cycloalkyl, phenyl, substituted phenyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

R⁶ is hydrogen, fluorine, oxo, lower alkyl, cycloalkyl, phenyl, substituted phenyl, naphthyl, —(CH₂)ₙcycloalkyl, —(CH₂)ₙphenyl, —(CH₂)ₙ(substituted phenyl), —(CH₂)ₙ(1- or 2-naphthyl), —OR¹⁰, —SR¹¹, or —NHCOR⁹;

R⁷ is hydrogen, oxo, lower alkyl, cycloalkyl, phenyl, substituted phenyl, naphthyl, —(CH₂)ₙcycloalkyl, —(CH₂)ₙphenyl, (CH₂)ₙ(substituted phenyl), or —(CH₂)ₙ(1- or 2-naphthyl);

R⁸ is lower alkyl, cycloalkyl, —(CH₂)ₙcycloalkyl, —(CH₂)ₙphenyl, —(CH₂)ₙ(substituted phenyl), —(CH₂)ₙ(1- or 2-naphthyl), or —COR⁹;

R⁹ is hydrogen, lower alkyl, cycloalkyl, phenyl, substituted phenyl, naphthyl, —(CH₂)ₙcycloalkyl, —(CH₂)ₙphenyl, —(CH₂)ₙ(substituted phenyl), —(CH₂)ₙ(1- or 2-naphthyl), —OR¹², or —NR¹³R¹⁴;

R¹⁰ is hydrogen, lower alkyl, cycloalkyl, phenyl, substituted phenyl, naphthyl, —(CH₂)ₙcycloalkyl, —(CH₂)ₙphenyl, —(CH₂)ₙ(substituted phenyl), or —(CH₂)ₙ(1- or 2-naphthyl);

R¹¹ is lower alkyl, cycloalkyl, phenyl, substituted phenyl, naphthyl, —(CH₂)ₙcycloalkyl, —(CH₂)ₙphenyl, —(CH₂)ₙ(substituted phenyl), or —(CH₂)ₙ(1- or 2-naphthyl);

R¹² is lower alkyl, cycloalkyl, —(CH₂)ₙcycloalkyl, —(CH₂)ₙphenyl, —(CH₂)ₙ(substituted phenyl), or —(CH₂)ₙ(1- or 2-naphthyl);

R¹³ is hydrogen, lower alkyl, cycloalkyl, phenyl, substituted phenyl, naphthyl, substituted naphthyl, —(CH₂)ₙcycloalkyl, —(CH₂)ₙphenyl, —(CH₂)ₙ(substituted phenyl), or —(CH₂)ₙ(1- or 2-naphthyl);

R¹⁴ is hydrogen or lower alkyl;

or R¹³ and R¹⁴ taken together form a five to seven membered carbocyclic or heterocyclic ring;

R¹⁵ is phenyl, substituted phenyl, naphthyl, substituted naphthyl, heteroaryl, substituted heteroaryl, —(CH₂)ₙphenyl, —(CH₂)ₙ(substituted phenyl), —(CH₂)ₙ(1- or 2-naphthyl), —(CH₂)ₙ(heteroaryl), or —(CH₂)ₙ(substituted heteroaryl);

R¹⁶ and R¹⁷ are independently lower alkyl, cycloalkyl, phenyl, substituted phenyl, naphthyl, phenylalkyl, (substituted phenyl)alkyl, or (cycloalkyl)alkyl;

R¹⁸ and R¹⁹ are independently hydrogen, alkyl, phenyl, substituted phenyl, —(CH₂)ₙphenyl, —(CH₂)ₙ(substituted phenyl), or R¹⁸ and R¹⁹ taken together are —(CH=CH)₂—;

R²⁰ is hydrogen, alkyl, phenyl, substituted phenyl, —(CH₂)ₙphenyl, or —(CH₂)ₙ(substituted phenyl);

R²¹, R²² and R²³ are independently hydrogen or alkyl;

X is —CH₂—, —(CH₂)₂—, —(CH₂)₃—, or —S—;

Y¹ is —O— or —N(R²³)—;

Y² is —CH₂—, —O—, or —N(R²³)—;

a is 0 or 1;

b is 1 or 2, provided that when a is 1 then b is 1;

c is 1 or 2, provided that when c is 1 then a is 0 and b is 1;

m is 1 or 2; and n is 1, 2, 3 or 4, or a pharmaceutically acceptable salt thereof.

28. The method of claim 27 wherein the organ is an intact organ.

29. The method of claim 27 wherein the isolated cells are pancreatic islet cells, dopaminergic neurons, blood cells, or hematopoietic cells.

30. A method of prolonging the viability of an organ that has been removed from a donor or isolated cells derived from an organ for the purpose of a future transplantation procedure, comprising applying an effective amount of a pharmaceutical composition to the organ or isolated cells to prolong the viability of the same as compared to untreated organ or isolated cells, wherein the pharmaceutical composition comprises a pharmaceutically acceptable carrier and a compound of the following formula:

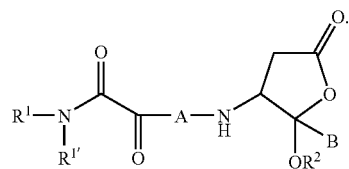

wherein:

A is a natural or unnatural amino acid of Formula IIa–i:

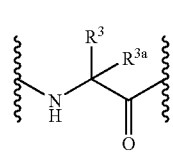

IIa

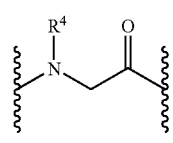

IIb

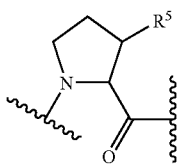

IIc

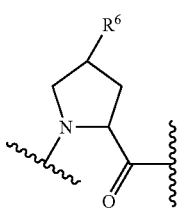

IId

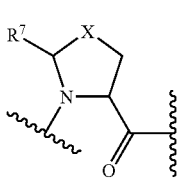

IIe

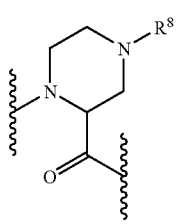

IIf

-continued

IIg

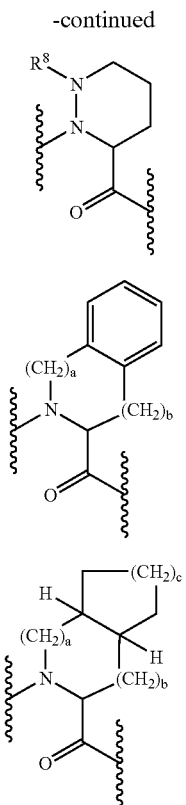

IIh

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, —(CH$_2$)$_n$cycloalkyl, —(CH$_2$)$_n$phenyl, —(CH$_2$)$_n$(substituted phenyl), —(CH$_2$)$_n$(1 or 2-naphthyl), —(CH$_2$)$_n$(substituted 1 or 2-naphthyl), —(CH$_2$)$_n$(heteroaryl), —(CH$_2$)$_n$(substituted heteroaryl), halomethyl, —CO$_2$R$^{12}$, —CONR$^{13}$R$^{14}$, —CH$_2$ZR$^{15}$, —CH$_2$OCO(aryl), —CH$_2$OCO(heteroaryl), —CH$_2$OCO(substituted heteroaryl), or —CH$_2$OPO(R$^{16}$)R$^{17}$, where Z is an oxygen or a sulfur atom, or B is a group of the Formula IIIa–c:

IIIa

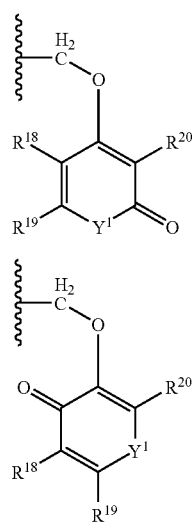

IIIb

-continued

IIIc

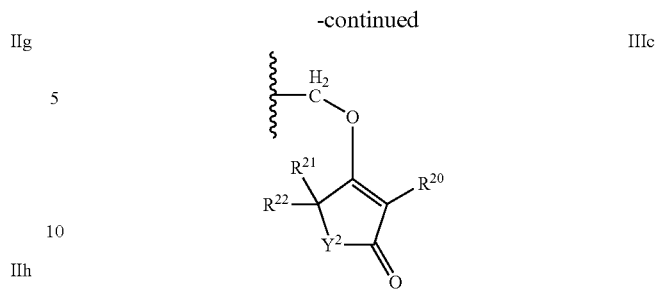

R$^1$ is alkyl, cycloalkyl, substituted cycloalkyl, (cycloalkyl)alkyl, (substituted cycloalkyl)alkyl, phenyl, substituted phenyl, phenylalkyl, (substituted phenyl)alkyl, naphthyl, substituted naphthyl, (1-or 2-naphthyl)alkyl, (substituted 1-or 2-naphthyl)alkyl, heterocycle, substituted heterocycle, (heterocycle)alkyl, (substituted heterocycle)alkyl, —NR$^{1a}$(R$^{1b}$), or —OR$^{1c}$;

R$^{1'}$ is hydrogen, alkyl, phenyl, substituted phenyl, naphthyl, substituted naphthyl, heterocycle or substituted heterocycle;

or R$^1$ and R$^{1'}$ taken together with the nitrogen atom to which they are attached form a heterocycle or substituted heterocycle;

R$^2$ is hydrogen, lower alkyl, cycloalkyl, (cycloalkyl)alkyl, phenyl, substituted phenyl, phenylalkyl, (substituted phenyl)alkyl, naphthyl, substituted naphthyl, (1-or 2-naphthyl)alkyl, or (substituted 1 or 2 naphthyl)alkyl;

and wherein:

R$^{1a}$ and R$^{1b}$ are independently hydrogen, alkyl, cycloalkyl, (cycloalkyl)alkyl, phenyl, substituted phenyl, phenylalkyl, (substituted phenyl)alkyl, naphthyl, substituted naphthyl, (1-or 2-naphthyl)alkyl, (substituted 1 or 2 naphthyl)alkyl, heteroaryl, substituted heteroaryl, (heteroaryl)alkyl, or (substituted heteroaryl)alkyl, with the proviso that R$^{1a}$ and R$^{1b}$ cannot both be hydrogen;

R$^{1c}$ is alkyl, cycloalkyl, (cycloalkyl)alkyl, phenyl, substituted phenyl, phenylalkyl, (substituted phenyl)alkyl, naphthyl, substituted naphthyl, (1 or 2 naphthyl)alkyl, (substituted 1-or 2-naphthyl)alkyl, heteroaryl, substituted heteroaryl, (heteroaryl)alkyl, or (substituted heteroaryl)alkyl;

R$^3$ is lower alkyl, cycloalkyl, phenyl, substituted phenyl, —(CH$_2$)$_n$NH$_2$, —(CH$_2$)$_n$NHCOR$^9$, —(CH$_2$)$_n$N(C=NH)NH$_2$, —(CH$_2$)$_m$CO$_2$R$^2$, —(CH$_2$)$_m$OR$^{10}$, —(CH$_2$)$_m$SR$^{11}$, —(CH$_2$)$_n$cycloalkyl, —(CH$_2$)$_n$phenyl, —(CH$_2$)$_n$(substituted phenyl), —(CH$_2$)$_n$(1- or 2-naphthyl), —(CH$_2$)$_n$(heteroaryl), or —(CH$_2$)$_n$(substituted heteroaryl);

R$^{3a}$ is hydrogen or methyl, or R$^3$ and R$^{3a}$, taken together are —(CH$_2$)$_d$—where d is an interger from 2 to 6;

R$^4$ is phenyl, substituted phenyl, —(CH$_2$)$_m$phenyl, —(CH$_2$)$_m$(substituted phenyl), cycloalkyl, or benzofused cycloalkyl;

R$^5$ is hydrogen, lower alkyl, cycloalkyl, phenyl, substituted phenyl, —(CH$_2$)$_n$cycloalkyl, —(CH$_2$)$_n$phenyl, —(CH$_2$)$_n$(substituted phenyl), or —(CH$_2$)$_n$(1- or 2-naphthyl);

$R^6$ is hydrogen, fluorine, oxo, lower alkyl, cycloalkyl, phenyl, substituted phenyl, naphthyl, —$(CH_2)_n$cycloalkyl, —$(CH_2)_n$phenyl, —$(CH_2)_n$(substituted phenyl), —$(CH_2)_n$(1- or 2-naphthyl), —$OR^{10}$, —$SR^{11}$, or —$NHCOR^9$;

$R^7$ is hydrogen, oxo, lower alkyl, cycloalkyl, phenyl, substituted phenyl, naphthyl, —$(CH_2)_n$cycloalkyl, —$(CH_2)_n$phenyl, $(CH_2)_n$(substituted phenyl), or —$(CH_2)_n$(1- or 2-naphthyl);

$R^8$ is lower alkyl, cycloalkyl, —$(CH_2)_n$cycloalkyl, —$(CH_2)_n$phenyl, —$(CH_2)_n$(substituted phenyl), —$(CH_2)_n$(1- or 2-naphthyl), or —$COR^9$;

$R^9$ is hydrogen, lower alkyl, cycloalkyl, phenyl, substituted phenyl, naphthyl, —$(CH_2)_n$cycloalkyl, —$(CH_2)_n$phenyl, —$(CH_2)_n$(substituted phenyl), —$(CH_2)_n$(1- or 2-naphthyl), —$OR^{12}$, or —$NR^{13}R^{14}$;

$R^{10}$ is hydrogen, lower alkyl, cycloalkyl, phenyl, substituted phenyl, naphthyl, —$(CH_2)_n$cycloalkyl, —$(CH_2)_n$phenyl, —$(CH_2)_n$(substituted phenyl), or —$(CH_2)_n$(1- or 2-naphthyl);

$R^{11}$ is lower alkyl, cycloalkyl, phenyl, substituted phenyl, naphthyl, —$(CH_2)_n$cycloalkyl, —$(CH_2)_n$phenyl, —$(CH_2)_n$(substituted phenyl), or —$(CH_2)_n$(1- or 2-naphthyl);

$R^{12}$ is lower alkyl, cycloalkyl, —$(CH_2)_n$cycloalkyl, —$(CH_2)_n$phenyl, —$(CH_2)_n$(substituted phenyl), or —$(CH_2)_n$(1- or 2-naphthyl);

$R^{13}$ is hydrogen, lower alkyl, cycloalkyl, phenyl, substituted phenyl, naphthyl, substituted naphthyl, —$(CH_2)_n$cycloalkyl, —$(CH_2)_n$phenyl, —$(CH_2)_n$(substituted phenyl), or —$(CH_2)_n$(1- or 2-naphthyl);

$R^{14}$ is hydrogen or lower alkyl;

or $R^{13}$ and $R^{14}$ taken together form a five to seven membered carbocyclic or heterocyclic ring;

$R^{15}$ is phenyl, substituted phenyl, naphthyl, substituted naphthyl, heteroaryl, substituted heteroaryl, —$(CH_2)_n$phenyl, —$(CH_2)_n$(substituted phenyl), —$(CH_2)_n$(1- or 2-naphthyl), —$(CH_2)_n$(heteroaryl), or —$(CH_2)_n$(substituted heteroaryl);

$R^{16}$ and $R^{17}$ are independently lower alkyl, cycloalkyl, phenyl, substituted phenyl, naphthyl, phenylalkyl, (substituted phenyl)alkyl, or (cycloalkyl)alkyl;

$R^{18}$ and $R^{19}$ are independently hydrogen, alkyl, phenyl, substituted phenyl, —$(CH_2)_n$phenyl, —$(CH_2)_n$(substituted phenyl), or $R^{18}$ and $R^{19}$ taken together are —$(CH=CH)_2$—;

$R^{20}$ is hydrogen, alkyl, phenyl, substituted phenyl, —$(CH_2)_n$phenyl, or —$(CH_2)_n$(substituted phenyl);

$R^{21}$, $R^{22}$ and $R^{23}$ are independently hydrogen or alkyl;

X is —$CH_2$—, —$(CH_2)_2$—, —$(CH_2)_3$—, or —S—;

$Y^1$ is —O— or —$N(R^{23})$—;

$Y^2$ is —$CH_2$—, —O—, or —$N(R^{23})$—;

a is 0 or 1;

b is 1 or 2, provided that when a is 1 then b is 1;

c is 1 or 2, provided that when c is 1 then a is 0 and b is 1;

m is 1 or 2; and n is 1, 2, 3 or 4, or a pharmaceutically acceptable salt thereof.

31. The method of claim 27 wherein:
$R^1$ is substituted phenyl;
$R^{1'}$ is hydrogen;
$R^2$ is hydrogen or lower alkyl;
B is hydrogen or —$CH_2ZR^{15}$ where Z is oxygen and $R^{15}$ is substituted phenyl;
A is a natural or unnatural amino acid of Formula IIa:

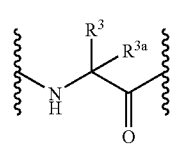

IIa $R^3$ is lower alkyl; and
$R^{3a}$ is hydrogen.

32. The method of claim 31 wherein $R^1$ is phenyl substituted with one or more alkyl groups.

33. The method of claim 32 wherein $R^1$ is 2-tert-butyl-phenyl.

34. The method of claim 31 wherein $R^1$ is phenyl substituted with one or more halogen atoms.

35. The method of claim 34 wherein $R^1$ is 2-fluorophenyl.

36. The method of claim 34 wherein $R^1$ is 2-bromo-4-chloro-6-fluoro-phenyl.

37. The method of claim 31 wherein $R^1$ is 2-trifluoromethylphenyl.

38. The method of claim 31 wherein $R^1$ is 3-trifluoromethylphenyl.

39. The method of claim 31 wherein $R^2$ is hydrogen.

40. The method of claim 31 wherein $R^2$ is lower alkyl.

41. The method of claim 40 wherein $R^2$ is ethyl.

42. The method of claim 40 wherein $R^3$ is methyl.

43. The method of claim 31 wherein B is hydrogen.

44. The method of claim 31 wherein B is —$CH_2ZR^{15}$ and $R^{15}$ is phenyl substituted with one or more halogen atoms.

45. The method of claim 44 wherein $R^{15}$ is 2,6-dihalophenyl, 2,4,6-trihalophenyl, or 2,3,5,6-tetrahalophenyl.

46. The method of claim 45 wherein $R^{15}$ is 2,3,5,6-tetrafluorophenyl.

47. The method of claim 31 wherein $R^1$ is 2-bromo-4-chloro-6-fluoro-phenyl, $R^3$ is methyl, B is hydrogen.

48. The method of claim 47 wherein the compound is (3S)-3-[N-(N'-(2-bromo-4-chloro-6-fluoro-phenyl)Oxamyl) Alaninyl]Amino-4-Oxobutanoic Acid.

49. The method of claim 31 wherein the compound is (3S)-3-[N-(N'-(2-tert-Butylphenyl)Oxamyl)Alaninyl] Amino-5-(2',3',5',6'-Tetrafluorophenoxy)-4-Oxopentanoic Acid.

50. The method of claim 31 wherein the compound is (3S)-3-[N-(N'-(2-Trifluoromethylphenyl)Oxamyl)Alaninyl] Amino-5-(2',3',5',6'-Tetrafluorophenoxy)-4-Oxopentanoic Acid.

51. The method of claim 27 wherein B is —$CH_2ZR^{15}$ wherein Z is oxygen.

52. The method of claim 51 wherein $R^{15}$ is heteroaryl or substituted heteroaryl.

53. The method of claim 52 wherein $R^{15}$ is pyrimidyl or substituted pyrimidyl.

54. The method of claim 53 wherein $R^{15}$ is pyrimidyl substituted with trifluoromethyl.

* * * * *